US006509515B2

(12) United States Patent
Hsiao et al.

(10) Patent No.: US 6,509,515 B2
(45) Date of Patent: *Jan. 21, 2003

(54) TRANSGENIC MICE EXPRESSING MUTANT HUMAN APP AND FORMING CONGO RED STAINING PLAQUES

(75) Inventors: Karen Hsiao, North Oaks, MN (US); David R. Borchelt, Baltimore, MD (US); Sangram S. Sisodia, Baltimore, MD (US)

(73) Assignees: Regents of the University of Minnesota, Minneapolis, MN (US); Johns Hopkins University, Baltimore, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/260,897

(22) Filed: Mar. 2, 1999

(65) Prior Publication Data

US 2002/0019992 A1 Feb. 14, 2002

Related U.S. Application Data

(63) Continuation of application No. 08/664,872, filed on Jun. 17, 1996, now Pat. No. 5,877,399, which is a continuation-in-part of application No. 08/644,691, filed on May 10, 1996, now abandoned, which is a continuation-in-part of application No. 08/189,064, filed on Jan. 27, 1994, now abandoned.

(51) Int. Cl.[7] .................. A01K 67/00; A01K 67/027; G01N 33/00

(52) U.S. Cl. .................. 800/12; 800/18; 800/3
(58) Field of Search .................. 800/3, 12, 13, 800/14, 18

(56) References Cited

U.S. PATENT DOCUMENTS

| | | | |
|---|---|---|---|
| 4,873,191 A | 10/1989 | Wagner et al. | 435/172.3 |
| 5,387,742 A | 2/1995 | Cordell | 800/2 |
| 5,455,169 A | 10/1995 | Mullan | 435/240.2 |
| 5,604,102 A | 2/1997 | McConlogue et al. | 435/7.1 |
| 5,612,486 A * | 3/1997 | Mcconlogue et al. | 800/2 |
| 5,811,633 A * | 9/1998 | Wadsworth et al. | 800/2 |
| 5,877,399 A * | 3/1999 | Hsiao et al. | 800/2 |

FOREIGN PATENT DOCUMENTS

| | | |
|---|---|---|
| EP | 0 451 700 A1 | 10/1991 |
| EP | 0 653 154 A2 | 5/1995 |
| WO | WO 89/06689 | 7/1989 |
| WO | WO 91/19810 | 12/1991 |
| WO | WO 92/06187 | 4/1992 |
| WO | WO 92/13069 | 8/1992 |
| WO | WO 93/02189 | 2/1993 |
| WO | WO 93/14200 | 7/1993 |
| WO | WO 95/11968 | 5/1995 |

OTHER PUBLICATIONS

Lannfelt et al (1993) Behav. Brain Res. 207–213.*
Felsenstein et al (1995) Alz. Parkinson's Diseases, ed. I. Hannin et al, Plenum Press, New York, Ny 401–409.*
Higgins et al (1993) Annals NY Acad. Sci. 695, 224–227.*
Quon et al (1991) Nature 352, 239–241.*
Mullen et al (1992) Nature Genetics 1, 345–347.*
Scott et al (1989) Cell 59, 847–857.*
Ali et al., Abstract 616.8, *Soc. Neurosci. Abstracts,* 18(2).
Andra et al., "Expression of APP in Transgenic Mice: A Comparison of Neuron–Specific Promoters," *Neurobiology of Aging,* 1996, 17(2):183–190.
Borchelt et al., "Familial Alzheimer's Disease–Linked Presenilin 1 Variants Elevate Aβ1–42/1–40 Ratio In Vitro and In Vivo," *Neuron,* 1996, 17: 1005–1013.
Borchelt et al., "Transgenic Mouse Models of Alzheimer's Disease and Amyotrophic Lateral Sclerosis," *Brain Pathology,* 1998, 8:735–757.
Buxbaum, et al., "Expression of APP in Brains of Transgenic Mice Containing the Entire Human APP Gene," *Biochemical and Biophysical Research Communications,* 1993, 197(1): 639–645.
Czech et al., "Alzheimer's Disease and Transgenic Mice," *J. Neural Transm.,* 1994, 44:219–230.
Fisher, "Athena Neurosciences Makes Itself Heard in Battle Against Alzheimer's," *The New York Times,* Feb. 5, 1995: C1.
Games et al., "Alzheimer–Type Neuropathology in Transgenic Mice Overexpressing V717F β–Amyloid Precursor Protein," *Nature,* 1995, 373(6514): 523–527.

(List continued on next page.)

Primary Examiner—Deborah Crouch
(74) Attorney, Agent, or Firm—Fish & Richardson, P.C., P.A.

(57) ABSTRACT

Provided is a transgenic non-human eukaryotic animal whose germ cells and somatic cells contain the amyloid precursor protein sequence introduced into the animal, or an ancestor of the animal, at an embryonic stage. In mice, an age-related CNS disorder characterized by agitation, neophobia, seizures, inactivity, diminished cerebral glucose utilization, cortico-limbic gliosis, and death, develops. An acceleration of this disorder occurs in transgenic mice expressing human and mouse Alzheimer amyloid precursor proteins (APP) produced using a hamster prion protein gene-derived cosmid vector that confers position-independent, copy number-dependent expression. In transgenic mice the disorder develops in direct relationship to brain levels of transgenic APP, but mutant APP confers the phenotype at lower levels of expression than wild-type APP. The disorder occurs in the absence of extracellular amyloid deposition, indicating that some pathogenic activities of APP are dissociated from amyloid formation.

6 Claims, 22 Drawing Sheets

OTHER PUBLICATIONS

Gandy et al., "Amyloidogensis in Alzheimer's Disease: Some Possible Therapeutic Opportunities," *Trends in Pharmacological Sciences*, 1992, 13:108–113.

Greenberg et al., Abstract 616.7, *Soc. Neurosci. Abstracts*, 1992, 18(2).

Greenberg et al., "APP Transgenesis: Approaches Toward the Development of Animal Models for Alzheimer Disease Neuropathology," *Neurobiology of Aging*, 1996, 17(2):153–171.

Higgins et al., "Transgenic Mouse Brain Histopathology Resembles Early Alzheimer's Disease," *Annals of Neurology*, 1994, 35(5):598–607.

Higgins et al., "Early Alzheimer disease–like histopathology increases in frequency with age in mice transgenic for β–APP751," *Proc. Natl. Acad. Sci. USA*, 1995, 92(10):4402–4406.

Howland et al., "Mutant and Native Human β–Amyloid Precursor Proteins in Transgenic Mouse Brain," *Neurobiology of Aging*, 1995, 16(4):685–699.

Hsiao, "Understanding the Biology of β–Amyloid Precursor Proteins in Transgenic Mice," *Neurobiology of Aging*, 1995, 16(4):705–706.

Hsiao et al., "Age–Related CNS Disorder and Early Death in Transgenic FVB/N Mice Overexpressing Alzheimer Amyloid Precursor Proteins," *Neuron*, 1995, 15:1203–1218.

Hsiao, "From prion diseases to Alzheimer's disease," *J. Neural. Transm.*, 1997, 49:135–144.

Hsiao, et al., "Correlative Memory Deficits, Aβ Elevation, and Amyloid Plaques in Transgenic Mice," *Science*, 1996, 274:99–102.

Irizarry et al., "Aβ Deposition Is Associated with Neuropil Changes, but not with Overt Neuronal Loss in the Human Amyloid Precursor Protein V717F (PDAPP) Transgenic Mouse," *J. Neuroscience*, 1997, 17(18):7053–7059.

Johnson–Wood et al., "Amyloid precursor protein processing and Aβ$_{42}$ deposition in a transgenic mouse model of Alzheimer disease," *Proc. Natl. Acad. Sci. USA*, 1997, 94:1550–1555.

Jucker et al., "Age–Associated Inclusions in Normal and Transgenic Mouse Brain," *Science*, 1992, 255:1443–1445.

Kawabata et al., "Retraction," *Nature*, 1992, 356:265.

Koliatsos et al., "Neurotrophic Strategies for Treating Alzheimer's Disease: Lessons from Basic Neurobiology and Animal Models," *Alzheimer's Disease: Amyloid Precursor Proteins, Signal Transduction, and Neuronal Transplantation*[a], 1993, vol. 695, pp. 292–299.

LaFerla et al., "The Alzheimer's Aβ peptide induces neurodegeneration and apoptotic cell death in transgenic mice," *Nature Genetics*, 1995, 9:21–29.

Lamb, "Making models for Alzheimer's disease," *Nature Genetics*, 1995, 9:4–6.

Marx, "Alzheimer's Research Moves to Mice," *Science*, 1991, 253:266–267.

Marx, "Major Setback for Alzheimer's Models," *Science*, 1992, 1200–1202.

Miller and Anderton, "Alzheimer's disease: transgenic models to test new chemicals and pharmaceuticals," *Current Opinion in Biotechnology*, 1992, 3:683–686.

Mucke et al., "Synaptotrophic effects of human amyloid β protein precursors in the cortex of transgenic mice," *Brain Research*, 1994, 666(2):151–167.

Neve et al., "Transgenic Mice Expressing APP–C100 in the Brain," *Neurobiology of Aging*, 1996, 17(2):191–203.

Price et al., "Alzheimer's Disease–Type Brain Abnormalities in Animal Models," *Down Syndrome and Alzheimer Disease*, 1992, Wiley–Liss, Inc., pp. 271–287.

Price and Sisodia et al., "Cellular and Molecular Biology of Alzheimer's Disease and Animal Models," *Annu. Rev. Med.*, 1994, 45:435–446.

Rockenstein et al., "Levels and Alternative Splicing of Amyloid βProtein Precursor (APP) Transcripts in Brains of APP Transgenic Mice and Humans with Alzheimer's Disease," *J. Biol. Chem.*, 1995, 270(47):28257–28267.

Sandhu et al., "NMDA and AMPA Receptors in Transgenic Mice Expressing Human β–Amyloid Protein," *J. Neurochemistry*, 1993, 61(6):2286–2289.

Schenk et al., "The Protential Utility of Transgenic Mice Harboring β–Amyloid Precursor Protein," *Neurobiology of Aging*, 1995, 16(4):711–713.

Sisodia and Price, "Amyloidogenesis in Alzheimer's disease: basic biology and animal models," *Current Opinion in Neurobiology*, 1992, 2:648–652.

Sisodia et al., "Cellular and Molecular Biology of Alzheimer's Disease and Animal Models," *Neuroimaging Clinics of North America*, Drayer (ed.), W. B. Saunders Company, 1995, 5:59–68.

Sturchler–Pierrat et al., "Two amyloid precursor protein transgenic mouse models with Alzheimer disease–like pathology," *Proc. Natl. Acad. Sci. USA*, 1997, 94:13287–13292.

Tanzi, "Clinical Implications of Basic Research—A Promising Animal Model of Alzheimer's Disease," *New England Journal of Medicine*, 1995, 332(22):1512–1513.

Yamaguchi et al., "Transgenic mice for the amyloid precursor protein 695 isoform have impaired spatial memory," *NeuroReport*, 1991, 2(12):781–784.

Zhao et al., "β–Secretase Processing of the β–Amyloid Precursor Protein in Transgenic Mice is Efficient in Neurons but Inefficient in Astrocytes," *J. Biol. Chem.*, 1996, 271(49):31407–31411.

Mullan et al., *Nature Genetics*, 1:345–347, 1992.

Scott et al., *Cell*, 59:847–857, 1989.

Moran et al., *Proced. Natl. Acad. Sci.*, 92:5341–5345, 1995.

Felsenstein et al., *Alz. and Parkin. Disiases*, ed. Itkenen, Plenum Press, NY, 401–409, 1995.

Lannfelt et al., *Behav. Brain Res.*, 57:207–213, 1993.

Higgins et al., *Annals NY Acad. Sci.*, 695:224–227, 1993.

Quon et al., *Nature*, 352:239–241, 1991.

Chartier–Harlin et al., *Nature*, 353:844–846, 1991.

Fukuchi et al., *Soc. Neurosci. Abstracts*, 19:1035, 1993.

Goate et al., *Nature*, 349:704–706, 1991.

Goldgaber et al., *Science*, 235:877–880, 1987.

Greenberg, *Soc. Neurosci. Abstracts*, 19:1035.

Hendriks et al., *Nature Genetics*, 1:218–221, 1992.

Hsiao et al., *Science*, 250:1587–1590, 1990.

Kammescheidt et al., *Proc. Natl. Acad. Sci. USA*, 89:10857–10861, 1992.

Kang et al., *Nature*, 325:733–736, 1987.

Kawabata et al., *Nature*, 354:476–478, 1991.

Kitaguchi et al., *Nature*, 331:530–532, 1988.

Kozak, *J. Cell Biol.*, 109:229–241, 1989.

Lamb et al., *Nature Genetics*, 5:22–30, 1993.

Levy et al., *Science*, 248:1124–1126, 1990.

Lieberburg, Abstract 421.15, *Soc. Neurosci. Abstracts*, 19:1035, 1993.

Murrell et al., *Science*, 254:97–99, 1991.

Ponte et al., *Nature*, 331:525–527, 1988.

Robakis et al., *Proc. Natl. Acad. Sci. USA,* 84:4190–4194, 1987.
Savage et al., *Soc. Neurosci. Abstracts,* 19:1035, 1993.
Howland et al., *Soc. Neurosci. Abstracts,* 19:1035, 1993.
Tanzi et al., *Science,* 235:880–884, 1987.
Tanzi et al., *Nature,* 331:528–530, 1988.
Wirak et al., *Science,* 253:323–325, 1991.
Hyman et al., *Current Opinion Neurol. Neurosurg.,* 5:88–93, 1992.
Sandu et al., *J. Biol. Chem.,* 266:21331–21334, 1991.

\* cited by examiner

1. KM670/671NL
2. A692G
3. E693Q
4. V717I
5. V717G
6. V717F
7. VVM717/721/722IAV

▬ APP coding sequence with CS1 translation initiation sequence as illustrated in FIG. 6

▬ APP coding sequence with CS2 translation initiation sequence as illustrated in FIG. 7

A = CTG ACC ACT CGA CCA GGT TCT GGG T
P = GTG GAT AAC CCC TCC CCC AGC CTA GAC CA

- ■ APP CODING SEQUENCE
- ▨ 1.6 kb SEQUENCE FROM HAMSTER PrP 3'-UNTRANSLATED REGION
- —— DNA SEQUENCES FROM THE HAMSTER PrP COSMID VECTOR AS ILLUSTRATED IN FIGS. 4&5

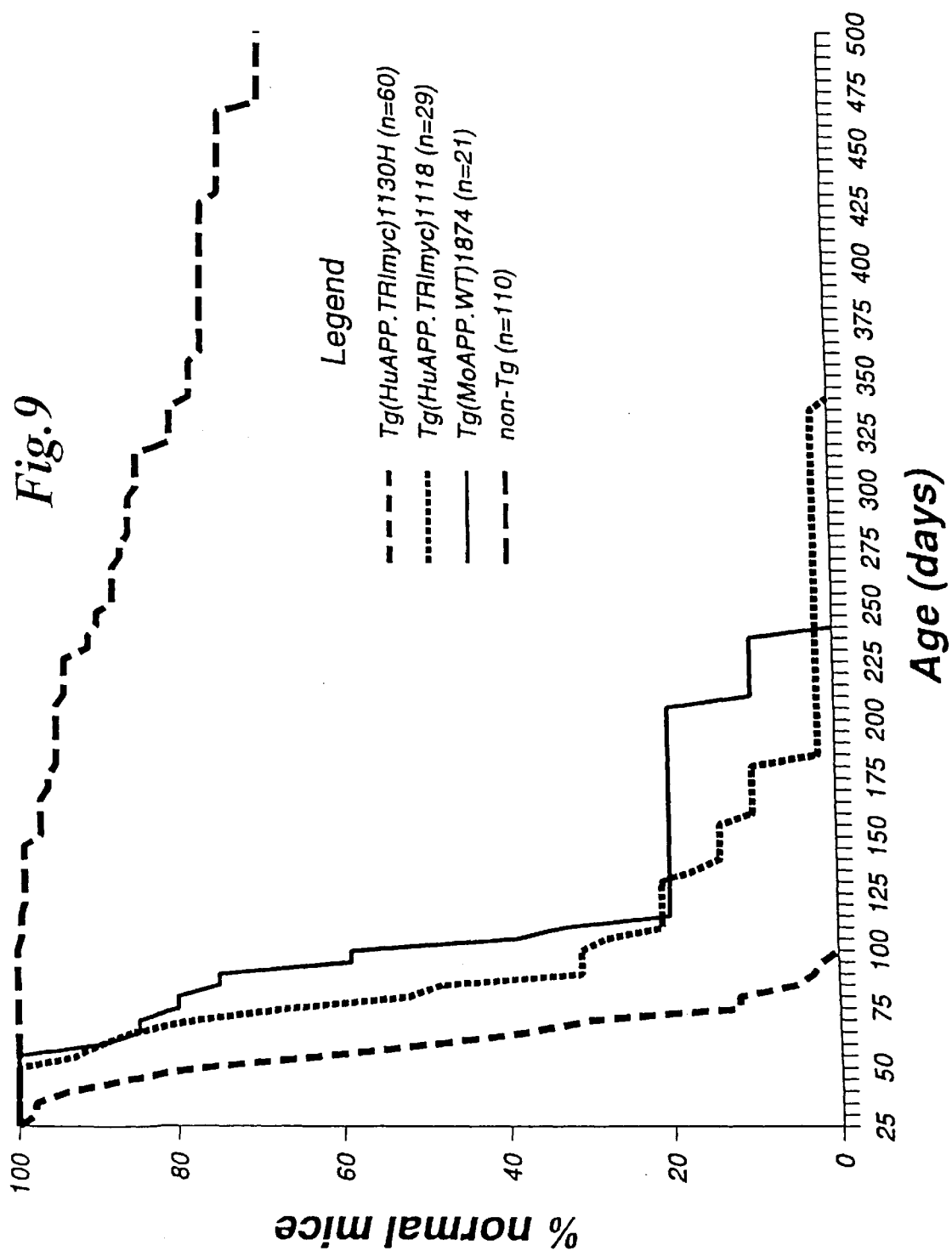

Fig. 16c
Hidden platform
12 to 15 month-old retested mice
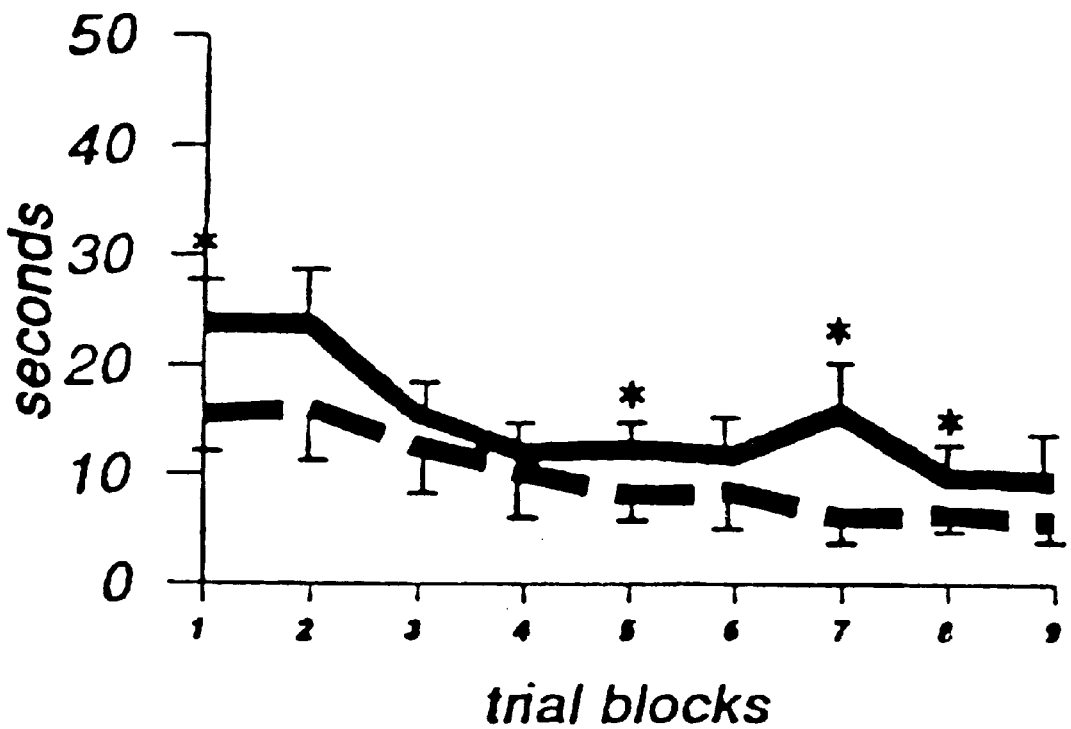
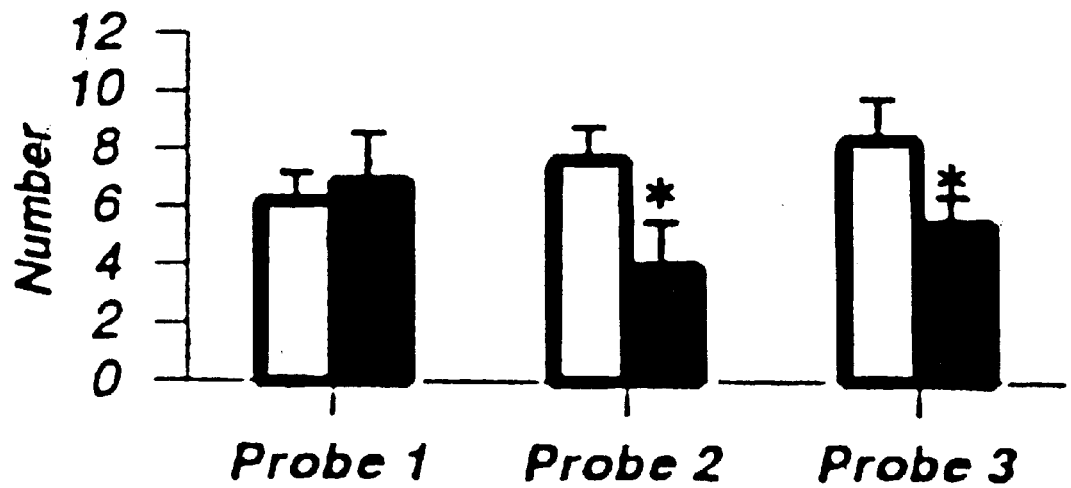

Visible platform
9-10 month-old mice
Escape latencies

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
      (A) LENGTH: 9 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

GCGATGCTG                                                                                    9

(2) INFORMATION FOR SEQ ID NO: 2:

(i) SEQUENCE CHARACTERISTICS:
      (A) LENGTH: 9 base pairs
      (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO: 2:

ACCATGCTG                                                                9

(2) INFORMATION FOR SEQ ID NO: 3:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

ACCATGGTG                                                                9

(2) INFORMATION FOR SEQ ID NO: 4:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

ACGATGCTG                                                                9

(2) INFORMATION FOR SEQ ID NO: 5:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

ATCATGGCG                                                                9

(2) INFORMATION FOR SEQ ID NO: 6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

AAGTCGACAC CATGCTGCCC GGTTTGGCAC T                                       31

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO: 7:

AAGGTACCTC CCAGCGCCCG AGCC                                              24

(2) INFORMATION FOR SEQ ID NO: 8:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

AAAAAAGTCG ACACCATGGT GCCCGGTTTG GCACT                                  35

(2) INFORMATION FOR SEQ ID NO: 9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

AAGGTACCTC CAGCGCCCGA GCC                                               23

(2) INFORMATION FOR SEQ ID NO: 10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

CCGAGATCTC TGAAGTGAAG ATGGATG                                           27

(2) INFORMATION FOR SEQ ID NO: 11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

AAGCTTGGCG CCTTTGTTTG AACCCAC                                           27

(2) INFORMATION FOR SEQ ID NO: 12:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

CCGAGATCTC TGAAGTGAAT CTGGATGC                                          28

(2) INFORMATION FOR SEQ ID NO: 13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

```
CTGACCACTC GACCAGGTTC TGGGT                                              25
```

(2) INFORMATION FOR SEQ ID NO: 14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

```
GTGGATAACC CCTCCCCCAG CCTAGACCA                                          29
```

(2) INFORMATION FOR SEQ ID NO: 15:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

```
AAGCGGCCAA AGCCTGGAGG GTGGAACA                                           28
```

(2) INFORMATION FOR SEQ ID NO: 16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

```
GTCGACACCA TGCTGCCC                                                      18
```

(2) INFORMATION FOR SEQ ID NO: 17:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

```
AACTAGCAGC TG                                                            12
```

TRANSGENIC MICE EXPRESSING MUTANT HUMAN APP AND FORMING CONGO RED STAINING PLAQUES

CROSS-REFERENCE TO RELATED APPLICATIONS

This application is a con of U.S. Ser. No. 08/664,872 filed Jun. 17, 1996 now U.S. Pat. No. 5,877,399 is a continuation-in-part of U.S. Ser. No. 08/644,691 filed May 10, 1996, now abandoned which is a continuation-in-part of U.S. Ser. No. 08/189,064 filed Jan. 27, 1994, now abandoned which disclosures are incorporated herein by reference.

NOTICE REGARDING FEDERAL FUNDING

This research was supported in parts by grants from the National Institutes of Health, including grant number K08-NS01419. The government may have rights in this invention.

INTRODUCTION

Technical Field

The invention relates to transgenic animals with progressive neurologic disease characterized by both behavioral and neuropathological changes as compared to nontransgenic age-matched animals and their use for screening for agents which can be used to treat or cure progressive neurologic syndromes such as Alzheimer's disease. The invention is exemplified by transgenic mice which express native or mutant β-amyloid precursor protein in brain tissue at super-endogenous levels under control of prion protein gene regulatory sequences.

Background

The term degenerative as applied to diseases of the nervous system is used to designate a group of disorders in which there is gradual, generally relentlessly progressing wasting away of structural elements of the nervous system; many of the conditions so designated depend upon abnormal genetic factors. The degenerative diseases manifest themselves by a number of syndromes distinguished by their clinical and pathological features. Nevertheless, there are certain aspects common to all. These aspects include a gradually progressive course of disease onset, bilaterally symmetric distribution of the changes brought about by the disease, and in many cases, the almost selective involvement of anatomically or physiologically related systems of neurons. Typically the pathologic process is one of slow involution of nerve cell bodies or their prolongations as nerve-fibers.

Among the degenerative diseases of the nervous system are syndromes in which the outstanding feature is progressive dementia; the syndromes in this group include senile dementia and Alzheimer's disease. Senile dementia is a fairly frequent condition of old age, not only in humans but also in other animals. Alzheimer's disease is a pathologically identical, but much more infrequent, progressive dementia which come son well before the senile period. The distinction between the two conditions is purely clinical; pathologically they differ only in that the characteristic abnormalities tend to be more severe and widespread in cases of Alzheimer's disease and to begin at an earlier age than at the senile period.

Alzheimer's disease (AD) shows a slowly progressive mental deterioration with failure of memory, disorientation and confusion leading to profound dementia. The disease predominantly involves limbic and cortical regions of the brain. There are several histologic features, but two are striking. First, argyrophilic plaques containing the amyloidogenic Aβ fragment of amyloid precursor protein (APP) are scattered throughout the cerebral cortex and hippocampus. Second, neurofibrillary tangles are found in pyramidal neurons predominantly located in the neocortex, hippocampus, and nucleus basalis of Meynert. There are other changes, also. Granulovacuolar degeneration in the pyramidal cells of the hippocampus, which have been considered by some to be more specific for AD than plaques or neurofibrillary tangles, are observed. Finally, there is neuronal loss and gliosis in the cortex and hippocampus.

There are patients with dementia who lack the pathologic features of AD (and therefore by definition have a different disease), and conversely, there are individuals with many of the pathologic features of AD who were not demented prior to death. A diagnosis of AD requires that both the clinical and the pathological features characteristic for the disease be present in the patient; the diagnosis cannot be made with certainty from either clinical or pathological features alone. Whether neural dynsfunction and clinical abnormalities precede the development of the pathologic features, particularly the amyloid plaques and neurofibrillary tangles, is unknown.

The clinical manifestations of AD predict the regions of affected brain structures in the forebrain, including the cerebral cortex, hippocampus, amygdala, and parahippocampal gyri. These regions are known as the cortico-limbic areas of the brain. The hindbrain is spared, including the cerebellum, the pontine and the medullary nuclei. Within the cerebral neocortex, the primary cortical area is relatively spared, which corresponds to the relative sparing of basic motor and sensory cortical functions observed clinically.

Research into progressive neurologic disorders such as AD, and means for screening for agents which can be used to treat or cure these disorders, has been seriously impeded by the lack of easily accessible animal models. Some aspects of the neuropathology of aged primates are similar to those of human AD (Price, et al., (1992) *J. Neurobiol*, 23:1277–1294). Aged primates develop amyloid plaques and forme fruste neurofibrillary tangles. No other animals studied develop a disease resembling AD as closely as do aged primates; aged primates are impractical to study in large numbers and their use raises both moral and economic issues.

Transgenic mice harboring APP transgenes have been described; however, the reported transgene product expression falls considerably short of endogenous levels of APP; total APP levels in these order transgenic mice have not exceeded 150% of endogenous levels, and fails to generate a disease phenotype with a progressive neurobehavioral disorder accompanied by pathology in the cortico-limbic regions of the brain. In these other transgenic mice, there have been no signs of progressive neurologic disorder or of neuropathologic changes in the brain which may be regarded as evidence of a true neurologic disease nor have changes such as neurobehavioral changes which can be used in live animals as a means of screening for agents which prevent, ameliorate or cure a progressive neurologic disorder been described.

Missense point mutations in the gene coding for amyloid precursor proteins have been linked to familial AD. However, despite the discovery of disease associated mutations in APP, most published attempts to create transgenic animals with AD have involved only wild-type APP transgenes in mice (Kawabata, et al., (1991) *Nature* 354, 476–478; Quon, et al., (1991) *Nature* 352, 239–41; Wirak, et al., (1991) *Science* 253, 323–325; Kammesheidt, et al., (1992) *Proc Natl Acad Sci U.S.A.* 89, 10857–61; Lamb, et al., (1993) *Nature Genetics* 5, 22–30.) Unfortunately, several of the published studies purporting pathology have been confounded by inadequate documentation of transgene product expression and/or misinterpretation of pathology. Two have been retracted (Kawabata, et al., (1991) *Nature* 354, 476–478; and Wirak, et al., (1991) *Science* 253, 323–325.

Previous efforts to create a model of AD in transgenic mice have been discouraging. In most cases, transgene product expression comparable to or exceeding endogenous levels of APP was not achieved and the transgenes did not encode mutated APP. PCT/US92/11276 reports methods for using mutant genes. In some cases, the entire APP gene was not expressed, just the carboxyl terminus (Kammesheidt, et al., (1992) *Proc Natl Acad Sci U.S.A.* 89, 10857–61); expression of only the carboxyl terminus of APP may overlook any biologic effect that the rest of the APP molecule may exert in AD.

Preamyloid APP plaques have been observed in some transgenic mice. However, preamyloid APP plaques are not necessarily indicative of a disease, since they are routinely observed in human brain regions, such as the cerebellum, which are devoid of other signs of pathology or clinical manifestations. Increased APP immunoreactivity located within vesicular structures in hippocampal neurons of transgenic mice has been reported, but the significance of this immunoreactivity is unclear since the mice exhibited neither a progressive neurobehavioral disorder nor evidence of true neuropathology.

In general, the ceaselessly progressive course of neurodegenerative diseases is uninfluenced by current treatment modalities. It therefore is of interest to develop a transgenic non-human animal model for degenerative neurologic diseases such as senile dementia and AD wherein the animal develops a progressive degenerative neurologic disease of the cortico-limbic brain resembling the disease, both clinically and pathologically (e.g. the gliosis and the specific brain regions affected). It also is desirable that the animal develops neurologic disease within a fairly short period of time from birth, facilitating the analysis of multigenerational pedigrees. The model can be used to study the pathogenesis and treatment of degenerative neurologic diseases since there is a distinct and robust clinical and pathologic phenotype to examine and score in the live animal.

RELEVANT LITERATURE

Transgenic mice (Swiss Webster x C57B6/DBA2 F1) expressing three isoforms of mutant βAPPV717F with an overrepresentation of KPI-containing isoforms show Alzheimer-type neuropathology including abundant thioflavin S-positive Aβdeposits, neuritic plaques, synaptic loss, astrocytosis and microgliosis (Games, et al., *Nature* 373:523–527 (1995)), but deficits in memory and learning have not yet been reported. Transgenic mice (JU) expressing human wild-type βAPP751 show deficits in spatial reference and alternation tasks by 12 months of age (Moran, et al., *Proc. Natl. Acad. Sci. USA* 92:5341–5345 (1995)) but only 4% of aged (>>12 months) transgenic mice exhibited rare diffuse Aβ deposits that do not stain with Congo red dye (Higgins, et al., *Annals of Neurology* 35:598–607 (1994)). Quon, et al. (1991) *Nature* 352:239 describe transgenic mice containing human amyloid precursor protein genes. Lamb, et al. (1993) *Nature Genetics* 5:22 describe transgenic mice in which the amount of amyloid precursor protein expressed is approximately 50% over endogenous levels. PCT application US92/11276 discloses methods for constructing transgenic mice and rats which would express, under various promoters, three forms of the β-amyloid precursor protein (APP), APP695, APP751, and APP770. No data are provided in the specification as to whether APP expression is obtained in vivo using these methods. Also see U.S. Pat. No. 5,455,169 and WO 9213069.

Other transgenic mouse studies of Alzheimer amyloid precursor (APP) protein expression include the following. Greenberg, (1993) Abstract 421.12, *Society for Neuroscience Abstracts* 19:1035 discloses APP protein gene expression using MAPP and mMt-I promoters. Schwartz, et al. ((1993) Abstract 421.13, *Society for Neuroscience Abstracts*, 19:1035) disclose neuron-specific expression of human β-amyloid precursor protein (APP) in transgenic mice. Savage, et al. ((1993) Abstract 421.14 *Society of Neuroscience Abstracts* 19:1035) disclose human amyloid precursor protein expression in transgenic mice as a model of Alzheimer's disease. Lieberburg, ((1993) *Abstract* 421.15, *Science for Neuroscience Abstracts* 19:1035) disclose expression of human amyloid precursor protein in transgenic mice using the NSE promoter. Fukuchi, et al. ((1993) *Abstract* 421.16, *Society for Neuroscience Abstracts* 19:1035) disclose intestinal β-amylolidosis in transgenic mice. A chicken β-actin promoter and CMV enhancer were used for expressing the APP protein gene.

Wagner, et al. ((1983) *Proc. Natl. Acad. Sci. U.S.A.* 78:5016) describe transgenic mice containing human globin genes. Scott, et al. ((1989) *Cell* 59:847) describe transgenic mice containing hamster prion protein genes. Hsiao, et al. ((1990) *Science* 250:1587) describe transgenic mice containing mutant human prion protein genes. Hsiao disclosed a model for Gerstmann-Straussler-Scheinker disease (GSS), a rare neurodegenerative disease caused by mutations in the prion protein (PrP) gene, in transgenic mice in which levels of mutant transgene product exceeding endogenous levels were needed to generate a clinical and pathological phenotype (Hsiao, et al. (1990) *Science* 250:1587–1590); Hsiao, et al. (1994) *Proc. Natl. Acad. Sci. U.S.A.* 91:9126–9130).

SUMMARY OF THE INVENTION

A transgenic non-human animal model for progressive neurologic disease is provided, together with methods and compositions for preparation of the animal model and methods for using it. The non-human mammals are obtained by the steps of introducing multiple copies of an expression cassette into the non-human mammal at an embryonic stage, and developing the embryo to term in a pseudo-pregnant foster female. The expression cassette comprises an amyloid precursor protein coding sequence operably joined to regulatory sequences for expression of the coding sequence in neurologic tissues at a level at least two to four-fold that of endogenous levels of wild-type amyloid precursor protein. The resulting transgenic non-human mammals develop progressive neurologic disease in the cortico-limbic areas of the brain. The transgenic animals find use for example in screening protocols for agents which can be used for treatment and/or prevention of progressive neurologic diseases.

BRIEF DESCRIPTION OF THE FIGURES

FIG. 9 shows age-related CNS dysfunction in transgenic and non-transgenic FVB mice. In two lines of Transgenic mice, Tg(HuAPP695).TRImyc)1130H and Tg(HuAPP695.TRImyc) 1118 expressing variant HuAPP at 3.6 and 1.4 times endogenous MoAPP levels, respectively, the average onset of illness was inversely related to APP levels. A subset of Tg(HuAPP695.WTmyc) 1874 mice and non-Transgenic mice developed clinical and pathological abnormalities similar to those in affected Transgenic mice, but with significantly lower penetrance at any given age.

FIG. 10 shows cortico-limbic hypertrophic astrocytic gliosis in transgenic and non-transgenic FVB mice exhibiting behavorial abnormalities. Coronal sections of cortico-limbic and brainstem structures reacted with antibody to GFAP show hypertrophic gliosis in cortico-limbic areas of animals exhibiting behavioral abnormalities.

FIG. 13 shows HuAPP expression in neurons of transgenic mice.

FIG. 16C, spatial reference learning and memory in the Morris water maze in N2 Tg2576 mice retested at 12 to 15 months of age. Although transgene positive mice were able to learn and remember the location of the submerged platform at two and six months of age, a subset of these mice showed significant impairment when they were retested at 12 to 15 months of age. Thirty-six spatial training trials (9 trial blocks) and three probe trials were performed. The transgene positive mice showed significantly prolonged escape latencies after the 5$^{th}$ trial block and decreased platform crossings in both the second and third probe trials. Stars indicate statistical significance (t-test), p<0.05).

DESCRIPTION OF THE PREFERRED EMBODIMENTS

Figure 1:
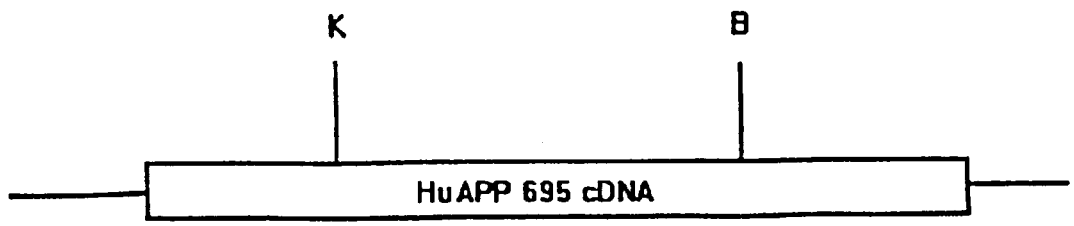
FIG. 1 is a diagrammatic representation of a HuAPP cDNA sequence.

The invention is directed to a transgenic non-human eukaryotic animal, preferably a rodent, such as a mouse, or other animal which is naturally able to perform learning and memory tests, together with methods and compositions for preparing and using the animal. The animal expresses an amyloid precursor protein (APP) sequence at a level in brain tissues such that the animal develops a progressive neurologic disorder within a short period of time from birth, generally within a year from birth, preferably within 2 to 6 months, from birth. The APP protein sequence is introduced into the animal, or an ancestor of the animal, at an embryonic stage, preferably the one cell, or fertilized oocyte, stage, and generally not later than about the 8-cell stage. The zygote or embryo is then developed to term in a pseudo-pregnant foster female. The amyloid precursor protein genes are introduced into an animal embryo so as to be chromosomally incorporated in a state which results in superendogenous expression of the amyloid precursor protein and the development of a progressive neurologic disease in the cortico-limbic areas of the brain, areas of the brain which are prominently affected in progressive neurologic disease states such as AD. The gliosis and clinical manifestations in affected transgenic animals are indicative of a true neurologic disease. The progressive aspects of the neurologic disease are characterized by diminished exploratory and/or locomotor behavior and diminished 2-deoxyglucose uptake/utilization and hypertrophic gliosis in the cortico-limbic regions of the brain. Further, the changes that are seen are similar to those that are seen in some aging animals.

The present invention offers several advantages over existing models for progressive neurologic disorders such as AD. The transgenic animals express high levels of either native APP or mutant APP and develop a neurologic illness accompanied by premature death. Measurable changes are observed in these animals, including the neuropathological changes such as gliosis and intracellular APP/Aβ accretions in the hippocampus and cerebral cortex and behavioral changes such as the diminished exploratory behavior and impaired performance on learning and memory tests. The behavioral changes provide a particular advantage in screening protocols for agents which can be used in a treatment for progressive neurologic disorders such as Alzheimer's disease because the results can be observed in live animals; it is unnecessary to wait until the animal is sacrificed to determine whether the agent is effective for its intended purpose.

Transgenic animals of the invention are constructed using an expression cassette which includes in the 5'–3' direction of transcription, a transcriptional and translational initiation region associated with gene expression in brain tissue, DNA encoding a mutant or wild-type APP protein, and a transcriptional and translational termination region functional in the host animal. One or more introns also can be present. For expression, of particular interest are initiation regions (also sometimes referred to as "promoters") which provide for preferential or at least substantially specific expression in brain as compared to other tissue. By "at least substantially" is intended that expression in brain tissue is greater than about 10 fold than in other tissue. Within the brain, of particular interest is expression in the cortico-limbic area. The transcriptional initiation region can be endogenous to the host animal or foreign or exogenous to the host animal. By foreign is intended that the transcriptional initiation region is not found in the wild-type animal host into which the transcriptional initiation region is introduced. By endogenous, is intended sequences both indigenous (i.e. natural to) the host animal and those present in the host animal as a result of an infectious disease, e.g. viral, prion, and the like.

A promoter from a gene expressed in brain tissue of the host animal is employed for varying the phenotype of the host animal. The transcriptional level should be sufficient to provide an amount of RNA capable of producing in a modified animal. By "modified animal" within the subject invention is meant an animal having a detectably different phenotype from a non-transformed animal of the same species, for example, one not having the transcriptional cassette including APP coding sequences in its genome. Preferably, the promoter is a strong promoter which drives a high level of expression of the APP coding sequence in brain tissue and/or which provides for many copies of the coding sequence in brain tissue.

The promoter preferably comprises a transcriptional initiation regulatory region and translational initiation regulatory region of untranslated 5' sequences, "ribosome binding sites", responsible for binding mRNA to ribosomes and translational initiation. The transcriptional initiation regulatory region may be composed of cis-acting subdomains which activate or repress transcription in response to binding of transacting factors present in varying amounts in different cells. It is preferred that all of the transcription and translational functional elements of the initiation control region are derived from or obtainable from the same gene. In some embodiments, the promoter is modified by the addition of sequences, such as enhancers, or deletions of non-essential and/or undesired sequences. By "obtainable" is intended a promoter having a DNA sequence sufficiently similar to that of a native promoter to provide for the desired specificity of transcription of a DNA sequence of interest. It includes natural and synthetic sequences as well as sequences which may be a combination of synthetic and natural sequences.

Tissue-specific transcription suggests that gene regulatory proteins are bound to enhancer sequences and other upstream promoter elements. By enhancer element ("enhancer") is intended a regulatory DNA sequence that is capable of activating transcription from a promoter linked to it with synthesis beginning at the normal RNA start site; which is capable of operating in both orientations (normal or flipped); and which functions even when moved either upstream or downstream from the promoter. Both enhancers and other upstream promoter elements bind sequences specific DNA binding proteins that mediate their effects. To identify the exact nucleotide sequences important for the function of the enhancer(s), and other upstream elements, fragments of the untranslated 5'-region encoding a protein expressed in a tissue of interest are screened for their capacity to bind nuclear proteins and for their ability to function with a heterologous promoter. Binding experiments with nuclear proteins from brain tissue can be used to determine the presence of enhancer and silencer sequences; the protein binding studies can be used to pinpoint specific nucleotide sequences that bind to a corresponding series of gene regulatory proteins.

The activity of each enhancer and other upstream promoter elements generally is present on a segment of DNA which may contain binding sites for multiple proteins. The binding sites can generally be dissected by preparing smaller mutated versions of the enhancer sequence joined to a reporter gene whose product is easily measured. The effect of each mutation on transcription can then be tested. Alternatively, fragments of this region can be prepared. Each of the mutated versions of the enhancer sequence or the fragments can be introduced into an appropriate host cell and the efficiency of expression of a reporter gene measured. Those nucleotides required for enhancer function in this test are then identified as binding sites for specific proteins by means of gel mobility shift and DNA foot printing studies. An alternate means of examining the capability of isolated fragments of the region upstream of the promoter to enhance expression of the reporter gene is to look for sub-domains of the upstream region that are able to enhance expression levels from a test promoter which comprises the TATA CAAT box but shows little or no detectable activity. A fragment of the 5' region is inserted in front of the test promoter in an expression cassette, and the effect on expression of the reporter gene evaluated. Of particular interest for brain-specific, copy number-dependent expression are regions capable of binding to nuclear proteins in the region up to about 20 kb from the mRNA start site of a brain-specific protein gene. Within this region, there may be several sub-domains of interest having the characteristics of brain specific enhancer elements which can be evaluated by using constructs.

A variety of promoter sequences an be used to control expression of APP coding sequences. These include the metallothionine (MT) promoter from which expression can be regulated through modulation of zinc and glucocorticoid hormone levels (Palmiter et al., *Nature* 300, 611–615 (1982)); the rat neuron specific enolase gene promoter (Forss-Petter, et al., *Neuron* 5; 197—197 (1990)); the human β-actin gene promoter (Ray, et al., *Genes and Development* (1991) 5:2265–2273); the human platelet derived growth factor B (PDGF-B) chain gene promoter (Sasahara, et al., *Cell* (1991) 64:217–227); the rat sodium channel gene promoter (Maue, et al., *Neuron* (1990) 4:223–231); the human copper-zinc superoxide dismutase gene promoter (Ceballos-Picot, et al., *Brain Res.* (1991) 552:198–214); and promoters for members of the mammalian POU-domain regulatory gene family (Xi et al., (1989) *Nature* 340:35–42). The POU-domain is the region of similarly between the four mammalian transcription factors Pit-1, Oct-1, Oct-2, and unc-86, and represents a portion of the DNA-binding domain. These promoters provide for expression specifically within the neurons of transgenic animals.

Of particular interest as a transcriptional initiation region is one derived from a prion protein gene which is functional in the brain of the host animal. Prion protein is implicated in the pathogenesis and transmission of Gerstmann-Straussler syndrome in humans and in scrapie, an equivalent non-human animal disease. Brain tissue serves as a source for nucleic acid for preparing the desired sequences. To identify a prion promotor having the desired characteristics, where a prion protein has been or is isolated, it is partially sequenced, so that a probe can be designated for identifying mRNA specific for prion protein. Sequences which hybridize to the cDNA are isolated, manipulated, and the 5' untranslated region associated with the coding region isolated and used in expression constructs to identify the transcriptional activity of the 5'- untranslated region. As appropriate, sequences can be amplified using PCR procedures known to those skilled in the art. In some instances, a probe is employed directly for screening a genomic library and identifying sequences which hybridize to the probe. The sequences will be manipulated as described above to identify untranslated region. Prion promoter sequences are described in Basler, et al. (1986), *Cell* 46:417–428 and Scott, et al. (1992) *Protein Science* 1:986–987.

The termination region which is employed primarily will be one of convenience, since the termination regions appear to be relatively interchangeable. The termination region may be native with the transcriptional initiation region, may be native with the DNA sequence of interest, or may be derived from another source. Convenient termination regions are available from the prion protein gene.

The expression cassette which is used in the subject invention includes promoter and enhancer sequences from a gene which is expressed in the brain and preferably which is expressed in a manner that is related to the number of such sequences incorporated into the chromosome, namely that higher transcription occurs with a larger number of transgene copies incorporated into the chromosomes, operably joined to an APP gene sequence and translational and transcriptional termination regions. Examples of promoter and enhancer sequences which are expressed in brain and which drive copy number dependent expression include the prion protein promoter, such as that described by Scott, et al., *Protein Science* (1992) 1:986–987, together with sequences upstream from the promoter, because in order to obtain copy number dependent expression, it generally is necessary to include a sufficiently large region of DNA controlling transcription so that it is large enough to be relatively unaffected by position effects. As an example, for the prion protein gene from hamster, approximately 20 kb of sequence upstream of the promoter can be used.

As an example of construction of a cosmid vector for use in the instant invention, components which are assembled, in the 5' to 3' direction, include promoter and enhancer sequences of the prion protein gene, the coding region of an APP gene sequence of interest and transcriptional and translational termination sequences operably attached to a cosmid vector for delivery of the DNA constructs into the pronuclei of mouse eggs for expression of an APP gene in brain tissue. The enhancer sequences may include a 20 kb region upstream of the prion protein promoter and may also include the noncoding exon 1 and the 10 kb intron downstream of exon 1 from the prion protein gene or can include the coding sequence for more than one APP protein as described in, for example, WO92/11276. Using molecular genetic techniques well known in the art, the promoter/enhancer region of the prion protein gene may be isolated from a mammalian genomic cosmid clone used to create transgenic mice which express prion protein. The coding sequence of an APP gene is inserted between the promoter/enhancer region and the termination sequences at unique restriction site or sites such that the coding sequence is translated in-frame. An APP protein in transgenic brain tissue introduced using a cosmid vector as described above may be confirmed to be at least two to four-fold that of endogenous levels. A major obstacle to the creation of a transgenic model of AD has been the inability to overexpress transgenic APP protein in the brain of the transgenic animal. In some cases, mRNA is well expressed, but the protein is poorly expressed. This indicates that the strength of promoters used may be adequate, but that protein translation may not be optimal. Poor translation may result from a weak translation initiation sequence. Accordingly, it may be necessary to include a translation initiation sequence wherein the positions at minus three and plus four relative to the initiation codon are A and G, respectively. See Table 1 below.

TABLE 1

Transgene Translation Initiation Sequence Optimization

| Transgene | Translation Initiation Sequence |
|---|---|
| | −3         +4 |
| Hacos.CS0HuAPP695-V717Imyc | GCGATGCTG |
| | (SEQ ID NO:1) |
| | (native human APP) |
| Hacos.CS1 | ACCATGCTG |
| | (SEQ ID NO:2) |
| Hacos.CS2 | ACCATGGTG |
| | (SEQ ID NO:3) |
| Hacos.MoAPP695-WT | ACGATGCTG |
| | (SEQ ID NO:4) |
| | (native mouse APP) |
| Hacos.MoPrP-P101L | ATCATGGCG |
| | (SEQ ID NO:5) |
| | (native mouse PrP) |

Any amyloid precursor protein sequence can be used to produce the transgenic animals of the invention. An APP protein sequence, as the term is used herein, means a sequence of the coding region of the APP gene which, when incorporated into the genome of the animal in multiple copies and expressed in the transgenic animal at supraendogenous levels, promotes a progressive neurologic disease in the transgenic animal. The neurologic disease is characterized by neurobehavioral disorder with gliosis and diminished glucose uptake and/or utilization in cortico-limbic brain structures. The coding sequence can be from a wild-type gene, or from a gene containing one or more mutations. The coding sequences can be a natural sequence or a synthetic sequence or a combination of natural and synthetic sequences. By mutant is intended any APP which has an amino acid sequence which differs from that of the native APP and includes substitutions, deletions, and the like. By wild-type APP is intended native APP as it occurs in the relevant host animal.

Native human APP is encoded by a single 400-kb gene comprised of 18 exons on chromosome 21. Alternative mRNA splicing gives rise to three APP isoforms. Two forms, APP751 and APP770 contain a Kunitz-protease inhibitor (KPI) region; the third, APP-695, lacks the KPI segment. Preferred sequences are those which are disease-linked. Examples of disease-linked mutations include a mutation at APP codon 693 (of APP770) linked to Dutch congophilic angiopathy (Levy, et al., (1990) *Science* 248:1124), a mutation in APP linked to familial AD, valine-isoleucine at codon 717 (of APP770) (Goate, et al., (1991) *Nature* 349:704–706), a mutation wherein the valine at codon 717 is replaced by phenylalanine or glycine (Chartier-Harlin, et al., (1991) *Nature* 353: 844–846; Murrell, et al., (1991) *Science* 254: 97–99); and in one family with both congophilic angiopathy and AD, a mutation wherein alanine is replaced by glycine at codon 692 (Hendriks, et al., (1992) *Nature Genetics* 1:218–221). In a Swedish kindred, a double mutation at codons 670 and 671, resulting in a substitution of the normal lysine-methionine dipeptide by asparagine-leucine was found (Mullan, et al., (1992) *Nature Genetics* 1:345–347). APP with K670N-M671L is reported to be associated with increased $A\beta1-40$ secretion (Citron et al. (1992) *Nature* 360: 672–674; Cai et al. (1993) *Science* 259: 514–516), while enhanced $A\beta1-42$ production is reported for APP with the V717I mutation (Cai et al. (1993), supra; Suzuki et al. (1994) *Science* 264: 1335–1340). To obtain animals with a progressive neurologic disease, while it can be used, it is unnecessary to use a coding sequence derived from an APP Gene with a mutation at the 717 locus; likewise, while it can be used, it also is unnecessary to use a coding sequence which includes a KPI region and/or splice sites within the coding region.

Table 2, below, lists some of the known amyloid precursor protein sequences, some of which are genetically linked to familial Alzheimer's disease.

TABLE 2[1]

Examples of APP Transgenes

| Translation Initiation | APP ORF Species | ORF Size (Codons) | Mutation |
|---|---|---|---|
| CS1 or CS2 | human, mouse or human/mouse chimeras | 695 & 751 or 770 | V717I V717G V717F VVM717/721/722IAV KM670/671NL770 A692G E693Q |

Figure 6:
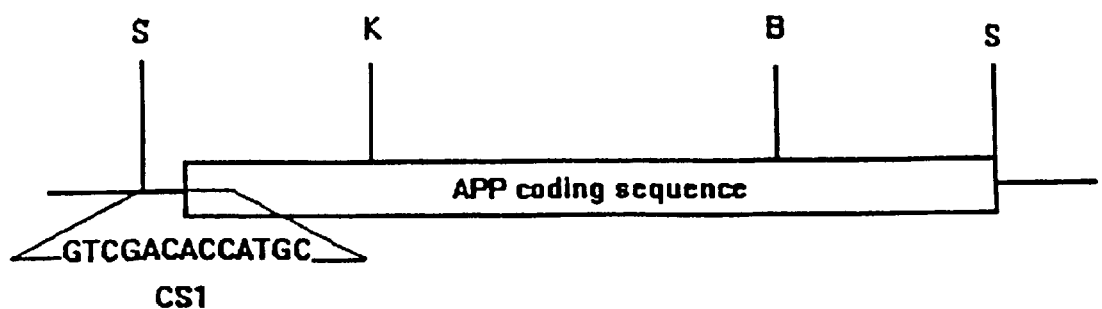
FIGS. 6 and 7 are diagrammatic representations of HuAPP sequences modified for strong translation initiation and flanking SalI restriction sites.
Figure 7:
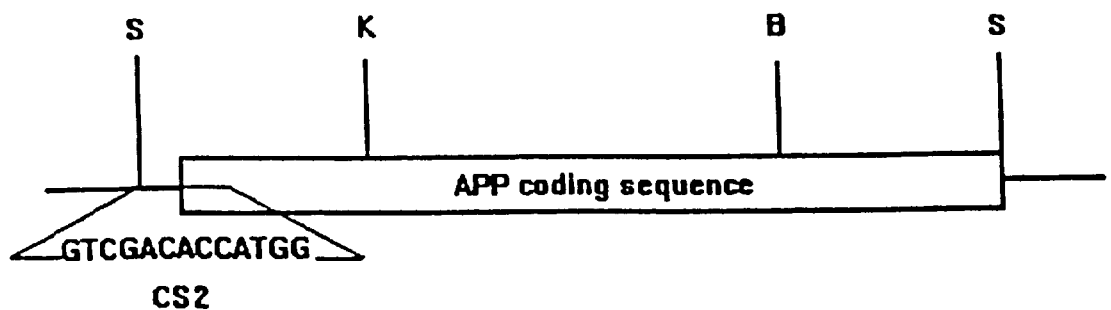

[1]The abbreviations used in Table 2 refer to the following: CS1 = translation initiation sequence as represented in FIG. 6; CS2 = translation initiation sequence as represented in FIG. 7; V = valine; I = isoleucine; G = glycine; F = phenylalanine; M = methionine; A = alanine; K = lysine; N = asparagine; L = leucine; E = glutamate; Q = glutamine; ORF = open reading frame; numeral in the Mutation column refers to the mutated codon based upon the APP770 numbering system.

Of particular interest are novel chimeric APP genes, in which human $A\beta$ sequences replace the $A\beta$ region of mouse APP. A158,5 is a 4-kDA peptide derived from APP. Examination of human (Hu), mouse (Mo), and chimeric (Mo/Hu) APP processing in mouse cell lines indicates that tangible differences are evident. HuAPP matures poorly in mouse cells, relative to Mo- or combination Mo/HuAPP. However, the human Aβ sequences promote the formation of soluble Aβ peptides that are normally produced. Mo/HuAPP chimeric protein matures more efficiently than HuAPP, and generates more soluble Aβ than MoAPP.

The animals used as a source of fertilized eggs cells or embryonic stem cells, the "host animal", can be any animal, although generally the preferred host animal is one which lends itself to multigenerational studies. Other preferred characteristics of the host animal include that it is naturally able to perform learning and memory tests, and that it does not die at such an early age when it expresses high levels of APP that there is insufficient time for observable behavioral and/or pathological changes to occur. Of particular interest are rodents including mice, such as mice of the FVB strain and crossed commercially available strains such as the (C57B6) x (SJL.F1) hybrid and the (Swiss Wester) x (C57B16/DBA-z.F1) hybrid. The latter parental line also is referred to as C57B16/D2. Other strains and cross-strains of animals can be evaluated using the techniques described herein for suitability for use as model for progressive neurologic diseases such as AD. In some instances, however, a primate, for example, a rhesus monkey may be desirable as the host animal, particularly for therapeutic testing.

Transgenic mammals are prepared in a number of ways. A transgenic organism is one that has an extra or exogenous fragment of DNA in its genome. In order to achieve stable inheritance of the extra or exogenous DNA fragment, the integration event must occur in a cell type that can give rise to functional germ cells, either sperm or oocytes. Two animal cell types that can form germ cells and into which DNA can be introduced readily are fertilized egg cells and embryonic stem cells. Embryonic stem (ES) cells can be returned from in vitro culture to a "host" embryo where they become incorporated into the developing animal and can give rise to transgenic cells in all tissues, including germ cells. The ES cells are transfected in culture and then the mutation is transmitted into the germline by injecting the cells into an embryo. The animals carrying mutated germ cells are then bred to produce transgenic offspring.

A preferred method for making the subject transgenic animals is by zygote injection. This method is described, for example, in U.S. Pat. No. 4,736,866. The method involved injecting DNA into a fertilized egg, or zygote, and then allowing the egg to develop in a pseudo-pregnant mother. The zygote can be obtained using male and female animals of the same strain or from male and female animals of different strains. The transgenic animal that is born is called a founder, and it is bred to produce more animals with the same DNA insertion. In this method of making transgenic animals, the new DNA typically randomly integrates into the genome by a non-homologous recombination event. One to many thousands of copies of the DNA may integrate at one site in the genome.

Generally, the DNA is injected into one of the pronuclei, usually the larger male pronucleus. The zygotes are then either transferred the same day, or cultured overnight to form 2-cell embryos and then transferred into the oviducts of pseudo-pregnant females. The animals born are screened for the presence of the desired integrated DNA. By a pseudo-pregnant female is intended a female in estrous who has mated with a vasectomized male; she is competent to received embryos but does not contain any fertilized eggs. Pseudo-pregnant females are important for making transgenic animals since they serve as the surrogate mother for embryos that have been injected with DNA or embryonic stem cells.

Putative founders are screened for presence of the transgene in several ways. Brain APP protein and APP expression are analyzed and the transgene copy number and/or level of expression are determined using methods known to those of skill in the art. Brain APP protein RNA expression, and transgene copy numbers are determined in weanling animals (4–5 weeks). When a promoter such as the prion protein gene promoter is used which is constituitively active in animals of weanling age and older, it is not expected that there will be changes in levels of transgenic APP RNA expression animals beyond weanling age. When a developmentally and/or tissue specific promoter is used, APP levels are monitored to determine expression levels with age. The transgenic animals also are observed for clinical changes. Examples of neurobehavioral disorders for evaluation are poor mating response, agitation, diminished exploratory behavior in a novel setting, inactivity, seizures and premature death.

It is a theory of the invention that parameters that can influence the phenotype of transgenic animals include the host strain, the primary structure of the APP and the levels of APP expression: the clinical changes observed in transgenic animals are a result of a combination of these factors. For a particular strain and a particular coding sequence, sufficient copies of an APP gene and/or a sufficient level of expression of a coding sequence derived from a particular APP gene which will result in observable clinical and/or behavioral symptoms, together with a measurable biochemical change in relevant brain structures can be determined empirically. By sufficient copies is intended that the total expression level from each construct is at least two-fold, preferably at least two to four-fold, more preferably five-fold or greater than that of an endogenous native gene, or that the overall copy number is such as to achieve this relative increase. In some instances, two to four copies of the gene, especially of a mutated disease-linked gene, are sufficient to achieve a desired relative increase in APP, while in other instances, particularly where a native gene is used, a larger copy number may be required. The copy number may range from five copies to more than 60 copies, depending on the species of APP expressed and the particular disease-associated mutations in the APP gene. As an example, the effective range of copy numbers in FVB/N mice for HuAPP695.TRImyc is approximately 20 to 75; for HuAPP695.SWE is approximately 30 to 50; and MoAPP.wt is greater than 25. In some instances a lower amount of APP is effective in producing a progressive neurologic disorder, particularly where the mutation in the APP occurs in the Aβ region, or just upstream of the Aβ region of the gene. Sufficient copies of a transgene therefore is that number which produces expression of APP at a level which results in a progressive neurologic disorder.

The founder animals can be used to produce stable lines of transgenic animals that superexpress APP, either mutant or native APP. For use of propagation, male founder mice are preferred. The animals are observed clinically. Analyses of transgene copy number (to exclude multiple transgene insertion sites), mRNA expression, protein expression, neuropathology, and glucose uptake in these animals are also performed. These studies provide information about the age of onset of illness, the duration of illness, the penetrance of the phenotype, the range of neuropathologic findings, regional brain dysfunction, and the dependence of phenotype upon levels of protein expression. Various changes in phenotype are of interest. These changes may include progressive neurologic disease in the cortico-limbic areas of the brain expressed within a short period of the time from birth;

increased levels of expression of an APP gene above endogenous expression levels and the development of a neurologic illness accompanied by premature death; gliosis and intracellular APP/Aβ accretions present in the hippocampus and cerebral cortex; progressive neurologic disease characterized by diminished exploratory/locomoter behavior, impaired performance on memory and learning tests, and diminished 2-deoxyglucose uptake/utilization and hypertrophic gliosis in the cortico-limbic regions on the brain.

The animals also are screened using a species appropriate neurobehavioral test. For example, studies of locomotor/exploratory behavior in mice is a standard means of assessing the neuropsychology (File and Wardill, (1975) *Psychopharmacologia* (Berl) 44:53–59; Loggi et al., (1991) *Pharmacol. Biochem. Behav.* 38:817–822). For example, for mice the "corner index" (CI) is used. This is a quick and simple neurobehavioral test to screen animals for evidence of brain pathology. The CI in transgenic mice which express mutant and wild-type APP is also measured. A low CI ($\leq 4$) correlates with high mutant APP transgene copy numbers, premature death, and neuropathologic findings. The CI exhibits a dosage dependent relationship to transgene copy number, which supports the validity of its use in accessing neurobehavioral sings in transgenic mice. The neuropathology of the animals also is evaluated. For rats, the Morris water maze test (described in Morris, (1984) *J. Neurosci. Meth.* 11:47), is used. A modified version of this test can be used with mice.

Brain regions known to be affected by the syndrome of interest are particularly reviewed for changes. When the disease of interest is Alzheimer's disease, the regions reviewed include the cortico-limbic region, including APP/Aβ excretions, gliosis, changes in glucose uptake and utilization and Aβ plaque formation. However, in strains of animals which are not long-lived, either naturally or when expressing high levels of APP, not all behavioral and/or pathological changes associated with a particular disease may be observed. As an example, transgenic FVB/N mice expressing high levels of APP tend not to develop detectable Aβ plaques, whereas longer lived C57B6/SJL F1 mice expressing identical transgenes do develop amyloid plaques which are readily detected with thioflavin S and Congo red. Immunologic studies of various brain regions also are used to detect transgene product.

The animals of the invention can be used as tester animals for materials of interest, e.g. antioxidants such as Vitamin E or lazaroids, thought to confer protection against the development of AD. An animal is treated with the material of interest, and a reduced incidence or delayed onset of neurologic disease, as compared to untreated animals, is detected as an indication of protection. The indices used preferably are those which can be detected in a live animal, such as changes in performance on learning and memory tests. The effectiveness can be confirmed by effects on pathological changes when the animal dies or is sacrificed. The animals further can be used as tester animals for materials of interest thought to improve or cure Alzheimer's disease. An animal with neurologic disease is treated with the material of interest, and a delayed death, or improvement in neurobehavior, gliosis, or glucose uptake/utilization, as compared to untreated animals with neurologic disease, is detected as an indication of amelioration or cure.

The animals of the invention can be used to test a material or situation, e.g. oxidants or head trauma, suspected of accelerating or provoking Alzheimer's disease, by exposing the animal to the material or situation and determining neurobehavioral decline, premature death, gliosis, and diminished glucose uptake/utilization as indicators of the capacity of the test material or situation to induce Alzheimer's disease. The method further can include testing of therapeutic agents by exposing animals to a material or situation suspected of provoking Alzheimer's disease and evaluating the effect of the therapeutic agent.

Careful characterization of the transgenic animals should lead to elucidation of the pathogenesis of progressive neurologic syndromes such as AD. The sequence of molecular events in mutant APP metabolism leading to disease can be studied. The animals also are useful for studying various proposed mechanisms of pathogenesis, including horizontal transmission of disease (Prusiner, et al. (1987) *Cell* 63, 673–86), oxidation and free-radical production (Blass and Gibson, (1991) *Rev. Neurol* (Paris) 147:513–525; Ames et al., (1993) *Proc. Nat'l. Acad. Sci. U.S.A.* 90:7915–7922), inflammation (McGeer et al. (1993) *Can. J. Neurol. Sci.* 18:376–379, Rogers et al. (1992) *Proc. Nat'l. Acad. Sci. U.S.A.* 89:10016–10020); neurotrophic factor deprivation (Perry, (1990) *Alzheimer's Disease and Associated Disorders* 4:1–13; Hefti and Schneider, (1991) *Clinical Neuropharmacology* 1:62–76); Koliatsoess et al., (1991) *Ann. Neurol.* 30:831–840), apolipoprotein E4 metabolism (Strittmatter et al., (1993) *Proc. Nat'l. Acad. Sci. U.S.A.* 90:1977–1981), and potassium channel dysfunction (Etcheberrigaray, et al., (1993) *Proc. Nat'l. Acad. Sci. U.S.A.* 90:8209–8213). Such knowledge would lead to better forms of treatment for neurologic disorders.

Other features and advantages of the invention will be apparent from the description of the preferred embodiments, and from the claims. The following examples are offered by way of illustration and not by way of limitation.

EXAMPLES

Example 1

PrP-HuAPP Transgene Construction

Figure 2:
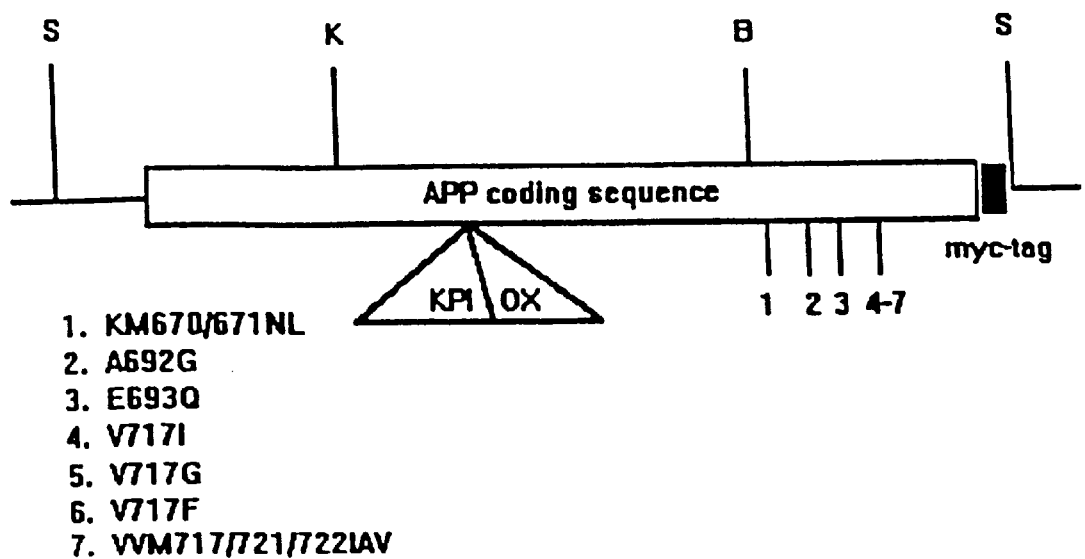
FIG. 2 is a diagrammatic representation of different APP sequences which can be expressed in transgenic animals (not exhaustive).

The human APP coding sequence was derived from a human cDNA (see Kang et al. (1987) *Nature* 325:733; Goldgabar et al., (1987); *Science* 235:877; Tanzi, et al., (1987) *Science* 235:880; and Robakis et al. (1987) *Proc. Nat. Acad. Sci. U.S.A.* 84:4190 and is illustrated in FIG. 1. It occurs in three splice forms which are derived from a gene located on chromosome 21 as described by Kitaguchi et al. (1988) *Nature* 331:530; Tanzi et al. (1988) *Nature* 331:528; and Ponte et al. (1988) *Nature* 331:525. FIG. 2 illustrates three features which may be incorporated into amyloid precursor protein sequences to produce the transgenic animals of the invention: (1) splice form variants which result from the presence or absence of the Kunitz protease inhibitor with or without the OX region; (2) amyloid precursor protein variants containing mutations which have been linked to illness in families with Alzheimer's disease as described by Goate (1991) *Nature* 349:704; Chartier-Harlin et al. (1991) *Nature* 353:844; Murell et al. (1991) *Science* 254:97; Hendriks et al. (1992) *Nature Genetics* 1:218; and Mullan et al. (1992) *Nature Genetics* 1:345, and families with congophilic angiopathy as described by Levy et al. (1990) *Science* 248:1124, and (3) a myc-tag at the carboxyl terminus which can be used to facilitate immunodetection of transgene products, but is preferably absent.

Figure 3:
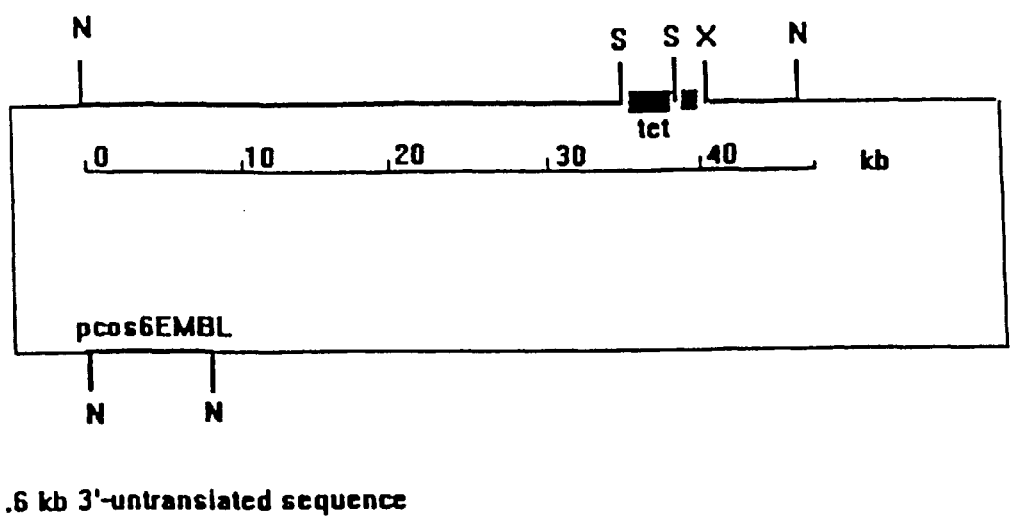
FIG. 3 is a diagrammatic representation of a hamster PrP cosmid vector with a tetracyclic-resistance sequence flanked by SalI sites replacing the PrP coding sequence.

The required hamster prion protein gene functions were provided by a hamster prion protein cosmid vector in which a tetracycline-resistance sequence flanked by SalI sites replaces the prion protein coding sequence, as described by Scott et al. (1992) *Protein Science* 1:986. The hamster prion protein cosmid vector is illustrated in FIG. 3. A 1.6 kb region of DNA in the 3'-untranslated region of the prion protein gene is indicated as a useful probe for detecting transgenes made from this cosmid.

Figure 4:
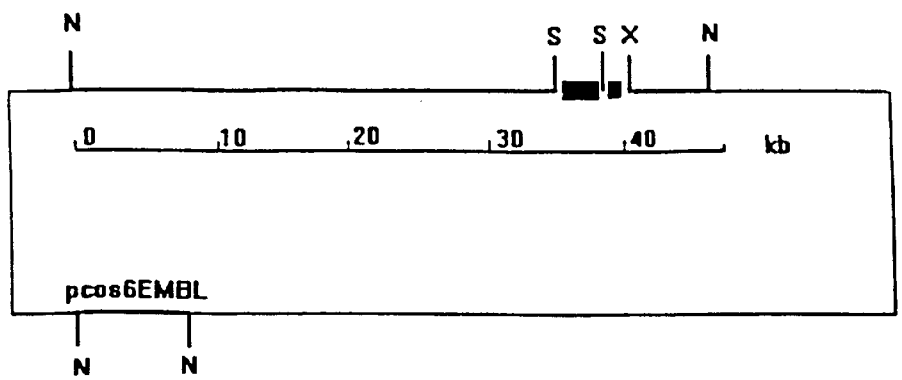
FIGS. 4 and 5 are diagrammatic representations of a hamster PrP cosmid vector fused with HuAPP sequences modified for strong translation initiation as illustrated in FIGS. 6 and 7.
Figure 5:
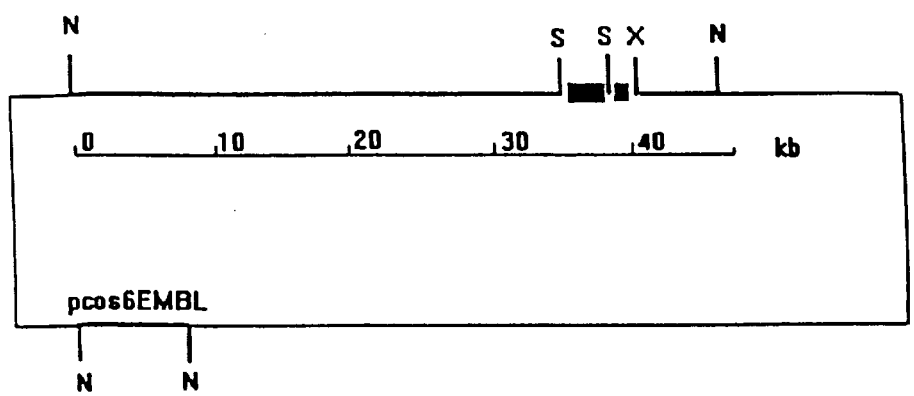

The APP sequences and cosmid were used to construct the two fusion gene constructions illustrated in FIGS. 4 and 5. The APP sequences were modified for strong translation initiation, represented by the abbreviations CS1 and CS2. The constructions were made by substituting the SalI to KPNI DNA sequence at the 5' end of the APP coding sequence for DNA sequences made using the polymerase chain reaction (PCR) and two sets of primers. For the CS1 APP sequence illustrated in FIG. 6, the primer set used was 5'-AAGTCGACACCATGCTGCCCGGTTTGGCACT-3' (SEQ ID NO:6) and 5'-AAGGTACC TCCC AGCGCCCGAGCC-3' (SEQ ID NO:6). For the CS2 APP sequence illustrated in FIG. 7, the primer set used was 5'-AAAAAAGTCGACACCATGGTGCCCGGTTT GGCACT-3' (SEQ ID NO:8) and 5'-AAGG TACCTCCAGCGCCCGAGCC-3' (SEQ ID NO:9).

Procedures were the conventional techniques described in Maniatis et al. (1982) *Molecular Cloning: A Laboratory Manual* (Cold Spring Harbor Laboratory) and the polymerase chain reaction (PCR) described in Saiki et al. (1988) *Science* 239:487. The restriction sites shown in FIGS. 1–7 are SalI (S), KpnI (K), BglII (B), XhoI (X) and NotI (N). The location of the PCR oligomers used for detecting fusion constructs in animals are indicated by A and P in FIG. 8. Each PCR fragment synthesized for the constructions was sequenced. The PCR fragments selected for use in the constructions were free of unintended mutations.

The above PrP-APP cosmids were digested with NotI which releases the PrP-APP fusion gene from the pcos6EMBL vector illustrated in FIGS. 3–5. The Prp-APP fusion gene was isolated after size fractionation on an agarose gel and electroeluted. The PrP-APP fusion gene was further purified in a series of organic extractions, including phenol-chloroform, chloroform, and butanol, and precipitated in ammonium acetate and ethanol. Prior to embryo injection, the PrP-APP fusion gene was dissolved in 10 mM Tris-Cl (pH 8.0) to a final concentration of 3–4 µg/ml.

Example 2

Production of Transgenic Mice Containing PrP-HuAPP Transgene (APP Sequence VVM717/721/722IAV)

Each PrP-APP fusion gene was separately injected into fertilized one-cell mouse eggs (Hogan et al. (1986) *Manipulating the Mouse Embryo: A Laboratory Manual*, Cold Spring Harbor Press, N.Y.; also see U.S. Pat. No. 4,736,866). Embryo donors and fertile studs were inbred FVB mice obtained from the National Cancer Institute (NCI); this resulted in the integration of between 1 and 128 copies of PrP-APP fusion genes into the genomes of the mice which developed to term. The injected eggs were transferred to pseudo-pregnant foster females as described in Wagner et al. (1981) *Proc. Nat'l. Acad. Sci. U.S.A.* 78:5016. Mice were housed in an environmentally controlled facility maintained on a 10 hour dark: 14 hour light cycle. The eggs in the foster females were allowed to develop to term.

Example 3

Analysis of VVM717/721/722IAV Transgenic Mice

Figure 8:
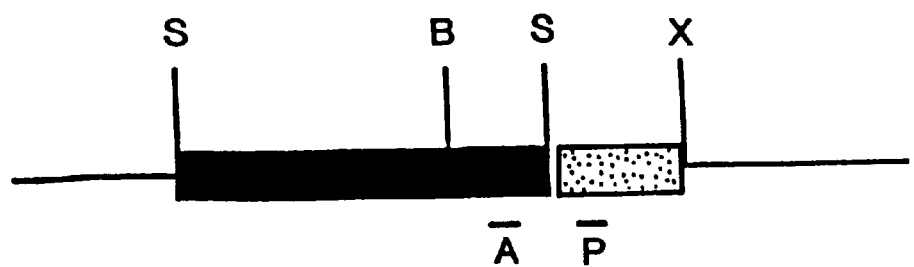
FIG. 8 is a diagrammatic representation of PCR primers which can be used to detect transgenes.
Figure 10A:
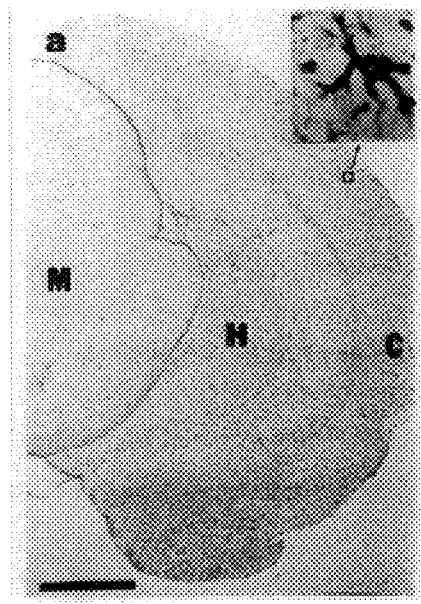
FIG. 10A, Tg(HuAPP695.TRImyc) 1118–334 exhibiting behavioral abnormalities (agitation and low corner index scores) at 144 days of age, sacrificed at 206 days.
Figure 10B:
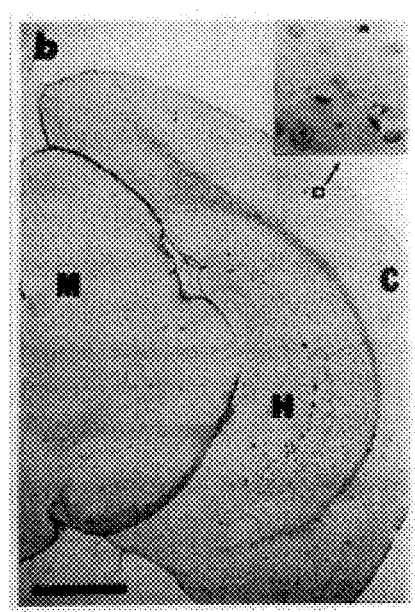
FIG. 10B, non-Transgenic litter mate of Tg1118–334 without behavioral abnormalities, age 206 days.
Figure 10C:
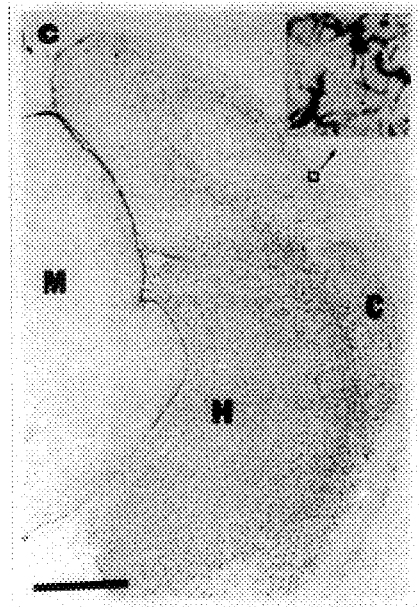
FIG. 10C, non-Transgenic #4565 exhibiting behavioral abnormalities (inactivity and low corner index scores) at 324 days of age, sacrificed at 334 days.
Figure 10D:
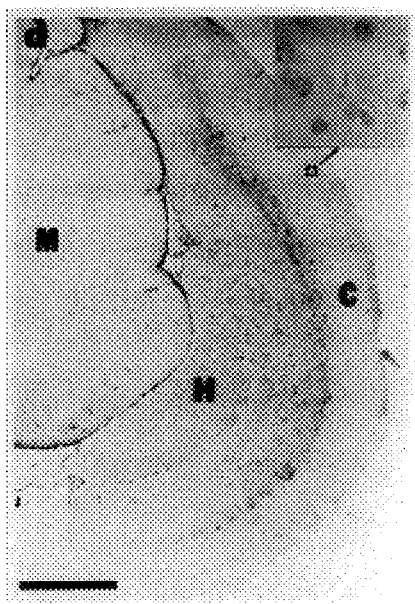
FIG. 10D, non-Transgenic litter mate of #4565 without behavioral abnormalities, age 334 days.

At four weeks of age, each pup born was analyzed in a PCR reaction using DNA-taken from the tail. In each case, tail DNA was used as a template for a PCR reaction using the probes indicated at FIG. 8. The DNA for analysis was extracted from the tail by the method described in Hanley and Merlie (1991) *Biotechniques* 10:56. One µl of the tail DNA preparation (approximately 1 µg of DNA) was used to amplify a transgene specific DNA fragment in a 25Z1 PCR reaction containing primers A and P as illustrated in FIG. 8.

The PCR reactions indicated that 15 founder mice had retained an injected PrP-APP fusion gene. The APP sequence in these animals contained the VVM717/721/722IAV mutation and the myc-tag, but lacked the KPI/OX regions represented in FIG. 2. To determine transgene copy number, denatured DNA in an exponentially diluted series was probed with a 1.6 kilobase (KB) radiolabelled segment of DNA from the 3'-untranslated region of the hamster PrP gene as illustrated in FIG. 3. Among the founder mice with the highest transgene copy numbers (approximately 100 or more), two founder mice failed to breed, and a third founder sired offspring, which in turn failed to breed. Thus, the 15 founder mice yielded 12 lines of transgenic offspring. A catalog of transgenic founders with APP transgenes is shown in Table 3.

The founder animals were mated to uninjected animals and the DNA of the resulting 12 lines of transgenic offspring analyzed: this analysis indicated that in every case the injected genes were transmitted through the germline.

TABLE 3

Catalog of Transgenic Founders with APP Transgenes

| Animal ID | Transgene | Transgene Copy # | Protein Level | Status |
|---|---|---|---|---|
| Tg425L | Hacos.CS0HuAPP695-V717Imyc | 1 | Not detectable | Sac'd |
| Tg466M | Hacos.CS0HuAPP695-WTmyc | 32–64 | 1.5–2X | Alive |
| Tg1056L | Hacos.CS1HuAPP695-V717Imyc | 16 | | Alive |
| TG1057H | Hacos.CS1HuAPP695-V717Imyc | 64–128 | | Dead |
| Tg1064L | Hacos.CS1HuAPP695-V717Imyc | 8 | | Alive |
| Tg1072L | Hacos.CS2HuAPP695-V717Imyc | 1 | | Alive |
| Tg1073L | Hacos.CS2HuAPP695-V717Imyc | 1 | | Alive |
| Tg1118M | Hacos.CS1HuAPP695-V717Imyc | 32–64 | | Alive |
| Tg1119L | Hacos.CS1HuAPP695-V717Imyc | 1 | | Alive |
| Tg1123L | Hacos.CS1HuAPP695-V717Imyc | 1 | | Alive |
| Tg1125L | Hacos.CS1HuAPP695-V717Imyc | 8–16 | | Alive |
| Tg1130H | Hacos.CS1HuAPP695-V717Imyc | 64–128 | | Sick |
| Tg1135H | Hacos.CS2HuAPP695-V717Imyc | 64–128 | | Dead |
| Tg1138H | Hacos.CS2HuAPP695-V717Imyc | 64–128 | | Dead |
| Tg1140M | Hacos.CS2HuAPP695-V717Imyc | 32–64 | | Alive |

Six founder animals harbored >20 copies of the PrP-APP fusion genes. All six developed a neurologic disease characterized by progressively diminishing exploratory/locomotor behavior and premature death by five months of age. In contrast, none of nine founder animals harboring <20 copies of the PrP-APP fusion genes have developed the neurologic disease within the first five months of age. The neurologic dysfunction was transmitted to succeeding generations in an autosomal dominant fashion.

Expression of the newly acquired PrP-APP fusion genes in tissue was determined by Western blot analysis using a monoclonal antibody, 6E10, raised to the first 17 residues of the human Aβ peptide (Kim, et al. (1990) *Neuroscience Research Communicating* 7:113–122). The fusion gene product was detected in the brain, spinal cord, skeletal muscle, heart, and, minimally, lung. It was not detected in the liver, spleen, kidney, or testis.

Expression of the PrP-APP fusion gene in brain tissue was quantitated by immunodot blot analysis. Relative APP expression in brain tissue was compared in transgenic and non-transgenic mice in an exponentially diluted series and reacted with antibody recognizing the 15 residues at the carboxyl terminus of APP, CT15, which recognizes both mouse and human APP (Sisodia, et al (1993) *J. Neurosciences* 13:3136–3142). The total APP protein in lines of mice which developed the neurologic disease was at least 300% of endogenous levels. Where expression was less than 300%, animals did not develop neurologic disease.

To obtain an index of brain function in affected transgenic mice, glucose utilization was regionally determined using a modification of the Sokoloff method described by Chmielowska et al. (1986) *Exp. Brain Res.* 63:607, which allows glucose uptake/metabolism in the mouse to be measured. Regional 2-deoxyglucose concentrations determined densitometrically were normalized to the cerebellum, a region devoid of pathology. Results in transgenic mice revealed significant reductions in glucose utilization of 20–30% in the hippocampus, amygdala, and some regions of the cerebral cortex as compared to age-matched non-transgenic littermates.

Example 4

Analysis of Synthesis and Processing In Vitro

The synthesis and processing of the VVM717/721/722IAV mutant in cultured cells was examined to determine the effects of these mutations on disease development. The wild-type HuAPP695myc and mutant cDNA genes were cloned into the expression vector pEF-BOS (Osaka Bioscience Institute, Osaka, Japan), then transiently transfected into mouse neuroblastoma cells, which were then continuously labeled with [$^{35}$S]methionine for 4 hours. Labeled APP molecules were immunoprecipitated with the monoclonal antibody 22C11 (Weidemann, et al. (1989) *Cells* 57:115–126). In extracts of cells, labeled APP molecules of the appropriate size were detected in similar levels. Media from these cultures was examined for the presence of soluble APP fragments using mAb 6E10 and mAb 4G8 (Kim, et al. (1990) supra.). Both of these antibodies recognize the Aβ region of human APP. The mAb 6E10 recognizes sequences in Aβ between Aβ1–17, while mAb 4G8 recognizes sequences between Aβ1–28. The sequence of Aβ17–28 is identical to mouse Aβ and thus 4G8 cannot distinguish human and mouse APP. The media of cultures transfected with either gene contained a large ectodomain fragment of APP which is routinely observed.

One of the more recent discoveries relevant to the processing of APP has been the detection of soluble Aβ 1–40 fragments in the medium of cultured cells that express HuAPP. The Aβ fragments resemble peptides found in AD amyloid plaque lesions. Thus, it appears that APP is normally processed into amyloidogenic fragments. Furthermore, mutations linked to AD have been shown to alter the processing of APP to favor the production of soluble Aβ. To determine whether the VVM717/721/722IAV mutations affected the processing of APP, the culture medium was examined for small Aβ-containing APP peptides. An Aβ peptide fragment that was immunopurified by mAb 6E10 was prevalent in the media of cells transfected with the mutant sequence. Similarly, the mAb 4G8 detected increased levels of Aβ peptide in the medium of cultures containing the mutant.

An examination of cell extracts for accumulated APP fragments detected increased levels of a 20 kDa APP peptide fragment after immunoprecipitation with anti-myc polyclonal antiserum in cells expressing the mutant (FIG. 5C, line 3). Mutations generated in mutant HuAPP695myc affect the processing of the resultant APP product to generate increased levels of soluble Aβ, and an intracellular C-terminal fragment of APP that is of sufficient length to include the Aβ region. Thus, the phenotype of animals created with the mutant APP is much like that reported for humans expressing a mutant human APP gene that encodes mutations found in a Swedish kindred of AD. To date no investigators have reported increased production of Aβ as a result of expression of HuAPP that encodes only the V642I AD-linked mutation (Golde et al., (1993), *Neuroscience Abstract* 19:431, 182.7). However, this mutation appears to cause a change in the length of the soluble Aβ derivative, increasing it to Aβ1–42. Thus it appears that the VVM717/721/722IAV mutations are the primary cause of the increased production of soluble Aβ. Studies of Aβ fibrillogenesis suggest that longer Aβ peptides are more amyloidogenic.

Example 5

Comparison of Processing of Human and Mouse APP in Mouse Cells

Chimeric APP transgenes composed of mouse APP695 and human Aβ sequences were prepared and their processing evaluated. It is a hypothesis of the invention that there are differences in the way mouse and human APP are processed in mice. To construct humanized MoAPP cDNA, a MoAPP gene was cloned and mutated to make it compatible with the cosSHaPrP.535 vector. Mouse cDNA was isolated by reverse transcriptase-polymerase chain reaction (RTPCR), and PCR primers included XhoI sites at the 5' and 3' ends for cloning purposes. To remove an internal XhoI site in the mouse cDNA, an additional primer was included that spanned the internal XhoI site (codon 397) and contained a single base substitution that eliminated the XhoI site but preserved the correct amino acid sequence. The PCR product was subsequently sequenced to verify that unwanted mutations were not created in the PCR.

The Aβ region in HuAPP and MoAPP differs by three amino acid residues, which could affect the amyloidogenic potential of the transgene product. To humanize the mouse Aβ region, a segment of the HuAPP gene that encompassed the Aβ region was amplified by PCR using primers that include a sense primer that encompassed the BglII site at codon 590 of HuAPP695 and an antisense primer that contained two point mutations creating a NarI site at codon 626 (a cognate NarI site is found in the MoAPP cDNA), while maintaining the amino acid sequence (Table 4, primers 1 and 2). This PCR product was digested with BglII and NarI and then cloned into the BglII and NarI sites of the MoAPP cDNA.

The chimeric (Mo/HuAPP) cDNA was sequenced across the BglII and NarI sites to verify that this region now contained human Aβ sequences and to verify that no other unwanted mutations were generated. To verify that this recombinant cDNA could be expressed into full-length protein, DNA was cloned into a modified pEFBOS vector. The pEFBOS vector contains the promoter element, first exon, first intron, and part of the second exon of the mammalian elongation factor 2 along with an SV40 origin of replication, permitting the replication of vectors and the high expression of genes in COS-1 cells. COS-1 cells were transfected with pEF-BOSMo/HuAPP695 and cell extracts were analyzed by immunoblotting. CT15 recognized a full-length Mo/HuAPP polypeptide, whereas immunostaining with monoclonal antibody 6E10 verified that the humanized identification as Aβ1–40. In cells transfected with MoAPP, a fragment that is of a size and character consistent with identification as Aβ17–40 was detected. The Aβ17–40 fragment is thought to arise after membranal cleavage of APP by the putative secretase, which cleaves between Aβ16 and −17. Only the Hu- and MoHuAPP derived Aβ1–40 peptides were recognized by mAb6E10 as expected. While MoAPP appeared to give rise to relatively equal amounts of Aβ1–40 and Aβ17–40, HuAPP and Mo/HuAPP were preferentially cleaved to generate only Aβ1–40. These results suggest that sequences differences within the human Aβ domain influence APP proteolytic cleavage.

TABLE 4

Primers Used In Constructing Recombinant APP Genes

| Primer | Sense | Sequence | Cloning Sites | Codon Mutation |
|---|---|---|---|---|
| 1 | + | CCGAGATCTCTGAAGTGAAGATGGATG (SEQ ID NO:10) | Bgl II | none |
| 2 | − | AAGCTTGGCGCCTTTGTTTGAACCCAC (SEQ ID NO:11) | Nar I | none |
| 3 | + | CCGAGATCTCTGAAGTGAATCTGGATGC (SEQ ID NO:12) | Bgl II | FAD (N595,L596) | mouse cDNA product did indeed encode human Aβ sequences.

To generate chimeric Mo/HuAPP cDNA that encodes a double mutation linked to an early-onset AD, a PCR-based approach similar to that outlined above using primers 2 and 3 (Table 4) was employed. The template for the reactions was a cloned copy of Mo/HuAPP695. The mutated chimeric gene was sequenced across the BglII and NarI sites to verify the presence of mutations and to be certain that no unwanted mutations existed in the transgene. The mutant Mo/HuAPP cDNA was cloned into pEFBOS and transfected into COS-1 cells to determine whether APP polypeptides were synthesized. An APP polypeptide of the predicted size reacted with both CT15 and 6E10 antibodies.

An examination of the synthesis and processing of Mo-, Hu-, and Mo/HuAPP in mouse N2a cells has surprisingly revealed discernible differences. What is evident is that a greater percentage of MoAPP is cleaved to generate a soluble ectodomain fragment than is HuAPP. The ratio of cell-associated versus soluble MoAPP is approximately 1 to 5, while 3 times more of the HuAPP is cell-associated than is soluble. The percentage of Mo/HuAPP695 that is cleaved to generate soluble ectofragments appears to fall between that of Mo- and HuAPP as the ratio of cell-associated to soluble Mo/HuAPP approaches 1 to 1. The majority of soluble APP ectofragments appear to arise from a cleavage event within AD at the cell surface; the differences in the ratio of cell-associated APP versus soluble ectofragments indicate differences in the maturation of the polypeptides. Specifically, the majority of MoAPP reaches the cell surface and is cleaved by a secretase. In contrast, HuAPP may not reach the cell surface as efficiently, thus precluding secretase cleavage. The Mo/HuAPP polypeptide appears to be intermediate between Mo and HuAPP. Alternatively, it is possible that sequences within the Aβ domain influence the efficiency of secretase cleavage.

In addition to differences in the production of soluble APP ectofragments, differences in the level of soluble Aβ peptides were noted. All three proteins gave rise to soluble Aβ peptides that were of a size and character consistent with Example 6

Comparison of Normal Aged Mice and Transgenic Mice

Transgene Construction

The PrP-APP transgenes were generated as described in Example 1 by replacing a SalI-flanked tetracycline resistance sequence in a hamster PrP cosmid vector (Scott et al., (1992), supra), with SalI-flanked human and mouse APP coding sequences. Transgenic mice were prepared using one of six different PrP/APP chimeric transgenes: murine wild-type APP695 (MoAPP695.WT); human APP695 containing two mutations at K670N and M671L (APP770 numbering) (HuAPP695.SWE); human APP695 containing two mutation at M670N and K671L (APP770 numbering) (HuAPP695.SWE); human APP695 containing a mutation at E693Q (HuAPP695.DUT); human APP770 with K670N and M671L (HuAPP770.SWE); human APP695 with a triple mutation at V717I, V721IA, and M722V with a 3'-myc tag (HuAPP695.TRImyc); and human wild-type APP695 with a 3'-myc tag (HuAPP695.WTmyc). The SC1HuAPP695.SWE, CS1HuAPP770.SWE, CS1HuAPP695.TRImyc and CS2HuAPP695.TRImyc APP sequences were modified for strong translation initiation.

Like the Swedish mutation, triple V7171I, V721A and M722V mutations in the transmembrane domain of APP enhance secretion of Aβ by five-fold in cultured cells. The 3'-myc tag, a 12 codon segment of the c-myc proto-oncogene, was shown in cultured cells to facilitate immunodetection of transfection products (Wong and Cleveland, (1990) The Journal of Cell Biology 111, 1987–2003). In Tg(HuAPP695.WTmyc) and Tg(HuAPP695.TRImyc) mice the myc-tag was not as clearly detectable in Western blots and histologic samples as HuAPP reacted with human-specific APP antibodies. The myc-tag exerted no apparent effect on the phenotype, since Tg(HuAPP695.SWE, Tg(HuAPP770.SWE), and Tg(HuAPP695.DUT) mice lacking the myc-tag develop the same clinical and pathologic abnormalities. The constructions were made by substituting the SalI to KpnI DNA sequence at the 5' end of the APP coding sequence for DNA sequences made using the polymerase chain reaction (PCR) and two sets of primers. For the CS1 APP sequence, the primer set used was 5'-AAGTCGACACCATGCTGCCCGGTTTGGCACT-3' and 5'AAGGTACCTCCCAGCGCCCGAGCC-3'. For the CS2 APP sequence, the primer set used was 5'AAAAAAGTCGACACCATGGTGCCCGGTTTGGC ACT-3' (SEQ ID NO:8) and 5'-AAGGTACC TCCAGCGCCCGAGCC-3' (SEQ ID NO:7). The HuAPP mutations were made using standard methods of site-directed mutagenesis. Each PCR fragment synthesized for the constructions was sequenced. The PCR fragments selected for use in the constructions were free of unintended mutations. The PrP-APP cosmids were digested with NotI (which releases the PrP-APP fusion gene from the pcos6EMBL vector). The Prp-APP fusion genes were isolated after size fractionation on an agarose gel and electroeluted. The PrP-APP fusion gene was further purified with organic solvents, and precipitated in ammonium acetate and ethanol. The PrP-APP fusion genes were dissolved in 10 mM Tris-Cl (pH 8.0) to a final concentration of 3–4 µg/ml prior to embryo injection. 1503: 5'-CTGACCACTCGACCAGGTTCTGGGT-3' (SEQ ID NO:13) and 1502: 5'-GTGGATAACCCCTCCCCCA GCCTAGACCA-3' (SEQ ID NO:14), located in the 3' region of APP and the 3'-untranslated region of PrP, respectively. The 1503 primer recognizes a region which is homologous in mouse and human APP, and can therefore be used to detect both PrP-MoAPP and PrP-HuAPP DNA. Using primers 1502 and 1502: 5'-AAGCGGCCAAAGCCTGGAGGGTGGAACA-3' (SEQ ID NO:15), a parallel PCR reaction amplifying a fragment of murine PrP was performed as a positive control.

Transgene copy number analysis was performed using 5 µg denatured purified tail DNA baked onto nitrocellulose and hybridized to a radiolabelled 1.3 kb SalI-XhoI DNA fragment encoding a segment of the hamster PrP 3'-untranslated region located in the DNA sequence at the 5' end of the APP coding sequence for DNA sequences made using the polymerase chain reaction (PCR) and the two sets of primers described in Example 1. The HuAPP mutation were made using standard methods of site-directed mutagenesis. Each PCR fragment synthesized for the constructions was sequenced. The PCR fragments selected for use in the construction were free of unintended mutations. The PrP-APP cosmids were digested with NotI and the Prp-APP fusion genes were isolated after size fractionation on an agarose gel and electroeluted and further purifies as described in Example 1. The PrP-APP fusion genes were dissolved in 10 mM Tris-Cl (pH8.0) to a final concentration of 3–4 µg/ml prior to embryo injection.

Transgenic Mouse Generation and Screening

Transgenic lines were initiated by microinjection of single-cell mouse embryos as described (Hogan et al., (1986) supra). Embryo donors and fertile studs were inbred FVB mice obtained from the National Cancer Institute (NCI). Post-weaning tail biopsy DNA was generated as described (Hanley and Merlie, (1991) Biotechniques 10, 56). One microliter of the unpurified DNA was used in a 25 µl PCR reaction. To detect PrP-APP fusion DNA, the PrP-APP fusion DNA was amplified using the polymerase chain reaction with a pair of oligomer primers, 1503: 5'-CTGACCACTCGACCAGGTTCTGGGT-3' (SEQ ID NO:13) and 1502: 5'-GTGGATAACCCCTCCCCC AGCCTAGACCA-3' (SEQ ID NO:14), located in the 3' region of APP and the 3'-untranslated region of PrP, respectively. The 1503 primer recognizes a region which is homologous in mouse and human APP, and could therefore be used to detect both PrP-MoAPP and PrP-HuAPP DNA.

Using primers 1502 and 1501: 5'AAGCGGCCAAAGCCTGGAGGGTGGAACA-3' (SEQ ID NO:15), a parallel PCR reaction amplifying a fragment of murine PrP was performed as a positive control.

Transgene copy number analysis was performed using 5 µg denatured purified tail DNA baked onto nitrocellulose and hybridized to a radiolabelled 1.3 kb SalI-XhoI DNA fragment encoding a segment of the hamster PrP 3'-untranslated region located in the hamster PrP cosmid vector (Scott, et al., (1992) supra). After two high-stringency washes and exposure to radiosensitive film, the relative intensities of signals from genomic DNAs to transgenic mice and hamsters were compared using a phosphorimager to obtain transgene copy numbers relative to diploid hamster genomic DNA.

Analysis of Transgene Expression

APP transgene product expression was examined in progeny of transgenic founders sacrificed at one to four months of age. Quantitative immunoblotting of extracts from brain homogenates was carried out in parallel with extract prepared from age-matched nontransgenic littermates. 20% (w/v) homogenates of brain tissues were prepared in TNE (50 mM Tris-Cl pH 8.0, 150 mM NaCl, 5 mM EDTA with 2% PMSF) buffer, using a hand-held polytron. Homogenates were diluted with an equal volume of TNE 1% N40, 1% deoxycholate, 0.4% SDS and sonicated in a bath sonicator until all viscosity was lost. Homogenates were then boiled for 10 minutes and centrifuged at 10,000×g for 10 minutes.

Figure 11A:
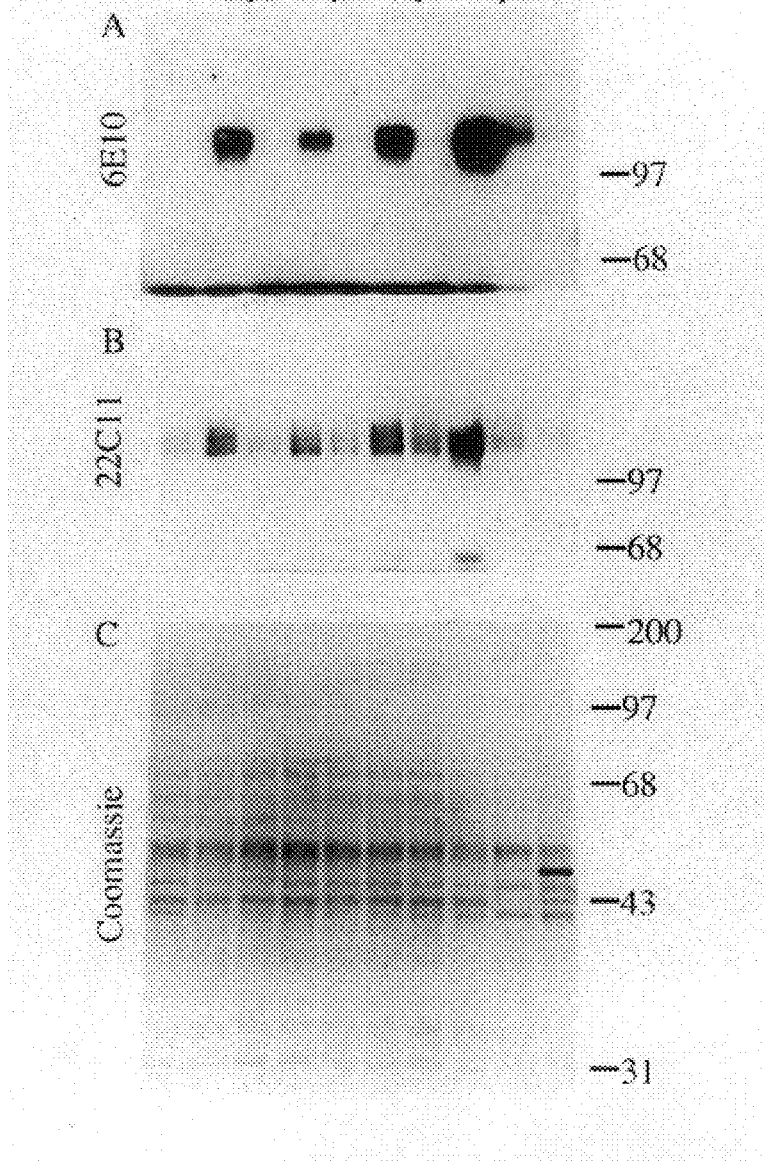
FIG. 11 shows transgenic HuAPP protein expression in brain tissue. HuAPP protein expression was measured in a semi-quantitative fashion in four lines of Transgenic mice, Tg(HuAPP695.WTmyc)466, Tg(HuAPP695.TRImyc)1056, Tg(HuAPP695.TRImyc) 1118, Tg(HuAPP695.TRImyc) 1130H, harboring 40, 7, 21 and 74 transgene copy numbers, respectively. Relative levels of transgenic compared with endogenous brain MoAPP were examined by immunoblot analysis with two polyclonal APP antisera, CT15 (FIG. 11A) and anti-GID (FIG. 11A), and a monoclonal antibody, 22C11 (FIG. 11B). CT15 antiserum recognized the C-terminal 15 amino acids of APP, a region in which mouse and human APP are homologous. GID antiserum recognizes an epitope 175–186 residues from the amino terminus of APP695, a region in which mouse and human APP are identical. Equivalent amounts of protein from detergent-extracted brain homogenates of non-Transgenic and Transgenic litter mates were immunoblotted in parallel. Primary antibody was revealed by $^{125}$I-protein A. For monoclonal antibodies, blots were first incubated with rabbit antiserum to mouse IgG. The amount of bound $^{125}$I-protein A was quantified using a phosphorimager, demonstrating a direct relationship between transgene copy number and transgene product expression. To measure the level of HuAPP specifically, brain homogenates were probed with 6E10 antibody raised against residues 1–17 of human Aβ (Kim, et al. (1990) *Neuroscience Research Communications*, 7, 113–122).
FIG. 11C shows the regional expression of HuAPP in the brain. The relative amount of HuAPP in 10% w/v homogenates of various tissues was specifically detected in Tg(HuAPP695.TRImyc)1130H mice using 6E10 antibody. Equivalent amounts of protein were immunoblotted in each lane. Lanes 1, telencephalon; 2, diencephalon; 3, mesencephalon; 4, pons; 5, cerebellum; 6, medulla; 7, spinal cord. The highest HuAPP level, in the telencephalon, was approximately twice that of the cerebellum.
Figure 11B:
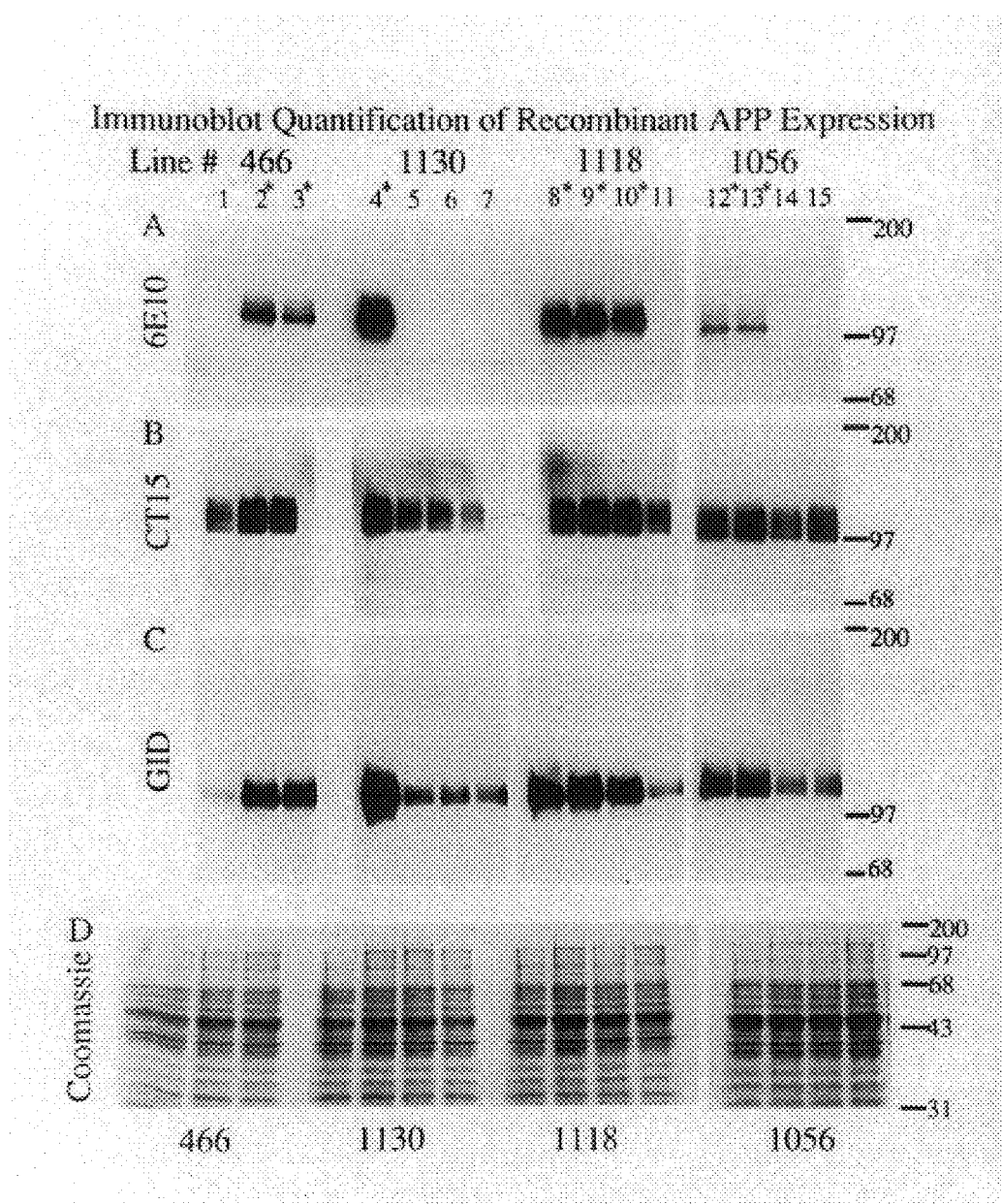
Figure 11C:
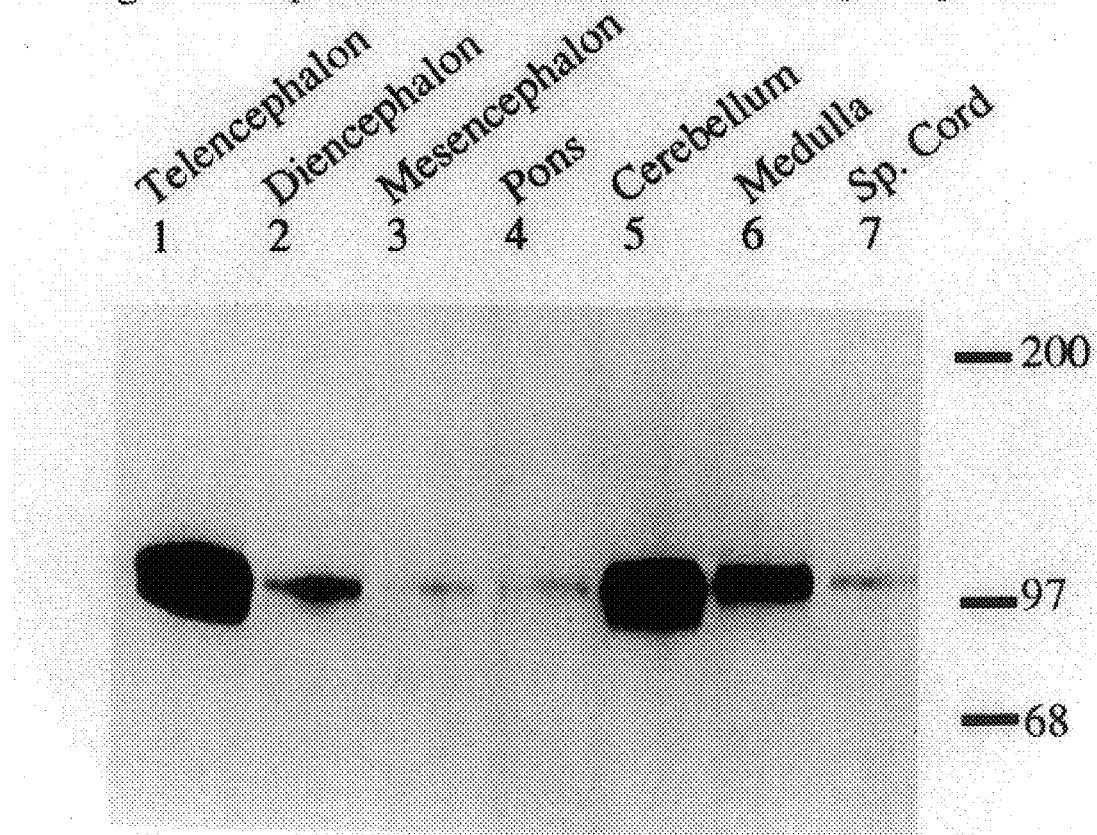
Figure 12:
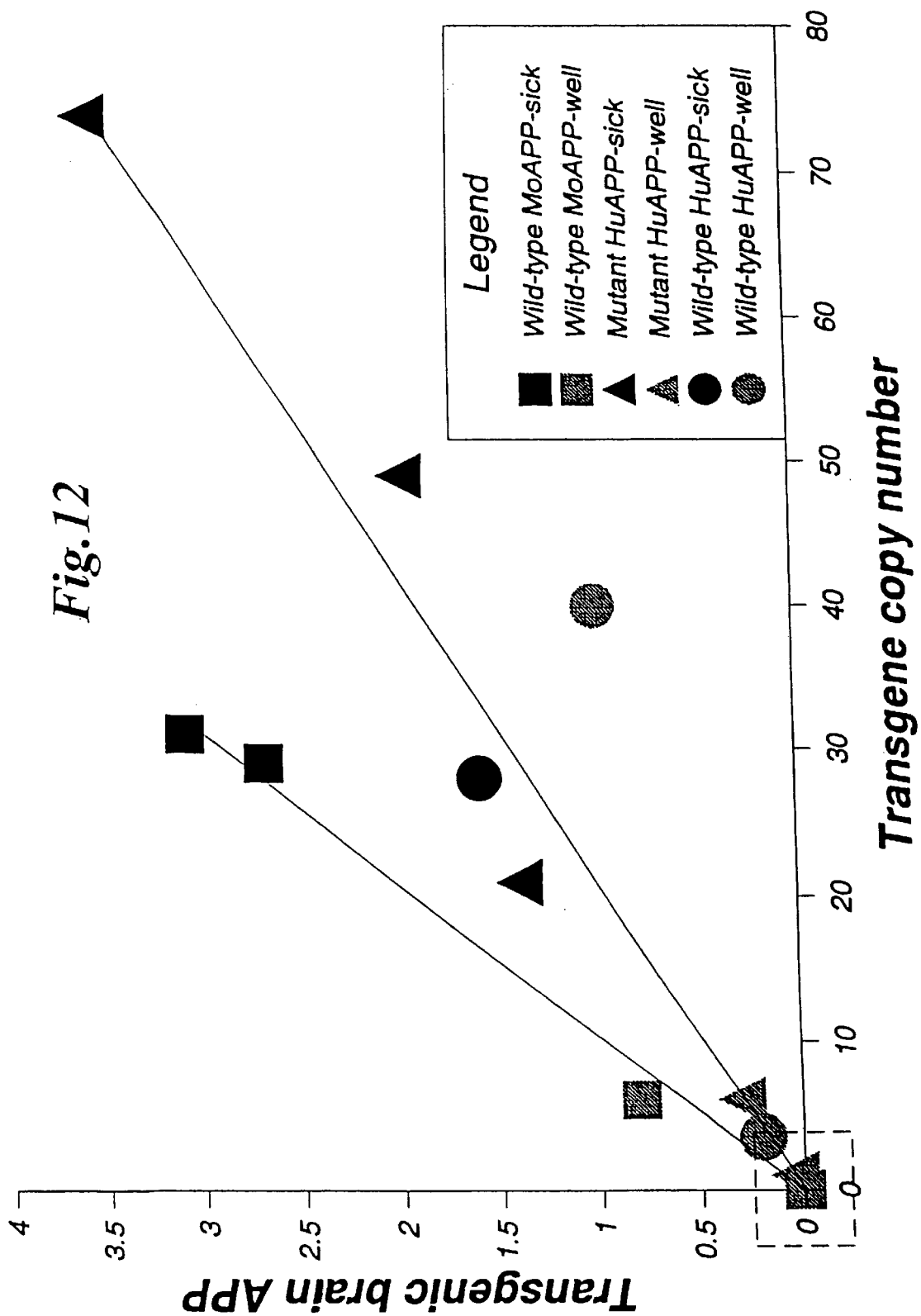
FIG. 12 shows the dependence of transgenic brain APP expression upon species and copy number.

The supernatants were mixed with an equal volume of 2 X sample buffer (Laemmli, (1970) Nature 227, 680–685), boiled 2 min., and fractionated using a 6% SDS-PAGE. Proteins were electrophoretically transferred to Immobilon membranes (Pierce) and incubated with polyclonal (CT15 and antiGID) and monoclonal (22C11 and 6E10) APP antibodies. Reactive rabbit polyclonal antibodies were visualized following incubation with secondary rabbit antibodies to mouse IgG before incubation with $^{125}$I-protein. Radiointensities were quantified on a phosphorimager (Molecular Dynamics, Inc.). APP expression in brain tissue was measured in transgenic mice harboring different transgene copy numbers by quantification of immunoblots in transgenic lines with three antibodies recognizing both MoAPP and HuAPP, CT15 (FIG. 11), anti-GID (FIG. 11), and 22C11 (FIG. 11). CT15 (Sisodia et al., (1993) J. Neurosciences 13:3136–3142; Borchelt et al., (1994) J. Biol. Chem 269: 14711–14714); anti-GID (Cole et al., (1989) Brain Res. Reviews 13:325–349); and 22C11 (Weidemann et al., (1989) Cell 57:115–126) recognize both mouse and human APP equally, but 22C11 also binds APLP2, a close relative of APP, with the same avidity (Slunt et al., (1994) J. Biol. Chem 269:2637–2644). Minor variations in HuAPP levels relative to MoAPP expression obtained with different antibodies may reflect differences in the avidity of antibody binding or distinctions in post-translational processing between wild-type and variant HuAPP. Transgenic brain APP protein expression was dependent upon copy number as well as the species of APP expressed (FIG. 12). Relative to HuAPP, equivalent levels of MoAPP were achieved with lower numbers of transgene copies.

To measure the level of HuAPP specifically, brain homogenates were probed with 6E10 antibody raised against residues 1–17 of human Aβ (Kim et al., (1990) Neuroscience Res. Comm. 7:113–122). No reactivity to ~100–125 kD APP molecules was detected in non-transgenic mice (FIG. 11). In Tg1130H mice the highest levels of HuAPP detected on immunoblots using 6E10 antibody were in the brain and spinal cord, and much smaller amounts (<5% of brain levels)

were found in the striated muscle, heart, skin, and lung. HuAPP was poorly detected or absent in the thymus, liver, spleen, kidney, testis, and small intestine.

Figure 13A:
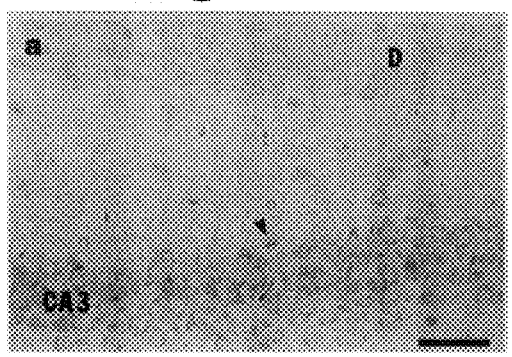
FIG. 13A. Tg, formic acid pretreatment, 6E10 antibody (hippocampus)
Figure 13B:
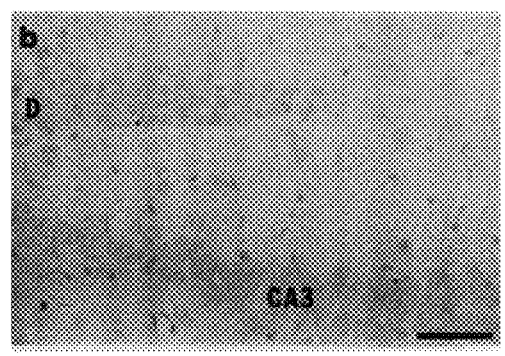
FIG. 13B, Non-Transgenic, formic acid pretreatment, 6E10 antibody (hippocampus)
Figure 13C:
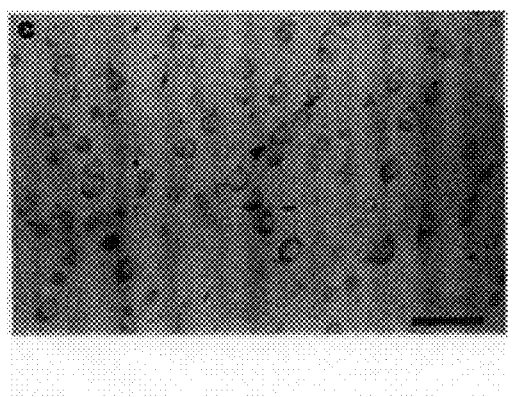
FIG. 13C Tg, formic acid pretreatment, 6E10 antibody (cerebral cortex)

Specific immunostaining for human APP/Aβ using the 6E10 or 8E5 antibody (Athena Neurosciences) revealed HuAPP throughout the brain. 8E5 recognizes a segment of APP spanning residues 444–592 (APP695 numbering). Two different methods were used to enhance APP immunoreactivity in brain tissue from transgenic lines overexpressing HuAPP. In high copy number lines, following either formic acid pretreatment of tissue using 1:5000 dilution of 6E10 antibody or microwave pretreatment of tissue using either 1:100 6E10 antibody or 1:100 8E5 antibody, APP staining was invariably present within vesicular structures in large pyramidal cells of the hippocampus, parahippocampal area, amygdala, and the cerebral cortex (FIGS. 13A, C, H). In some brains, fainter immunoreactivity was also visible in smaller neurons in the cortico-limbic regions of the brain and in large and small neurons of the basal ganglia, brainstem, and cerebellum. Staining was absent in non-transgenic mice (FIGS. 13B, H) and in untreated brain tissue from affected transgenic mice. The pattern of HuAPP immunostaining obtained reflected the widespread expression of HuAPP in the brain with the highest levels of expression in the telencephalon, as independently confirmed in regional brain immunoblots using the 6E10 antibody (FIG. 11).

Figure 13D:
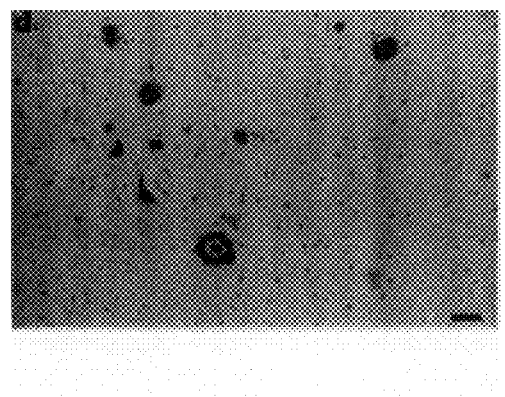
FIG. 13D, AD plaque, formic acid pretreatment, 6E10 antibody.
Figure 13E:
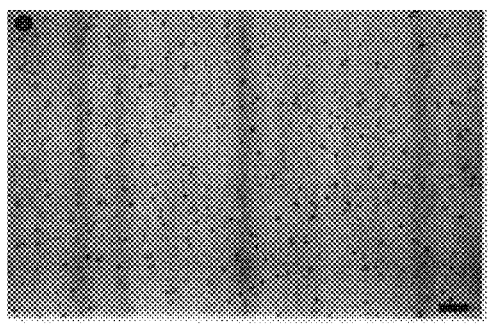
FIG. 13E, AD plaque, no formic acid pretreatment, 6E10 antibody.
Figure 13F:
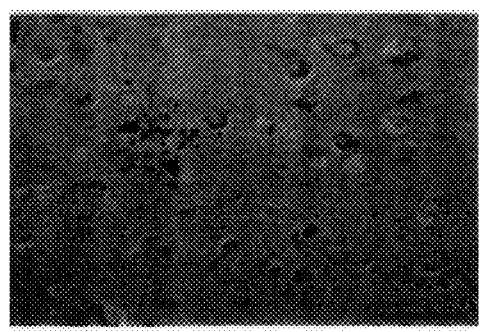
FIG. 13F, AD plaque, microwave pretreatment, 8E5 antibody.
Figure 13G:
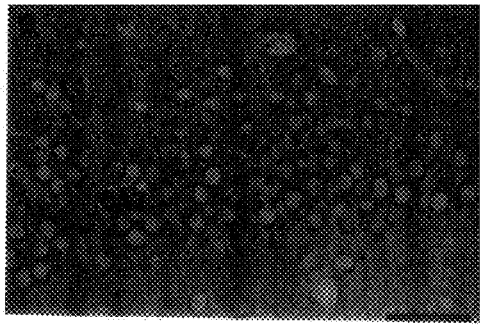
FIG. 13G, Tg, microwave pretreatment, 8E5 antibody (hippocampus)
Figure 13H:
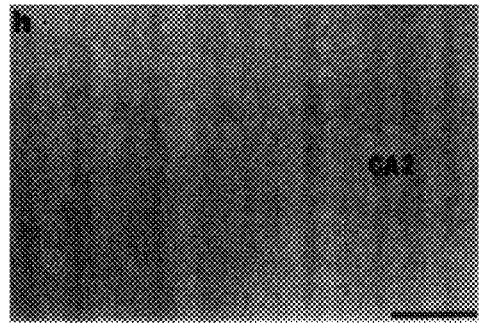
FIG. 13H, Non-transgenic, microwave pretreatment, 8E5 antibody (hippocampus).
Figure 14:
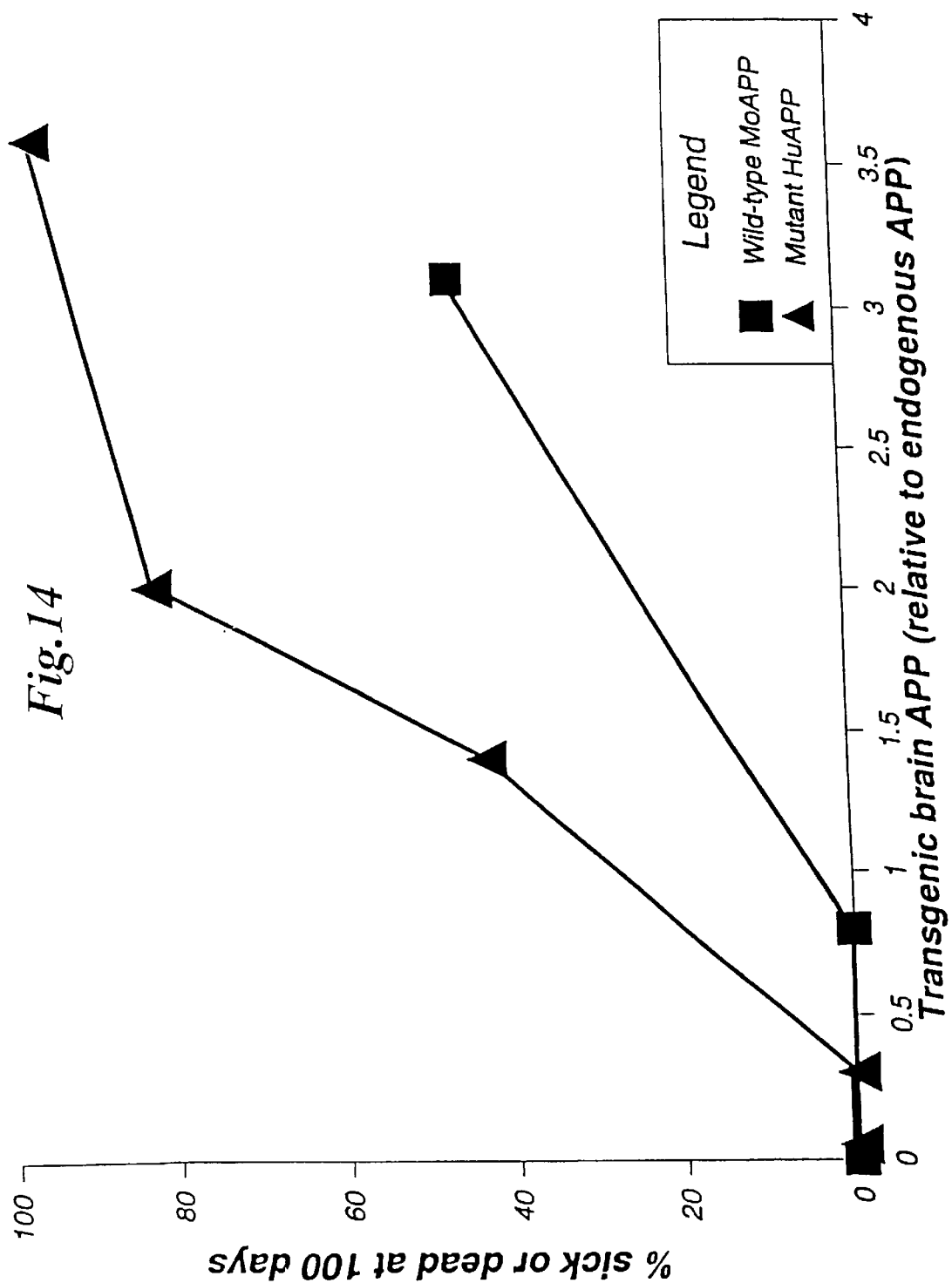
FIG. 14 shows the dependence of the CNS disorder upon level of transgenic brain APP expression and APP genotype.

The 8E5 antibody stained amyloid plaques and intraneuronal vesicular structures in microwaved tissue sections from patients with AD (FIG. 13F). At 1:5000 dilution, the 6E10 antibody stained amyloid plaques from patients with AD only after formic acid pretreatment of brain tissue (FIGS. 13D, E). However, in TgHuAPP mice neither the microwave nor formic acid pretreatment of brain tissue revealed HuAPP staining resembling extracellular amyloid or pre-amyloid deposits using either antibody. The abnormal phenotype in these transgenic mice, therefore, was not caused by amyloid or pre-amyloid deposition.

in lines expressing different levels of wild-type HuAPP, mutant HuAPP, or wild-type MoAPP (Table 5) was determined. These data demonstrate a direct relationship between APP expression and the development of an abnormal phenotype (FIG. 15). A comparison of transgenic mice expressing wild-type HuAPP and mutant HuAPP was not possible over the full range of APP expression. However, a comparison of transgenic mice expression approximately two to four fold mutant HuAPP, (TgHuAPP695.TRImyc)1140 and (TgHuAPP695.TRImyc)1130, with transgenic mice expressing approximately three fold wild-type MoAPP, (TgMoAPP695.WT)1874, indicates that mutant HuAPP will readily provoke the abnormal phenotype. This observation argues against the abnormal phenotype being due to a non-specific effect of transgenic protein over expression, since mutant HuAPP conferred the disorder with higher penetrance than wild-type MoAPP, demonstrating a specific effect of the transgenic protein species it expressed. These data are represented as titration curves that demonstrate a direct relationship between APP expression and the development of an abnormal phenotype (see FIG. 15). However, the left-shifted curve for transgenic mice expressing mutant APP relative to wild-type APP indicates that expression of the mutant APP more readily provokes the abnormal phenotype.

To ensure that overexpression of a foreign (human) species of protein did not artefactually produce the abnormal phenotype, transgenic mice overexpressing wild-type MoAPP were generated. In transgenic mice with MoAPP levels equivalent to 3.1-fold endogenous APP levels the same phenotype occurred, indicating that the observed phenotype was not due to overexpression of a foreign species of protein.

TABLE 5

Clinical and pathological features of FVB mice expressing APP transgenes

| Line | Copy Number (mean ± SEM) | Transgenic brain APP (mean ± SEM) | % sick or dead at 100 days | % sick or dead at 200 days | Cortico-limbic gliosis (in affected mice) | Extra-cellular HuAPP deposits | Weight (gm ± SEM) Tg | Non-Tg |
|---|---|---|---|---|---|---|---|---|
| Tg (HuAPP695. TRImyc) 1072 | | <0.05 | 0 (n = 21) | 0 (n = 21) | | | | |
| Tg (HuAPP695. TRImyc) 1056 | 7 ± 1.7 | 0.3 ± 0.09 | 0 (n – 10) | 10 (1/10) | | | | |
| Tg (HuAPP695. TRImyc) 1118 | 21 ± 3.7 | 1.4 ± 0.17 | 42.5 (20/47) | 97 (20/30) | +(1/1) | — | 21.9 ± 0.46 | |
| Tg (HuAPP695. TRImyc) 1140 | 49 ± 2.5 | 2.0 ± 0.32 | 83 (15/18) | 93 (15/16) | | | 18.0 ± 0.92 | 20.6 ± 0.38 |
| Tg (HuAPP695. TRImyc) 1130H | 74 ± 3.7 | 3.6 ± 0.54 | 98 (59/60) | 100 (60/50) | +(3/3) | — | 11.4 ± 0.50 | |
| Tg (HuAPP695. TRImyc) 1057F | 64 – 128 | N/A | 100 (1/1) | 100 (1/1) | +(1/1) | — | | |
| Tg (HuAPP695. TRImyc) 1138 | 64 – 128 | N/A | 100 (4/4) | 100 (4/4) | +(2/2) | | | |
| Tg (HuAPP695. SWE) 2123H | 46 | N/A | 100 (2/2) | 100 (2/2) | | | | |
| Tg (HuAPP695. SWE) 1844F | 42 | N/A | 100 (1/1) | 100 (1/1) | +(1/1) | — | | |
| Tg (HuAPP695. SWE) 1837F | 42 | N/A | 100 (1/1) | 100 (1/1) | +(1/1) | — | | |
| Tg (HuAPP695. SWE) 1827F | 59 | N/A | 100 (1/1) | 100 (1/1) | +(1/1) | — | | |
| Tg (HuAPP695. SWE) 1665F | 244 | N/A | 100 (1/1) | 100 (1/1) | +(1/1) | — | | |
| Tg (HuAPP695. DUT) 2012 | 47 ± 3.4 | N/A | 100 (3/3) | 100 (3/3) | ( /2) | | | |
| Tg (HuAPP695. WTmyc) 6214 | 4 ± 0.3 | | 0 (n = 25) | 0 (n = 25) | | | | |
| Tg (HuAPP695. WTmyc) 466 | 40 ± 9.0 | 1.0 ± 0.21 | 0 (n = 12) | 33 (1/3) | –(0/1) | | | |
| Tg (HuAPP695. WTmyc) 6209 | 28 ± 6.1 | 1.6 ± 0.43 | 35 (5/15) | 75 (9/12) | | | | |
| Tg (MoAPP695. WT) 1859 | 6 ± 0.8 | 0.8 ± 0.21 | 0 (n= ) | 0 (n = 2) | | | | |
| Tg (MoAPP695. WT) 1869 | 26 | | 75 (3/4) | 100 (4/4) | +(1/2) | | | |
| Tg (MoAPP695. WT) 1874 | 31 ± 3.7 | 3.1 ± 0.55 | 47 (8/17) | 79 (11/14) | +(3/5) | | | |
| Tg (MoAPP695. WT) 1855 | 29 | 2.7 ± 0.1 | 0 (n = 2) | 100 (2/2) | | | | |

To assess the relative effects of mutant and wild-type APP transgene expression on the development of a CNS disorder, the percentage of animals sick or dead at 100 and 200 days Behavioral Analyses To determine whether FBV mice naturally became behaviorally impaired with advancing age (the mouse equivalent of senile dementia in humans, or the old dog which has forgotten its tricks), FBV mice were observed up to one year and the behavior of these aged mice compared to that of transgenic mice. Behavioral analyses were usually performed three times per week using the corner index (CI) test. The test exploits a striking neophobic response which occurs in many affected transgenic mice. The neophobic response is manifested by a decrease in exploratory activity specific to testing in a novel chamber. Early in the clinical course, affected mice often appear normal in their home cages but exhibit transient immobility for 30 to 60 seconds after being placed alone in a clean cage, in contrast to unaffected mice which typically explore and sniff around the novel setting. A characteristic response of an affected mouse is to hold its neck low with its tail stiff during the transient immobility. Alternatively, an affected mouse runs to a corner and then assumes a crouched or frozen posture there. The (CI) test measures the number of times a mouse sniffs the corners of a clean cage during the first 30 seconds after it is placed alone into that cage. Based upon the collective observations of >2000 tests of >100 transgenic mice and >2500 tests of >140 non-transgenic mice, we established criteria for the presence of a behavioral disorder were determined to be scores of two "0's" or "0 and 1" occurring within three consecutive tests. The onset of illness is ascribed to the first of three consecutive testing dates in which abnormal scores were obtained.

To perform the corner index test, a test mouse, held by the tail, is placed in the center of a clean cage that is otherwise identical to its home cage. The number of times the mouse sniffs the corners of the test cage during the first 30 seconds after it was placed into that cage are recorded as the CI. Animals which are obviously moribund before attaining the CI criteria and animals which develop witnessed seizures also are diagnosed as ill. Animals housed alone are excluded from the analysis because several non-transgenic and transgenic mice obtain low scores while housed alone without displaying the characteristic freezing postures of the affected transgenic animals. When these mice are housed with other mice, their CI scores increase. To control the variations in diurnal activity, all animals are tested between 1430 h and 1830 h.

An Age-Related CNS Disorder in FVB Mice
Behavioral Abnormalities.

The life expectancy of FVB mice is approximately 600 days but little is known about age-related CNS disorders in FVB mice. To determine whether FVB mice naturally become behaviorally impaired with advancing age, 110 FVB mice 150–500 days of age from three different institutions (University of Minnesota, Minneapolis, Minn., McLaughlin Research Institute, Great Fall, Mont., and Harlan Sprague Dawley, Inc. Indianapolis, Ind.) were observed. With advancing age, 18 mice as early as 154 days of age developed behavioral abnormalities, including agitation, inactivity, seizures, and neophobia, as defined by the corner index test, and premature death (Table 6). Another six mice died from tumors or accidentally. Although agitation or inactivity occurred in all affected transgenic mice, these were subjective signs that rarely appeared in most normal mice. The onset of illness was defined by corner index test results in conjunction with the observation of seizures, agitation or apathy. Both male and female mice were affected. Three agitated mice died prior to diagnosis by corner index criteria. One death occurred immediately following an observed seizure. The remaining mice grew progressively less active, and were sacrificed for pathologic studies between nine and 91 days after the onset of abnormal behavioral signs. The cumulative incidence of behavioral abnormalities and death (excluding accidental and tumor-related deaths) in this cohort of FVB mice was 23% by 500 days of age (see FIG. 9).

Gliosis. Brains from sixteen older non-transgenic FVB mice nine to twelve months of age, seven exhibiting the abnormal behavior characteristic of affected transgenic APP mice and nine age-matched behaviorally normal mice, were examined in a coded fashion. Six of the seven brains from the behaviorally abnormal mice exhibited profound hypertrophic astrocytic gliosis in the hippocampus, parahippocampal area, amygdala, and cerebral cortex (FIG. 10). None of the brains from the nine age-matched, behaviorally normal mice exhibited this degree of gliosis, although moderate gliosis restricted to the hippocampus was observed in some mice. These findings indicate that the behavioral disorder in affected older non-transgenic mice is tightly associated with cortico-limbic gliosis (Yates-corrected $X^2=8.96$, p=0.003). The brains of the non-transgenic behaviorally impaired FVB mice showed non amyloid plaque deposition, neurofibrillary tangle formation, neuronal abnormalities, or qualitative changes in neuronal or glial numbers.

Regional-cerebral glucose utilization. To obtain an independent functional assessment of the abnormal behavior observed in impaired FVB mice, regional brain glucose utilization was determined using a modification of the Sokoloff method (Sokoloff, et al., *J. Neurochem.* 28,897–916 (1977)). Regions associated with learning, memory, and emotion such as the cerebral cortex, hippocampus, entorhinal cortex, and amygdala, which are most impaired in cognitively impaired aged humans and patients with AD were examined. Densitometric values of $^{14}C$-deoxyglucose distribution were normalized to cerebellar values because the cerebellum appeared uninvolved clinically and pathologically. The regional cerebral glucose utilization in cerebral tissue in impaired FVB mice was compared to that in cerebral tissue in behaviorally normal, age-matched FVB mice. Significant decreases (p<0.05, analysis of variance) in regional glucose utilization, particularly in the hippocampus (−42%), amygdala (−43%), entorhinal cortex (−46%), parietal cortex (−34%), frontal cortex (−19%) and temporal cortex (−18%), were observed in the cerebral tissue in the impaired FVB mice. In contrast, no significant decreases were observed in several structures, including the corpus callosum, medullary reticular formation, dentate nucleus, and vermis.

The development of impaired behavior accompanied by cortico-limbic hypertrophic gliosis and diminished regional cerebral glucose utilization, especially in the cerebrum, in FVB mice defines a characteristic age-related CNS disorder with features of the senescent changes observed in other rodent species, such as hypertrophic gliosis and diminished regional glucose utilization in limbic and cortical structures. Although the age-related behavioral abnormalities observed in impaired FVB mice have not been described to occur naturally in other rodents, the major decrease in regional cerebral glucose utilization found in the cortico-limbic areas of the brain involved in learning, memory, and emotion, strongly suggest that some, if not most, of the behavioral abnormalities in affected FVB mice reflect dysfunction in these brain regions. Because the behavioral, pathological, and functional abnormalities observed in these mice share features found in other aged, impaired rodents and in demented humans, the constellation of findings represents a form of CNS senescence in FVB mice.

Transgenic Mice Expressing Mutant and Wild-Type APP

Behavioral abnormalities. An abnormal phenotype resembling that in aged, impaired FVB mice developed in animals expressing high levels of APP. Copy number per se was unlikely to be the direct cause of the CNS disorder, since a previously published transgenic line developed in FVB mice, Tg(HuPrP)FVB-152, expressing human PrP driven by 30–50 copies of the hamster PrP gene cosmid exhibited no premature behavioral abnormalities or death (Telling, et al., (1994) *Proc. Natl. Acad. Sci. U.S.A.* 91, 9936–9940). The phenotype in TgAPP mice segregated according to the species, genotype and level of APP expression in four lines harboring roughly equivalent copy numbers (20–30: Tg(HuAPP695.WYmyc)466, Tg(MoAPP695.Wtmyc)6209. To determine whether PrP levels were affected by the presence of supernumerary PrP gene components, brain PrP levels were measured in Tg(HuAPP695.TRImyc)1130 mice with 74 transgene copies and non-transgenic mice. No differences were found, indicating that alterations in PrP expression were also not the cause of the abnormal phenotype.

Affected transgenic animals developed all the clinical signs observed in aged, impaired non-transgenic FVB mice, including agitation, increased startle responses, apathy, and neophobia (Table 6), but they occurred with significantly high penetrance at earlier ages (FIG. 9, Table 5). Later in the course inactivity and failure to reproduce developed but there was no tremor, incoordination, weakness, paralysis, or apparent loss of sensation as judged from their withdrawal or vocal responses to tail or foot pinching. Seizures were observed in a small percentage (3% (6/181)) of affected Tg(HuAPP695.TRImyc) mice. It is possible that the actual incidence of seizures is higher, and would be detected if mice were observed for more than 30–60 seconds three times per week.

Behavioral abnormalities in transgenic mice developed as early as one month of age. There was no significant difference between the onset of behavioral abnormalities in male and female mice. Some transgenic mice (<14%) overexpressing APP died as early as one month of age without exhibiting prior seizures or neophobia. A neuropathologic examination of two of these mice identified cortico-limbic gliosis indistinguishable from transgenic mice that had died after exhibiting the characteristic behavioral signs, so it is probable that these mice died as a result of the same disorder as the other affected transgenic mice.

Small stature was observed in animals with transgenic brain APP levels exceeding twice the endogenous levels (Table 5). This difference in size was not apparent at birth but became conspicuous by four to six weeks of age, and was less or absent in older animals. The transgenic animals appeared normally proportioned. Small size was not required for behavioral abnormalities to occur, since Tg(HuAPP695.TRImyc)1118 mice died prematurely and developed behavioral abnormalities despite being normal in size.

TABLE 6

Clinical and pathological signs in aged, impaired FVB mice and in affected FVB mice expressing APP transgenes

| Signs | % aged, impaired FVB mice | % affected Tg FVB mice |
| --- | --- | --- |
| Seizures | 17% (3/18 | 3% (6/181) |
| Agitation or inactivity | 100% (18/18) | 100% (181/181) |
| Neophobia | 83% (15/18) | 84% (152/181) |
| Early death (excluding sacrificed mice | 100% (4/4) | 100% (82/82) |
| Cortico-limbic gliosis | 86% (6/7) | 76% (16/21) |

Pathological Analyses of Transgenic Mice

Brains of transgenic mice exhibiting behavioral abnormalities or found dead and age-matched nontransgenic littermates were examined for neuropathologic abnormalities. Brains were immersion fixed or perfused with 10% phosphate-buffered formalin or 4% buffered paraformaldehyde, embedded in paraffin, and cut into 5–8 μm sections on a rotary microtome. Tissue sections were stained with hematoxylin and eosin, cresyl violet, thioflavin S, or Congo Red stains, or using the Bielschowsky silver or TUNEL (Gavrieli, et al., (1992) *Journal of Cell Biology* 119, 493–501) methods.

For immunohistologic studies, paraffin sections were deparaffinized and rehydrated through xylol and graded alcohols. Endogenous peroxidase was quenched by treatment with 6% hydrogen peroxide in methanol for 10 minutes or with 3.0% hydrogen peroxide in methanol (1:5), and rinsed in deionized water or phosphate buffered saline. To enhance APP antigen detection, selected sections were microwave irradiated in water at full power for 15 minutes, cooled to room temperature, transferred to deionized water in 0.5 M TBS (pH 7.6), and pretreated with 0.4% TX/TBS, followed by 3% normal goat serum in TBS. Primary antibodies 6E10 (1:100) and 8E5 (1:100 ascites fluid) were prepared in 0.1% TX/TBS with 2% normal goat serum.

Following incubation for 24 hours, slides were rinsed, incubated in goat-antirabbit or -antimouse IgG (1:20) in 0.1% TX/TBS, and rinsed in TBS followed by one-hour incubation in rabbit or mouse peroxidase-antiperoxidase (1:100) at room temperature. Rinsed slides were reacted in the presence of 0.05% diaminobenzidine in 0.01% hydrogen peroxide, rinsed three times in TBS, dehydrated through a graded series of alcohols to xylene. Representative sections were silver-enhanced according to the Fontana-Masson method (Masson (1928) *Am. J. Path.* H:118–211), and viewed under transmitted light microscopy and differential interference contrast optics. Other sections were immersed in 70% formic acid for 10 minutes, rinsed in phosphate buffered saline, and immersed in 10% normal hose serum for 1 hour. Primary antibody 6E10 (1:5000) was prepared in phosphate buffered saline. Following incubation overnight at 4° C., sections were rinsed in phosphate buffered saline, incubated with antimouse IgG, followed by avidin-biotin complex (Vector Labs, Inc.). Rinsed slides were reacted with diaminobenzidine and counterstained with Harris hematoxylin. GFAP was detected using a monoclonal antibody to GFAP at a dilution of 1:60 in phosphate buffered saline.

Gliosis. Using coded specimens, brains from 21 affected transgenic mice expressing the triple HuAPP variant, the Dutch HuAPP variant, the Swedish HuAPP variant, wild-type HuAPP, as well as brains from 12 age-matched, unaffected non-transgenic mice were examined. Brains from 16 affected transgenic mice exhibited prominent hypertrophic astrocytic gliosis located predominantly in the parahippocampal area, hippocampus, amygdala, and cerebral cortex (FIG. 10), with relative sparing of the basal ganglia. The astrocytes had enlarged, elongated processes when immunostained for glial fibrillary acid protein (GFAP), but there was no increase in the number of astrocytes. Brains from the age-matched non-transgenic mice were devoid of the reactive gliosis, indicating a strong association between gliosis and abnormal behavior (Yates-corrected $X^2$=14.83, p=0.00012). Bielschowsky silver stains revealed no neurofibrillary tangles, dystrophic neurites, or neuritic plaques. Neurons appeared normal with Nissl and hematoxylin and eosin stains.

Gross and microscopic examinations of six transgenic mice found dead revealed characteristic brain pathology (astrocytic gliosis in the hippocampus, cerebral cortex, amygdala, and parahippocampal area, as described below), but no evidence of microscopic or gross pathology outside the CNS. Amyloid was specifically excluded by thioflavin S staining in the heart, ling, liver, spleen, thymus, kidney, small intestine, and testes in four of these transgenic mice. The absence of pathologic findings outside the CNS indicates that the deaths were most likely due to causes which were neurologic in origin.

Regional Cerebral Glucose Utilization

To determine whether there were functional differences in the brains of affected transgenic mice, regional brain glucose utilization was compared among affected transgenic mice with aged, impaired non-transgenic FVB mice and age-matched non-transgenic mice. Compared to normal, non-transgenic littermates, significant reductions ($P<0.05$; analysis of variance) in glucose utilization were observed in various forebrain regions in transgenic mice, including the hippocampus (−31%), amygdala (−28%), parietal cortex (−34%), temporal cortex (−33%), and occipital cortex (−36%). Many regions, in contrast, showed no significant reduction ($p>0.05$), including the sensory-motor cortex, corpus callosum, reticular formation, vermis, vestibular complex, and dentate nucleus. The diminution of regional glucose utilization was particularly pronounced in the hippocampus, amygdala, and some cortical regions in affected transgenic mice closely resembling that occurring in older, impaired non-transgenic FVB mice.

Extracellular Aβ Staining in a Transgenic Mouse

One animal shows extracellular staining with an antibody described in Saido, et al., *J. Biol. Chemistry* 269:15253–15257 (1994). This antibody specifically stains the aminoterminus of Aβ. It is an affinity purified polyclonal antibody. The staining in our transgenic mouse can be blocked by specific competition with the Aβ fragment. The staining pattern in our transgenic mouse resembles that which is seen in AD brain stained with the same antibody. More animals are being examined. Further characterization with other antibodies is being done. Ultrastructural studies also being done.

Example 7

Expression of APP Transgenes in FVB/N Mice

Transgene Construction

The PrP-APP transgenes were generated by inserting Sal1-flanked human or mouse APP ORFs into a hamster PrP cosmid vector. This vector is a ~40 kb fragment of genomic DNA containing the hamster PrP gene with ~20 kb of upstream sequences, in which the hamster PrP ORF is replaced by a unique Sal1 restriction site. The HuAPP695.SWE, HuAPP695.TRImyc, and HuAPP695.TRImyc, and APP sequences were modified for strong translation initiation. The 5' end of the APP coding sequence is preceded by a Sal1 site and a strong Kozak translation initiation sequence (5'-GTCGACACC-ATGCTGCCC... (SEQ ID NO:16)), and the 3' end of the APP coding sequence is immediately followed by a Sal1 site (...AACTAGCAGCTG-3' (SEQ ID NO:17));start and stop codons are underlines; site in boldface). These modifications and the APP mutations were made using standard cloning methods and polymerase chain reaction (PCR)-based, site-directed mutagenesis. The PrP-APP cosmids were digested with Not1, which releases the PrP-APP fusion gene from the pcos6EMBL vector. The PrP-APP fusion genes were isolated after size fractionation on an agarose gel and electroeluted. The PrP-APP fusion gene was further purified with organic solvents and precipitated in ammonium acetate and ethanol. The PrP-APP fusion genes were dissolved in 5 mM Tris-Cl (pH 7.4) or 10 mM Tris-Cl (pH 8.0) to a final concentration of 2–2 μg/ml prior to embryo injection.

Transgenic Mouse Generation and Screening

Transgenic lines were initiated by microinjection of single-cell mouse embryos. The embryo donors and fertile studs were inbred FVB/N mice obtained from the National Cancer Institute (NIH). Post-weaning tail biopsy DNA was generated and 1 μl of unpurified DNA was used in a 25 μl PCR reaction. To detect PrP-APP fusion DNA, the PrP-APP fusion DNA was amplified using the PCR with a pair of oligomer primers, 1503: (5'-CTGACCACTCGA-CCAGGTTCTGGGT-3' and 1502 (5'GTGGATAACCCCTCCCCCAGCCTAGACCA-3'), located in the 3' region of APP and the 3' untranslated region of PrP, respectively (See FIG. 8). The 1503 primer recognizes a region that is homologous in mouse and human APP and could therefore be used to detect both PrP-MoAPP and PrP-HuAPP DNA. Using primers 1502 and 1501 (5'-AAGCGGCCA-AAGCCTGGAGGGTGGAACA-3'), a parallel PCR reaction applying a fragment of murine PrP was performed as a positive control.

Transgene copy number analysis was performed using 5 μg of denatured purified tail DNA baked onto nitrocellulose and hybridized to a radiolabeled 1.3 kb Sal1-Xho1 DNA fragment encoding a segment of the hamster PrP 3' untranslated region located in the hamster PrP cosmid vector. After two high stringency washes, the relative intensities of signals from genomic DNAs of transgenic mice and hamsters were compared using a phosphorimager to obtain transgene copy numbers relative to diploid hamster genomic DNA.

Analysis of Transgene Expression

APP transgene products were examined in progeny of transgenic founders sacrificed at 1–4 months of age. Quantitative immunoblotting of extracts from brain homogenates was carried out in parallel with extracts prepared from age-matched nontransgenic littermates. Homogenates (20%, w/v) of brain tissues were prepared in TNE (50 mM Tris-Cl(pH 8.0), 150 mM NaCl, 5 mM EDTA with 2% phenyl-methylsulfonyl fluoride) buffer using a hand-held polytron. Homogenates were diluted with an equal volume of TNE, 1% Nonidet P-40, 1% deoxycholate, 0.4% SDS and sonicated in a bath sonicator until all viscosity was lost. Homogenates were then boiled for 10 min. and centrifuged at 10,000×g for 10 min. the supernatants were mixed with an equal volume of 2× sample buffer (Laemmli, 1970), boiled 2 min. and fractionated using a 6% SDS-polyacrylamide gel. Proteins were electrophoretically transferred to Immobilon membranes (Pierce) and incubated with monoclonal (22C11 and 6E10) anti-APP antibodies. Reactive monoclonal antibodies were visualized following incubation with secondary rabbit antibodies to mouse IgG before incubation with $^{125}$I-protein A. Radioactivity was quantified on a phosphorimager (Molecular Dynamics, Inc.).

Analysis of Aβ in Brain Tissue

Approximately 0.2 g of tissue was dounce homogenized (4 strokes) in 1 ml of 70% glass-distilled formic acid. Homogenates were centrifuged at >100,000×g for 1 hr. The formic acid extract (layered between an overlaying lipid layer and a small pellet) was removed, and a small aliquot was diluted 50 times in 1 M Tris (pH 8.0). This sample was then further diluted 2.4 times in Buffer EC (0.02 M sodium phosphate (pH 7.0), 0.2 mM EDTA, 0.4 M NaCl, 0.2% bovine serum albumin, 0.05% CHAPS, 0.4% Block-Ace, 0.05% sodium azide), and 100 μl of this was analyzed directly using either the Ban50/Ba27 or Ban50Bc05 ELISA systems described previously (Suzuki et al., 1994; Gravina et al., 1995). Aβ values reported were obtained by comparing the absorbance obtained from duplicate samples to standard curves of either $A\beta_{1-40}$ (Ban50/Ba27) or $A\beta_{1-42}$ (Ban50/Bc05) obtained from Beachem. These values were corrected for dilution and initial wet weight of the tissue and are expressed as picomoles per gram of wet weight. All samples were coded with respect to the transgenic status of the animals.

Behavioral Analyses: Neophobia:

To perform the corner index test, a test mouse held by the tail is placed in the center of a cage (18×30×13 cm) with clean bedding (soiled bedding removed between tests), and the number of times the mouse sniffs the corners of the test cage during the first 30 s after being placed into the cage is recorded as the corner index (CI). (See Specification, page 18, lines 1–18). Animals are usually tested 3 times per week. Low scores in animals housed alone were excluded from the analysis unless they displayed thigmotaxis or the characteristic freezing posture of other neophobic transgenic mice. To control for variations in diurnal activity, all animals were tested between 1300 hr and 1830 hr. Criteria for the presence of neophobia in non-transgenic mice >150 days of age was $\geq 3$ consecutive scores of 0.

Pathological Analyses of Mice

Brains of mice exhibiting behavioral abnormalities or found dead and age-matched littermates were examined for neuropathologic abnormalities. Brains were immersion fixed or perfused with 10% phosphate-buffered formalin or 4% buffered paraformaldehyde, embedded in parafin, and cut into 5–8 µm sections. Tissue sections were strained with hematoxylin and eosin, cresyl violet, thioflavin S, or Congo red stains, or by using the Bielschowsky silver methods.

For immunohistologic studies, endogenous peroxidase was quenched by treatment with 6% hydrogen peroxide in methanol or with 3.0% hydrogen peroxide in methanol (1:5). To enhance APP antigen detection, selected sections were microwave-irradiated in water at full power for 15 min. cooled to room temperature, transferred to deionized water in 0.5 M TBS (pH 7.6), and pretreated with 0.4% Triton X-100 in TBS (TX/TBS), followed by 3% normal goat serum in TBS. Primary antibodies 6E10 (1:100) and 8E5 (1:100 ascites fluid) were prepared in 0.1% TX/TBS with 2% normal goat serum. Following incubation for 24 hr., slides were incubated in goat anti-rabbit or anti-mouse IgG (1:20) in 0.1% TX/TBS, followed by a 1 hr. incubation in rabbit or mouse peroxidase-antiperoxidase (1:100) at room temperature. Rinsed slides were reacted in the presence of 0.05% diaminobenzidiine in 0.01% hydrogen peroxide. Representative sections were silver enhanced according to the Fontata-Masson method (Masson, 1928). Other sections were immersed in 70% formic acid for 10 min., rinsed in PBS, and immersed in 10% normal horse serum for 1 hr. Following incubation overnight at 4° C. with primary antibody 6E10 (1:5000), sections were rinsed in PBS and incubated with anti-mouse IgG, followed by avidin-biotin complex (VectorLabs, Inc.). Rinsed slides were reacted with diaminobenzidine and counterstained with Harris hematoxylin. GAFP was detected using a monoclonal antibody to porcine GFAP (Sigma).

Regional Brain Glucose Utilization Analysis

Mice received an intraperitoneal injection of ($^{14}$C)2-deoxyglucose (New England Nuclear; 5 µCi in 0.4 ml of 0.9% NaCl) and were sacrificed 60 min. later. Brains were rapidly removed and frozen in isopentane cooled to –30° C. with dry ice. A sample of trunk blood was collected and used for determination of plasma glucose concentration by a glucose analyzer (Beckman). Techniques for quantitative autoradiography were according to the methods described by Ladecola et al., 1983; Ladecola and Xu, 1994 and are only summarized here. Coronal brain sections (20 µm) were cut on a cryostat (Hacker-Bright), mounted on glass slides, and exposed to X-ray film (Dupont) together with calibrated $^{14}$C standards (Ladecola et al., 1983). The film was developed 10 days later using an automatic developer (Kodak), and the optical density (OD) of regions of interest was determined bilaterally on four adjacent sections using a computerized image analyzer (MCID system. Imaging Research Inc.). OD was transformed into $^{14}$C concentration (nCi/g) using the standards on the film. Owing to the small size of some mice (15–20 g), blood sampling for determination of the 2-deoxyglucose arterial time course could not be performed, except at the time of sacrifice. Therefore, a CGU index was obtained by dividing regional radioactivity values (nCi/100 g/min) by the radioactivity of a region devoid of pathology, the whole cerebellum. This normalization procedure has been validated and widely used in small laboratory animals (e.g., Sharp et al., 1983; Mitchell and Crossman, 1984; Williot et al., 1988). In our experiments, the rate of $^{14}$C accumulation in cerebellum (nCi/100 g/min) and plasma glucose did not differ between control, aged, and transgenic mice. This finding indicates that the CGU index provides an accurate estimate of glucose utilization as determined by the method of Sokoloff et al. (1977).

PrP Cosmid Vector Drives Overexpression of APP in Transgenic Mice

To determine the effect of mutant and wild-type APP expression FVB/N mice, we replaced the prion protein (PrP) open reading frame (ORF) with a variety of APP ORFs in a hamster PrP cosmid vector. Transgenic mice harbored one of four different transgenes, some containing mutations associated with familial AD (MoAPP695.WT (wild type); HuAPP695.SWE (K670N and M671L, APP$_{770}$ numbering); HuAPP695.TRImyc (V717I, V721A, and M722V with a 3'-myc tag); HuAPP695.WTmyc (wild type with a 3'-myc tag); Mo, Mouse; Hu, Human). Initially, we introduced transgenes with a 3' myc tag, a 12 codon segment of the c-myc proto-oncogene, to facilitate immunodetection of transgene products (Wong and Cleveland, 1990). The myc tag exerted no apparent effect on the phenotype, since Tg(HuAPP695.SWE) mice lacking the myc tag developed the same clinical and pathologic features and those with the myc tag; the high level of APP expression obtained in our mice obviated the need for the myc tag. The experimental V721A and M722V mutations, unintentionally introduced to the APP ORF harboring the V717I mutation linked to early onset familial AD and discovered after transgenic lines had been established, exerted no obvious effect on the phenotype since Tg(HuAPP695.TRImyc) mice developed the same clinical and pathologic abnormalities as transgenic mice expressing the other three transgenes. Subsequent analyses of HuAPP695.TRImyc in cultured cells indicated that these unintentional mutations exert no significant effects on the processing of HuAPP relative to protein maturation, modification, or proteolytic processing to produce soluble actodomains or Aβ peptides.

APP expression was measured in brains of transgenic mice harboring different transgene copy numbers by quantitation of immunoblots in transgenic lines with the monoclonal antibody 22C11 which recognizes an identical epitope in both mouse and human APP as well as amyloid precursor-like protein 2 (APLP2), potentially leading to an underestimation of the amount of transgenic APP relative to endogenous MoAPP. APP protein expression in transgenic brain depended upon copy number as well as the species of APP expressed: MoAPP transgenes achieved levels equivalent to those of HuAPP transgenes, but with fewer copies.

Measurement of Aβ in Tg(HuAPP695.TRImyc) mice indicates that both Aβ$_{1-40}$ and Aβ$_{1-42}$ are generated in the brain. Aβ levels were not measured in transgenic FVB/N mice expressing HuAPP.SWE because of insufficient numbers of mice, owing to their poor breeding characteristics, and Aβ levels were not measured in transgenic mice expressing MoAPP because methods for reliably measuring mouse Aβ in the brain are not yet available. The Ban50 capture antibody does not recognize MoAPP; levels indicated for non-transgenic mice represent background signal. Both forms of Aβ were readily detectable in transgenic mice but were significantly higher in lines overexpressing APP and exhibiting clinical abnormalities than in an unaffected line expressing lower levels of APP.

Specific immunostaining for human APP/Aβ using the 8E5 or 6E10 monoclonal antibodies revealed HuAPP in vesicular structures within large pyramidal cells of the hippocampus, parahippocampal area, amygdala, and cerebral cortex, as well as fainter staining throughout the brain in smaller neurons and some glial cells. Antibody 8E5 (gift of Dale Schenk, Athena Neurosciences) recognizes a segment of APP spanning residues 519–667 ($APP_{770}$ numbering), and 6E10 recognizes residues 1–17 of human Aβ (Kim et al., 1990). The pattern of HuAPP immunostaining matched that of regional brain immunoblots which showed the highest levels of expression in the cerebrum. The brain and spinal cord contained the highest levels of HuAPP; the striated muscle, heart, skin, and lung contained <5% of brain levels; in the thymus, liver, spleen, kidney, testes, and small intestine HuAPP was undetectable.

PrP levels remained unchanged in animals with high transgene copy numbers, indicating that the PrP promoter and other sequences in the transgenes did not deplete transcription factor pools, and that the cellular machinery for synthesizing, modifying, and translocating membrane glycoproteins was not overburdened.

Behavioral Abnormalities: Neophobia and Other Neurologic Signs

The corner index test revealed a striking difference between transgenic and non-transgenic mice. Corner index scores for non-transgenic mice showed few values $\leq 1$ during the first 3 months, while scores of some transgenic mice overexpressing APP showed values $\leq 1$ with advancing age. The low scores appear to reflect a neophobic response. Based on >2000 tests of >100 transgenic mice and >2500 test of >140 non-transgenic mice <150 days of age, the age when two scores of "0" or a "0" and "1" appeared within three consecutive testing sessions defined the onset of neophobia. None of the 100 non-transgenic mice tested through 100 days of age or of the 48 non-transgenic mice tested through 150 days of age failed the corner index test. Neophobia developed as early as 1 month of age in both male and female transgenic mice overexpressing APP and preceded death by an average of 40 days in transgenic1130H mice. Six transgenic FVB/N lines and 4 additional founders expressing high levels of wild-type MoAPP695.WT, HuAPP695.SWE, HuAPP695.WTmyc, or HuAPP695.TRImyc exhibited neophobia. Mice failing the corner index test also exhibited other neurologic signs, including thigmotaxis, agitation, still tail, stare, tremulousness, and inactivity. Of 181 mice from affected lines, 6 had generalized tonic-clonic seizures during corner index testing.

We also generated transgenic FVB/N mice overexpressing wild-type MoAPP; 37% of transgenic1855 and 54% transgenic1874 mice were neophobic at 100 days, and 11% of transgenic1874 mice were dead at 100 days. The rate of development of neophobia was lower in transgenic mice expressing MoAPP695.WT than in transgenic mice expressing HuAPP695.TRImyc.

Regional Cerebral Glucose Utilization

To identify the affected areas of the brain in neophobic transgenic and enophobic mid- to late-adult non-transgenic FVB/N mice, regional brain glucose utilization was determined by densitometric measures of ($^{14}$C)deoxyglucose levels ($\mu$Ci/100 g/min). Regional cerebral glucose utilization in neophobic Tg1130H and age-matched non-transgenic mice was compared. The former exhibited significant reductions in glucose utilization in various cortico-limbic regions, including the entorhinal cortex (−37%; p=.008), hippocampus (−30%; p$\leq$.003), and amygdala (−28%; p=.004) as well as the parietal (−34%; p=.001, temporal (−33%; p=.017), and occipital (−36%; p=.001) lobes of the cerebral cortex. The somatosensory-motor cortex was relatively spared, corroborating the apparent absence of motor and sensory abnormalities in these mice, and many brain stem regions, including the pontine reticular formation, vestibular nuclear complex, and dentate nucleus, showed no significant reduction in glucose utilization.

Astrogliosis Without Amyloid formation in Brains of Transgenic FVB/N Mice

Using coded specimens, we examined brains of 19 neophobic transgenic mice expressing HuAPP695.SWE, HuAPP695.WTmyc, HuAPP695.TRImyc, or MoAPP695.WT as well as 12 age-matched, unaffected non-transgenic mice (see Table 2). Fifteen brains from affected transgenic mice exhibited prominent hypertrophic astrocytes located predominantly in the parahippocampal area, hippocampus, amygdala, and cerebral cortex, with relative sparing of the basal ganglia. The astrocytes had enlarged, elongated processes when immunostained for glial fibrillary acidic protein (GFAP), and there was no apparent increase in the number of astrocytes. Brains of ace-matched non-transgenic mice were devoid of reactive gliosis. In general, there was an association between gliosis and abnormal behavior (Yates-corrected $X^2$=14.83, p=.00012). Bielschowsky silver stains revealed no neurofibrillary tangels, dystrophic neurites, or neuritic plaques. Neurons appeared normal with Nissl and hematoxylin and eosin stains.

Seven non-transgenic FVB/N mice 9–12 months of age exhibiting neophobia and 9 age-matched, behaviorally normal mice were examined in a coded fashion. Six of the 7 brains from neophobic mice exhibited pronounced astrocytic gliosis in the hippocampus, parahippocampal area, amygdala, and cerebral cortex as detected by GFAP staining. The neostriatum showed little or no astrocytosis. None of the brains from the 9 age-matched, behaviorally normal mice exhibited this degree of gliosis, although modest gliosis restricted to the hippocampus was observed in some control FVB/N mice. These findings indicate that neophobia in non-transgenic FVB/N mice is associated with gliosis in the cerebral cortex and limbic brain regions (Yates-corrected $X^2$=8.96, p=.003). The brains of these mice showed no amyloid deposition, neurofibrillary tangles, neuronal abnormalities, or qualitative changes in neuronal or glial numbers. To detect APP or Aβ immunoreactivity in brain tissue from animals with clinical abnormalities in transgenic FVB/N lines overexpressing HuAPP, we used two antibodies: 8E5 antibody, which stained amyloid and intraneuronal vesicular structures in microwaved tissue sections from patients with AD, and 6E10 antibody, which stains amyloid from patients with AD only after formic acid pretreatment of brain tissue. In 4 Tg(HuAPP695.SWE) mice and 7 Tg(HuAPP695.TRImyc) mice, neither the microwave nor formic acid pretreatment of brain tissue revealed extracellular APP or Aβ immunoreactivity using these antibodies.

Amyloid deposits were not demonstrable by staining with Congo red or thioflavin S. We concluded that the abnormal phenotype in these transgenic mice occurred independently of amyloid plaque deposition.

The distinction between age-dependent penetrance of death and neophobia for FVB/N mice expressing MoAPP and HuAPP transgenes indicates that APP transgenes with different amino acid sequences differ in their age-dependent potency as regards the effect. However, the qualitative features of the phenotype we observe in all transgenic FVB/N mice overexpressing APP resemble an acceleration of a naturally occurring CNS disorder in FVB/N mice, regardless of the primary structure of APP. Although it is possible that the presence of two additional transmembrane mutations in HuAPP.TRImyc could diminish generation of $A\beta$, and thereby alter the phenotype, our date indicate that mice expressing this transgene are in fact able to generate both $A\beta_{1-40}$ and $A\beta_{1-42}$ and develop the same clinical abnormalities as transgenic mice expressing HuAPP695.SWE, HuAPP695.WTmyc, and MoAPP695.WT transgenes.

Example 8

Figure 15A:
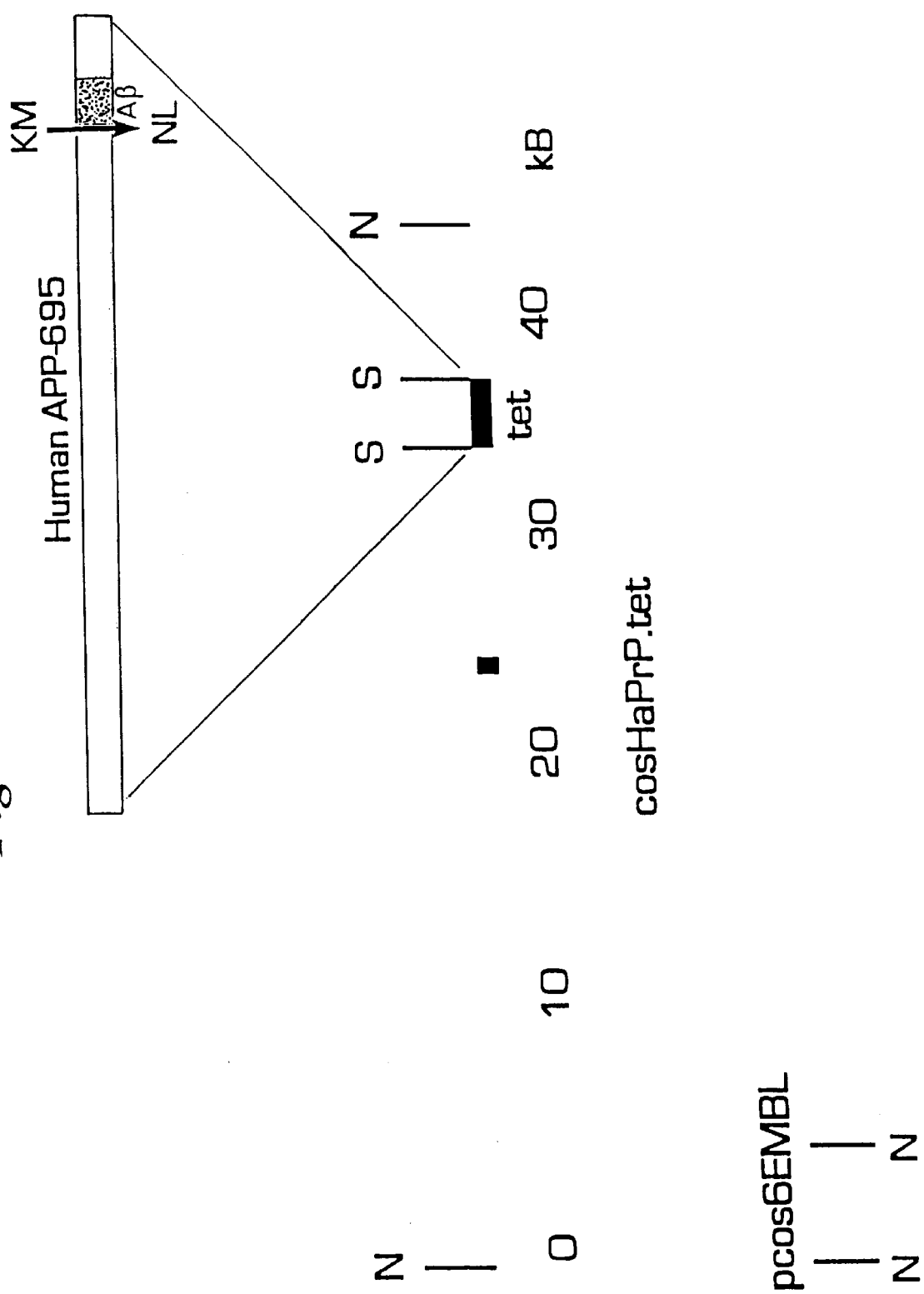
FIG. 15A, the cosHaPrP.tet cosmid vector was used to drive expression of human βAPP695 with the K670N-M671L mutation. The transgene used to create Tg2576 mice was made by substituting variant human βAPP ORF for a tetracycline resistance cassette replacing the hamster PrP ORF located in the second exon. Exons are represented by thick black lines, 3'- and 5' untranslated regions by thick stippled lines. N=NotI, S=SalI. Methods for the creation of transgenes and transgenic mice, including Tg2576 mice, are described in Hsiao, et al., (1995) *Neuron* 15: 1–16.
Figure 15B:
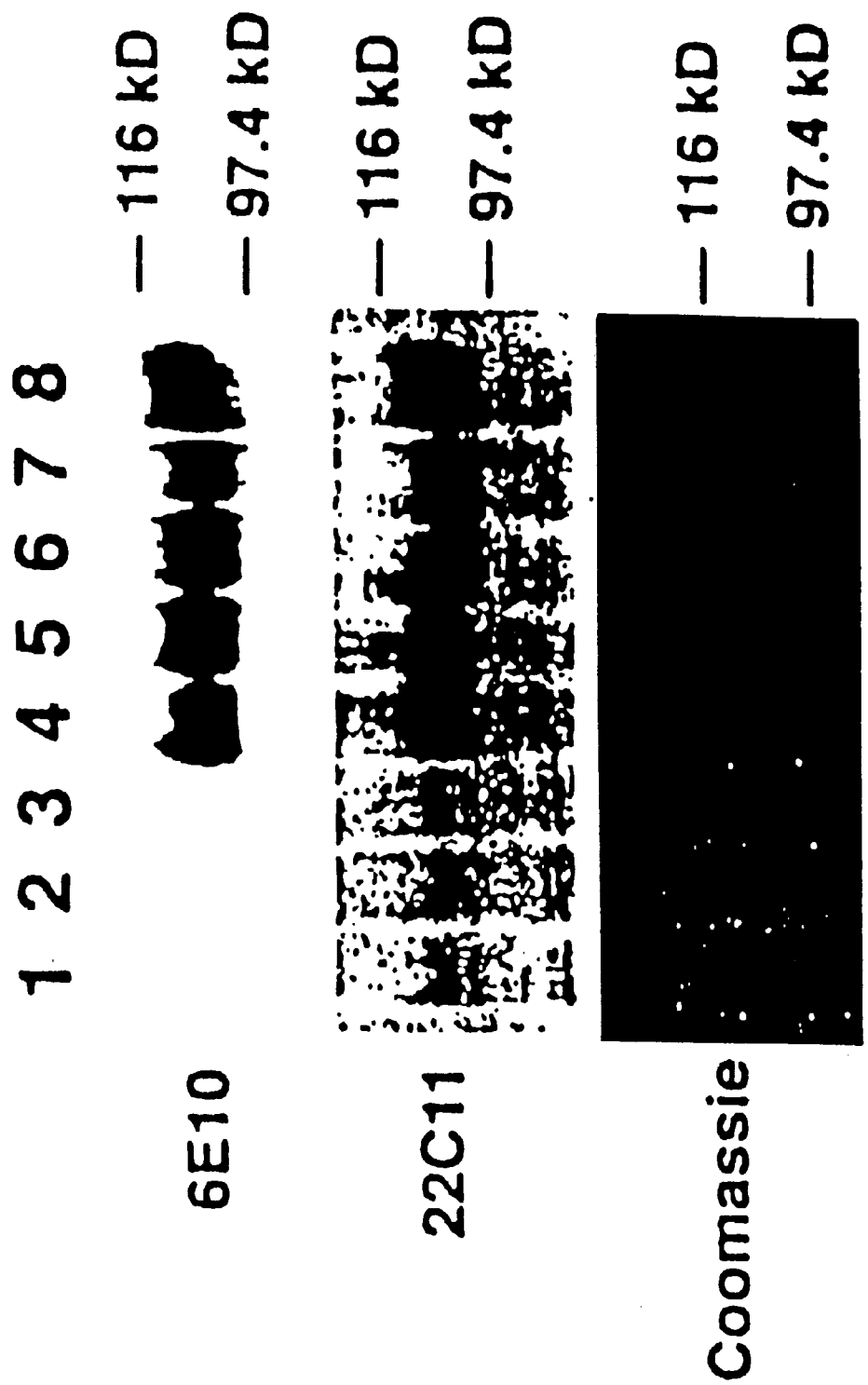
FIG. 15B, brain βAPP immunoblot of young and old transgene positive mice and non-transgenic control mice using 6E10 (21) which recognizes human but not mouse βAPP and 22C11 (Boehringer Mannheim) which recognizes both human and mouse βAPP. Lanes 1–3: Non-transgenic mice; Lanes 4–6; 73 day-old mice; lanes 7–8: 430 day-old mice. Detailed methods for βAPP quantitation are described in Hsiao, et al., (1995) *Neuron* 15: 1–16 except that antibody binding was revealed using $^{35}$S-protein A instead of $^{125}$I-protein A.

Correlative Memory Deficits, $A\beta$ Elevation and Amyloid Plaques in Transgenic Mice Tg(HuAPP695.K670N-M671L)2576 mice were generated by driving expression of human $\beta$APP-695 containing K670N-M671L ($\beta$APP-770 numbering), a mutation found in a large Swedish family with early onset AD (Mullan, et al., *Nature Genetice* 1:345–347 (1992)), with a hamster prion protein (PrP) cosmid vector (Scott, et al., *Protein Sci* 1:986–97 (1992)) in which the PrP open reading frame (ORF) was replaced with the variant $\beta$APP ORF (FIG. 15a). Tg 2576 mice produced 5.56±0.33 units (mean±SEM) (73 day-old mice) to 5.76±0.74 units (430 day-old mice) of transgenic brain $\beta$APP expression, where one unit of expression is equivalent to the amount of endogenous mouse $\beta$APP in non-transgenic littermates (FIG. 15b). Transgenic $\beta$APP expression appeared to remain unchanged between two and 14 months of age.

Two groups of seven to nine transgene positive mice and 10 to 11 transgene negative littermates underwent spatial alternation testing in a Y-maze at three and 10 months of age. Three groups of nine to 13 transgene positive mice and 10 to 14 transgene negative littermates underwent spatial reference learning and memory testing in the Morris water maze (Morris, *J. Neurosci. Meth.* 11:47 (1984)) at two, six, and nine months of age. The test experience for each set of animals was novel, and all animals were tested in a coded manner. The nine to 10 month-old animals were N1-generation mice (C57B6×C57B6/SJL F1). The two to three and six month-old animals were N2-generation mice (C57B6×C57B6/SJL F1). A subset of the N2-generation mice (eight transgene positive and 10 transgene negative mice) were retested at 12 to 15 months of age.

Figure 16A:
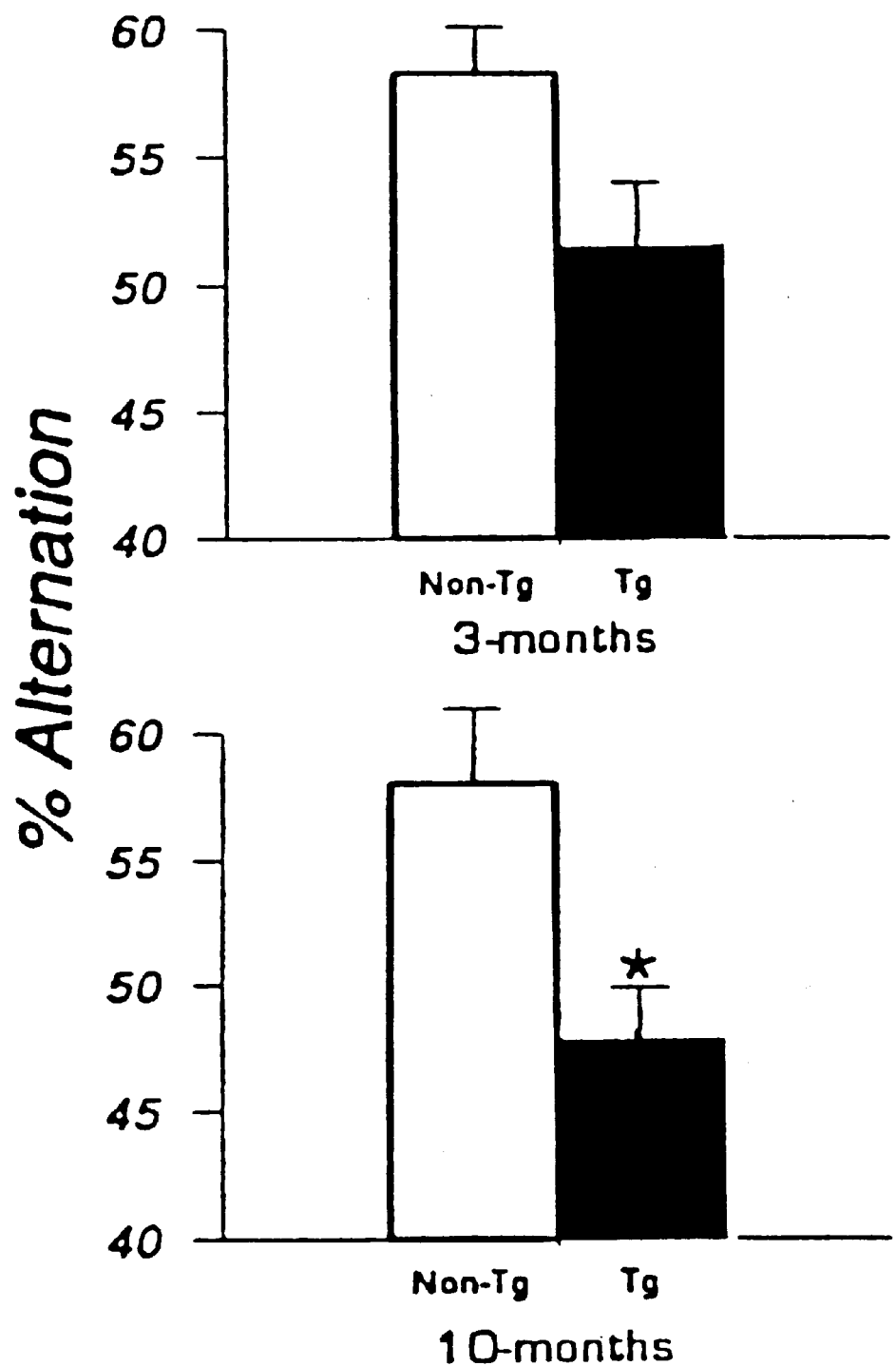
FIG. 16A, spatial alternation in a Y-maze. Transgene positive Tg2576 mice exhibit significantly impaired spatial alternation at 10 months of age but not three months of age. The methods used to perform this test are described in Hsiao, et al., (1995) *Neuron* 15: 1–16, except that the Y-maze was opaque and animals were observed from an overhead camera to eliminate visual distraction posed by the tester. Stars indicate statistical significance (t-test), $p<0.05$).

When transgene positive and transgene negative mice were given a choice of entering either of two arms in a Y-maze, they tended to alternate their choices spontaneously. Ten month-old transgene positive mice, however, showed significantly less tendency (p<.03) than age-matched transgene negative mice to alternate arms on successive choices (FIG. 16a). The behavior of the old transgene positive mice on the spatial alternation task is characteristic of animals with damage to the hippocampal formation (Douglas, *Spontaneous Alternation Behavior* Richman and Richman, Eds. (Springer-Verlag, New York, 1990) pp. 73–109).

Figure 16B:
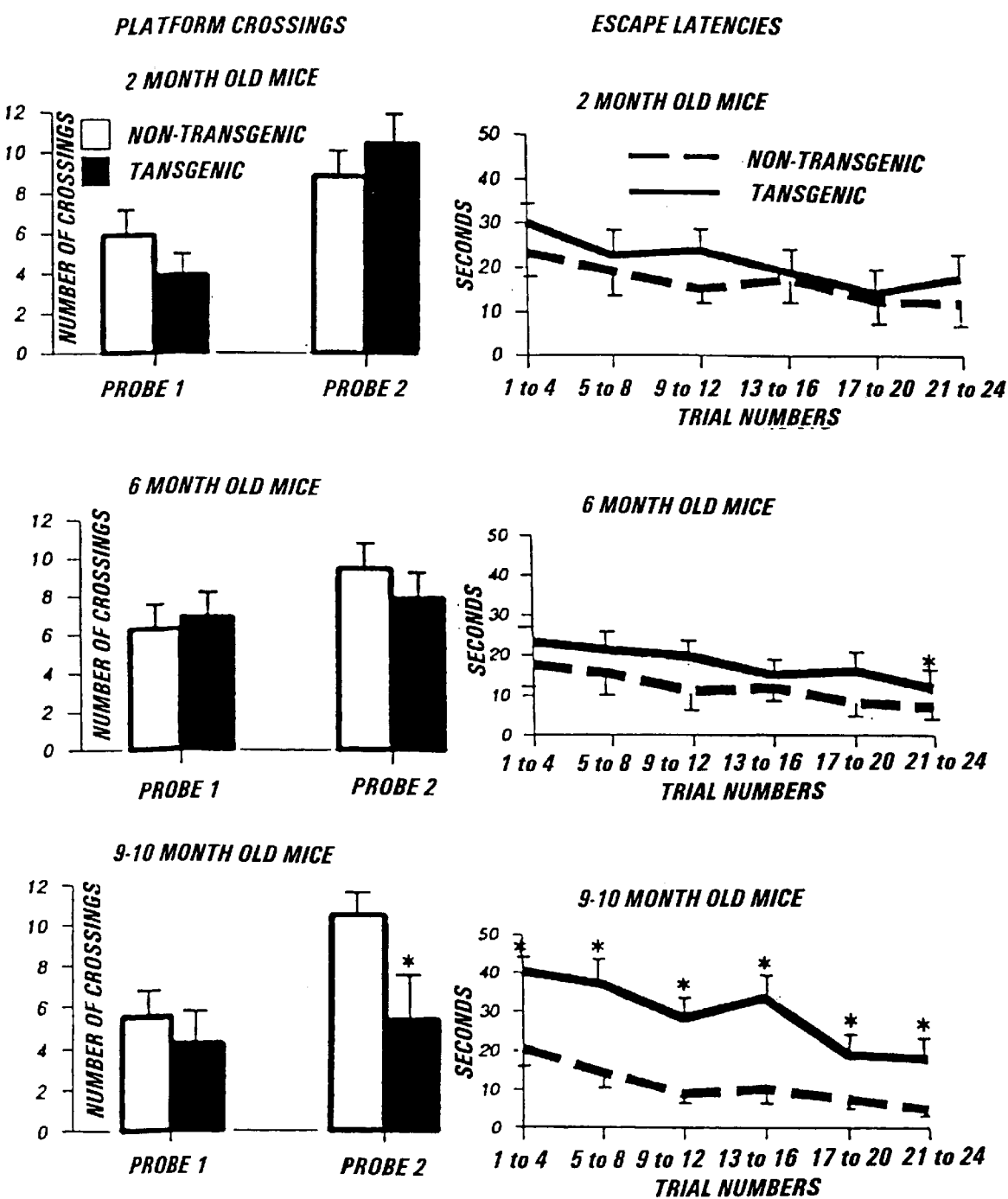
FIG. 16B, spatial reference learning and memory in the Morris water maze (Morris, (1984) *J. Neurosci. Meth.* 11:47) modified for use with mice. Transgene positive Tg2576 mice are able to learn and remember the location of the submerged platform at two and six months of age but show significant impairment by 9 to 10 months of age. Stars indicate statistical significance (t-test, $p<0.05$).

In another important learning test nine month-old transgene positive mice were impaired in their performance in the water maze relative to age-matched transgene negative mice (FIG. 16b). The water maze test described by Morris (1984) *J. Neurosci. Meth.* 11:47 was modified for use with mice. The water maze was a circular pool 1 meter in diameter filled with water maintained at 20° C. and made opaque by the addition of powdered milk. Animals were pretrained by swimming to a 12.7 cm square Plexiglas platform that was submerged 1.5 cm beneath the surface of the water and placed at random locations within the pool. During pretraining, heavy curtains were drawn around the pool so that mice were unfamiliar with the extramaze room cues on the first day of spatial training. Spatial training consisted of four trials per day, each trial lasting until the animal reached the platform or 60 seconds, whichever came first. After each trial, mice remained on the platform for 30 seconds. 24 hours after the $12^{th}$ and $24^{th}$ trials, all animals were subjected to a probe trial in which they swam for 60 seconds in the pool with the platform removed. Animals were monitored by a camera mounted in the ceiling directly above the pool, and all trials were stored on videotape for subsequent analysis of platform crossings and percent time spent in each quadrant during probe trials. Visible platform training was given at least 24 hours following the second probe trial, and consisted of swimming mice in the same pool described earlier except that the platform was now black, slightly larger (14.2 cm square), and raised above the surface of the water. The platform location was varied randomly from trial to trial to eliminate the potentially confounding contribution of extra-maze spatial cues.

In both visible platform and hidden platform versions, animals were placed in the pool facing towards the wall of the pool in one of seven randomly selected locations Transgene positive mice trained and tested at two or six months of age were not different from age-matched transgene negative mice on most measures. The amount of time taken by the mice to reach the hidden platform (the escape latency) did not differ between two month-old transgene positive and negative animals at any point during training, while the latency was significantly different (p<0.05) on every day for nine month-old animals. Six month-old transgene positive animals differed from controls in escape latency only on the last day of training. Probe trials, in which animals swam in the pool for 60 seconds with the platform removed, were given 24 hours after the $12^{th}$ and $24^{th}$ trials, and the number of times the animals crossed the platform location were recorded. This procedure often gives a more precise measure of the animals' knowledge of the platform location, and is less confounded by performance factors such as swim speed. Nine month-old transgene positive mice were significantly different (p<0.05) from age-matched transgene negative mice on the second probe trial, while two month-old and six month-old animals showed no differences on either probe trial.

When 12 to 15 month-old N2 generation transgene positive mice were retested in the water maze (after rearranging the extramaze cues), they showed significantly impaired performance compared to transgene negative littermates on escape latencies after the $5^{th}$ trial block and on probe trials given after the $6^{th}$ and $9^{th}$ trial blocks (FIG. 16c). These data suggest that the age-related learning impairment seen in N1 generation transgene postive mice can occur despite further genetic dilution of the SJL strain (FIG. 16c). Note that although the escape latencies of the transgene positive N2 mice are significantly longer than their transgene negative littermates, they are also shorter than naïve animals of comparable age. Thus deficits in escape latency in aged transgene positive animals are unlikely to result from difficulty in swimming, since aged mice given sufficient practice can swim as well as younger mice.

Figure 16D:
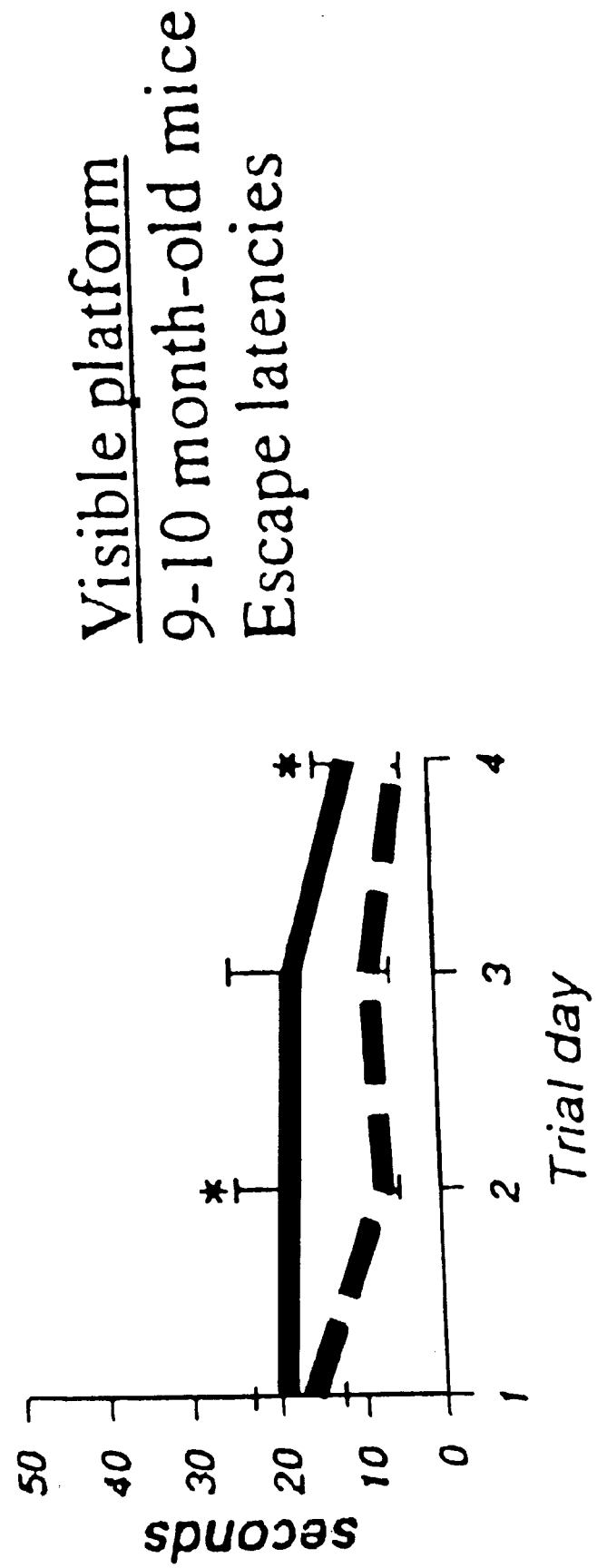
FIG. 16D, visually cued spatial reference test. Nine month-old transgene positive Tg2576 mice performing poorly in the submerged platform maze performed as well as transgene negative animals in the visually cued test on the first trial day, indicating that their poor performance in the submerged platform maze was due to neither visual nor motor impairment. The consistently higher escape latencies on trial days 2 through 4 may reflect more generalized cognitive impairment in the transgenic mice. Stars indicate statistical significance (t-test, p<0.05).

Since it is possible that the performance of older transgene positive mice is attributable to sensory or motor impairments, we also tested nine month-old mice on the visible-platform version of the water maze (FIG. 16d). Although differences in escape latency were evident on the second and fourth of four training days, there were no differences on Day 1. These data suggest that while older transgene positive mice may show generalized cognitive impairment, they are capable of performing as well as controls when both are relatively naïve. We also compared motor performance of the transgene positive and transgene negative nine month-old mice by scoring the total number of times during the probe trial each animal crossed imaginary platforms located in each of the four quadrants. If impaired animals swim normally but in a random pattern during probe trials, they should cross the center of all four quadrants combined as many times as unimpaired animals; they will simply cross the target platform fewer times. If, on the other hand, they are impaired on probe trials simply because they are not swimming, there will be fewer total platform crossings. In fact, the total number of platform crossings for transgene positive (24.4±8.7: mean±SEM) and transgene negative (29.5±1.4) mice was not significantly different indicating that motor impairment was not a cause of poor performance in the water maze.

Following behavioral testing a subset of each group of mice was sacrificed. One hemi-brain was frozen for cerebral cortical Aβ measurements and the other hemi-brain was immersion fixed for histopathological analysis. All brains were analyzed in a coded fashion. Measurements of Aβ1–40 and Aβ1–42(43) using either the Ban-50/Ba-27 or Ban-50/Bc-05 ELISA systems described previously (Suzuki, et al., Science 264:1335–1340 (1994); Gravina, et al., Journal of Biological Chemistry 270:7013–7016 (1995)) showed a five-fold increase in Aβ1–40 levels (p=0.03, rank sum test) and a 14-fold increase in Aβ1–42(43) levels (p=0.03, rank sum test) between the youngest (two to eight month) and oldest (11 to 13 month) transgene positive animals (Table 7). Thus there was a good correlation between significantly elevated Aβ levels and the appearance of memory and learning deficits in the oldest group of transgene positive animals.

TABLE 7

| Mouse # | Transgene status | Age when sacrificed (days) | Aβ(1–40) pmol/gm | Aβ(1–42) pmol/gm | Amyloid plaques 4G8*, 6E10[554] |
|---|---|---|---|---|---|
| Mice sacrificed between 11–13 months of age; transgene positive mice showed impaired spatial alternation and reference memory ||||||
| A01484 | Positive | 361 | 325 | 219 | +++ |
| A01488 | Positive | 354 | 192 | 129 | ++ |
| A01489 | Negative | 354 | <2 | <2 | ± |
| A01492 | Negative | 371 | <2 | <2 | − |
| A01493 | Positive | 368 | 273 | 177 | ++++ |
| A01495 | Negative | 354 | <2 | <2 | − |
| A01496 | Negative | 354 | <2 | <2 | ± |
| Mean ± SEM Aβ levels in transgene positive mice: | | | 264 ± 38 | 175 ± 26 | |

TABLE 7-continued

| Mouse # | Transgene status | Age when sacrificed (days) | Aβ(1–40) pmol/gm | Aβ(1–42) pmol/gm | Amyloid plaques 4G8*, 6E10[554] |
|---|---|---|---|---|---|
| Mice sacrificed between 6–8 months of age; transgene positive mice showed no learning and memory impairment ||||||
| A01984 | Negative | 233 | <2 | <2 | ± |
| A01987 | Negative | 219 | <2 | <2 | − |
| A01989 | Positive | 219 | 45 | 18 | − |
| A02561 | Negative | 214 | <2 | <2 | |
| A02595 | Negative | 207 | <2 | <2 | |
| Mice sacrificed between 2–5 months of age; transgene positive mice showed no learning and memory impairment ||||||
| A02428 | Negative | 139 | <2 | <2 | − |
| A02429 | Negative | 139 | <2 | <2 | |
| A02430 | Negative | 139 | <2 | <2 | − |
| A02565 | Positive | 118 | 71 | 21 | |
| A02900 | Negative | 85 | <2 | <2 | |
| A03103 | Positive | 67 | 32 | 2 | |
| A03107 | Positive | 67 | 45 | 10 | |
| Mean ± SEM Aβ levels in transgene positive mice: | | | 48 ± 8 | 13 ± 4 | |

*Brain tissue was stained with 4G8 (Kim, et al., Neurosci. Res. Commun. 2:121–130 (1988)), which recognizes both mouse and human Aβ.
†All amyloid deposits stained with 6E10 (Kim, et al., Neurosci. Res. Commun. 7:113–122 (1990)), which specifically recognizes human Aβ. No extracellular 6E10 staining was detected in three 105 to 106 day-old transgene positive mice or one 155 day-old transgene positive mouse (A01480, A01547, A01548, and Tg2576 founder - not included in behavioral studies shown).

Figure 17:
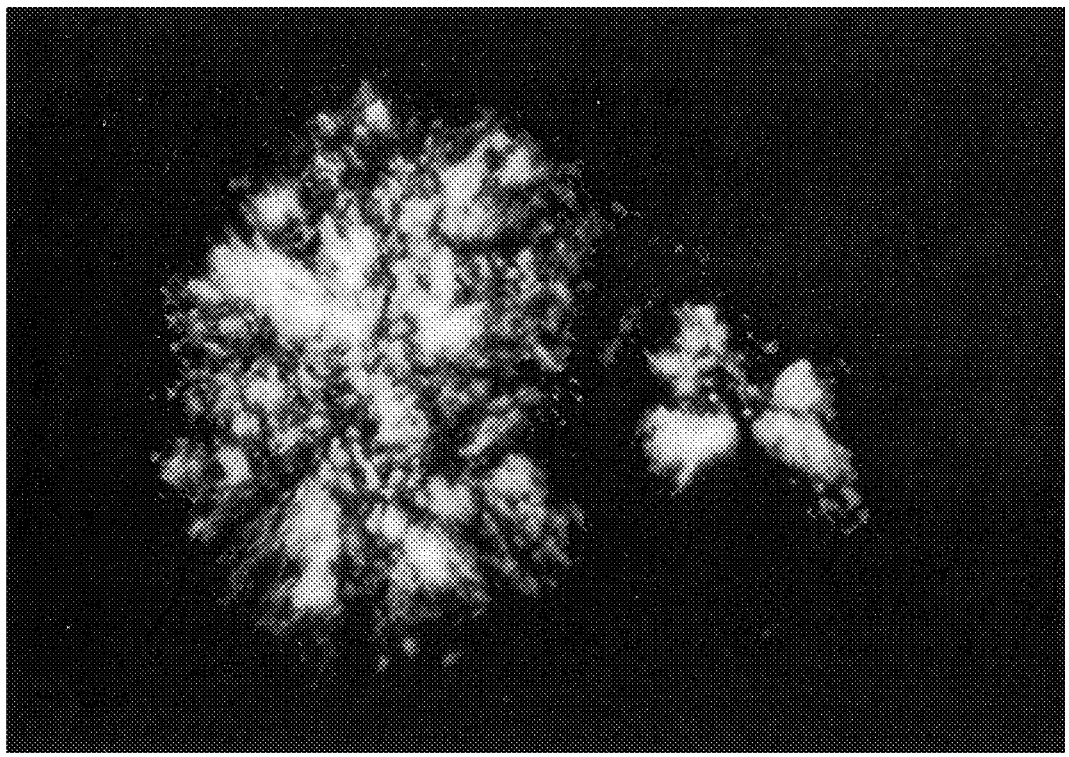
FIG. 17, extracellular amyloid deposits in Tg2576 transgenic mice #A01493 (368 days) and #A01488 (354 days) overexpressing human βAPP695 with the K670N-M671L mutation.
Figure 17A:
FIG. 17A, Tg2576-A01493, multiple plaques in the cerebral cortex and subiculum staining with 4G8 monoclonal antibody, 10x magnification.
Figure 17B:
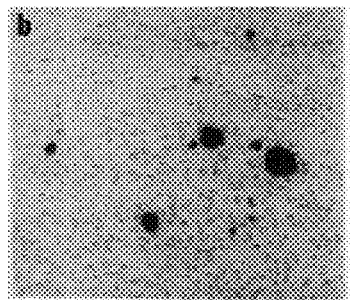
FIG. 17B, Tg2576-A01493, inset from panel A, 25x magnification.
Figure 17C:
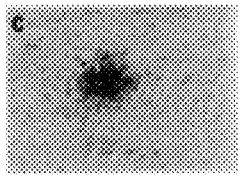
FIG. 17C, Tg2576-A01488, plaque in subiculum staining with 4G8antibody, 50x magnification.
Figure 17D:
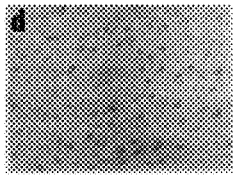
FIG. 17D, Tg2576-A01488, plaque in section adjacent to panel C fails to stain with 4G8 antibody pre-absorbed with β(14–24).
Figure 17F:
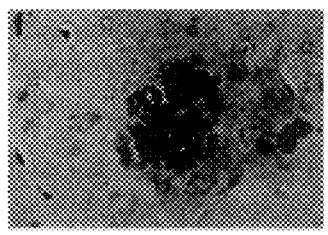
FIG. 17F, Tg2576-A01488, plaque staining with β1 affinity purified antiserum specifically recognizing the aminoterminus of Aβ, 100x magnification.
Figure 17G:
FIG. 17G, Tg2576-A01488, plaque staining with β42 affinity purified antiserum specifically recognizing the carboxyl terminus of Aβ(1–42), 100x magnification.
Figure 17E:
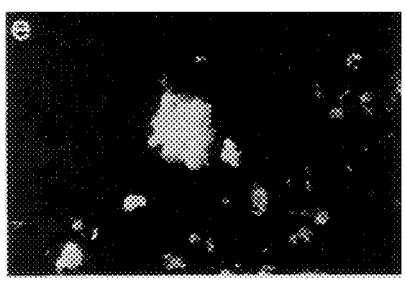
FIG. 17E, Tg2576-A01488, plaques staining with thioflavin S.
Figure 17H:
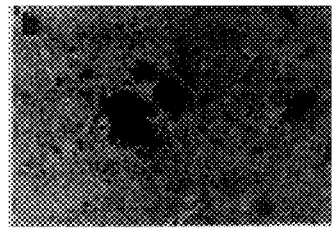
FIG. 17H, Tg2576-A01488, plaque staining with β40 affinity purified antiserum specifically recognizing the carboxyl terminus of Aβ(1–40), 50x magnification.

Aβ deposits were immunoreactive with antibodies recognizing β(1–5) (Saido, et al., J. Biol. Chemistry 269:15253–15257 (1994)), β(1–17) (Kim, et al., Neuroscience Research Communications 7:113–122 (1990)), β(17–24) (Kim, et al., Neurosci. Res. Commun. 2:121–130 (1988)), β(34–40) (Mak, et al., Brain Research 667:138–142 (1994)), β42/43 (Yang, et al., Neuroreport 5:2117–2120 (1994)) and free β42 (Harigaya, et al., BBRC 211:1015–1022 (1995)). The same plaques were readily identified with multiple antibodies on adjacent sections and were not seen with preimmune or non-specific ascites and the immunoreactivity was eliminated by preabsorption with the relevant peptides (FIG. 17). Deposits could not be found in the older transgene negative or younger transgene positive or negative mice examined. Both classic senile plaques with dense amyloid cores and diffuse deposits were present. The deposits were found in frontal, temporal and entorhinal cortex, hippocampus, presubiculum, subiculum and cerebellum in all three mice with elevated Aβ by ELISA assay. Dense amyloid plaques were most frequent in cortex, subiculum and presubiculum. The dense amyloid deposits were readily detected with thioflavin S fluorescence and typically also labeled with Congo red giving the characteristic apple green birefrigence of classical amyloid (Puchtler, et al., J. Histochem. Cytochem. 10:355–363 (1962)). Some small deposits had the "Maltese cross" signature pattern of the amyloid cores found in AD brain. Under high magnification, the thioflavin S and Congo red positive amyloid plaques usually exhibited wisps or fibers radiating from the central mass which was often ringed by glial nuclei with both astrocytic and microglial morphology. GFAP immunoreactive astrocytes were associated with amyloid deposition. Staining by the Gallyas silver method revealed dystrophic neurites surrounding dense core plaques.

In contrast to sporadic AD brain, antibodies to β1 and both free β42 and β(34–40) (which preferentially recognizes x-40) labeled the majority of deposits. This may reflect the βAPP670/671 mutations which greatly increases cleavage at the β1 site leading to high levels of all fragments beginning with the β1 epitope in contrast to the 717 mutations which increase the percentage of x-42 (Suzuki; et al., *Science* 264:1335–1340 (1994); Citron, et al., *Nature* 360:672–4 (1992)).

Our results demonstrate the feasibility of creating transgenic mice with both robust behavioral and pathological features resembling those found in AD, Tg2576 mice younger than nine months of age showing no significant deficits in spatial reference or spatial alternation learning and memory tasks possessed moderate levels of Aβ and no amyloid plaques. Impairment in learning and memory became apparent in mice nine months of age and older, correlating with markedly increased levels of Aβ and accompanied by numerous amyloid plaques and Aβ deposits. The rise in Aβ levels cannot be explained by a rise in transgenic βAPP expression, which appeared to remain unchanged with age. Aβ1–42(43) levels rose more dramatically than Aβ1–40 levels. Interestingly, this parallels the finding in humans with presenilin 1 and presenilin 2 mutations exhibiting more significant elevations of Aβ1–42(43) than Aβ1–40 in serum and cultured fibroblasts (S. Younkin, unpublished data). Ongoing studies correlating individual performance in learning and memory tests with levels of Aβ and extent of amyloid deposition are being done to ascertain the contribution of each parameter to behavioral deficits.

Earlier attempts to produce transgenic mice with robust extracellular Aβ deposits were largely unsuccessful with the exception of mice reported by Games and colleagues (Games, et al., *Nature* 373:523–527 (1995)). βAPP expression was driven in their mice by a PDGF promoter. Our studies show that the PrP promoter can also be used to create transgenic mice with Aβ deposits. Both the PDGF and PrP promoters drive βAPP expression chiefly in neurons of the cerebrum and cerebellum. Clearly, the βAPP variant with K670N-M671L is effective, as is V717F, in promoting abundant plaque deposition. The mice of Games and colleagues and Quon and colleagues (Quon, et al., *Nature* 352:239–41 (1991)) expressed largely or exclusively βAPP containing the KPI domain. We have demonstrated that a βAPP transgene lacking the KPI domain also is capable of engendering amyloid plaques in mice.

These transgenic mice are unique in developing deficits in learning and memory associated with elevated Aβ levels and the appearance of classic senile plaques with dense amyloid cores. Whether the learning and memory deficits in these mice are caused by or merely correlate with a rise in brain Aβ levels and amyloid deposition remains unresolved. Further refinements in temporal correlations between behavioral, biochemical, and histological changes in these transgenic mice may provide answers to this fundamental question. The value of these mice resides in their correlative manifestation of learning and memory deficits, elevated Aβ levels, and amyloid plaques, providing new opportunities to study the electrophysiology, pathophysiology, biochemistry, genetics, and neurobiology of AD.

Example 9

Testing for Drugs That Prevent Progressive Neurologic Disease

The animals of the invention are used to test materials for the ability to confer protection against the development of progressive neurologic disease. An animal exhibiting the progressive neurologic disease is treated with a test material in parallel with an untreated control transgenic animal exhibiting the neurologic disease. A comparatively lower incidence of the progressive neurologic disease in the treated animal is detected as an indication of protection. Treated and untreated animals are analyzed for diminished exploratory/locomotor behavior (CI test; see Example 6), as well as diminished 2-deoxyglucose uptake/utilization and hypertrophic gliosis in the cortico-limbic structures of the brain. To determine if a treatment can prevent or delay the onset of disease, half of the transgenic mice in a litter from a line of mice known to develop neurologic illness may be randomly assigned to receive the treatment, and the other half to receive a placebo, beginning at an age prior to the earliest known onset of disease for the given line of mice. The number of litters to be used will depend upon the magnitude of the differences observed between treated and untreated mice.

Mice are observed daily; their diagnosis is facilitated by the use of the CI test (see Example 6) which is administered three times per week by individuals blinded to the experimental groups. Survival curves and mean ages of disease onset and death are calculated from the accumulated clinical data.

Clinical results are corroborated by performing neuropathologic and glucose-uptake studies in samples in the experimental and control groups. Gliosis is evaluated in immunohistologic studies using antibodies to glial fibrillary acidic protein. Glucose-uptake studies are performed using a modification of the Sokoloff method described by Chmielowska, et al., (1986) *Exp. Brain Res.* 63:607.

To determine if a treatment can ameliorate or cure disease, sick littermates are randomly assigned to receive the treatment of interest or a saline placebo. Survival and clinical improvement on the CI test coupled with neuropathologic and glucose-uptake studies are ascertained, as described above.

Example 10

Testing for Drugs That Cure Progressive Neurologic Disease

The animals of the invention are used to test materials for the ability to improve or cure progressive neurologic disease. An animal exhibiting the progressive neurologic disease is treated with a test material in parallel with an untreated control transgenic animal exhibiting the neurologic disease. A comparatively delayed death, or an improvement in the neurobehavioral, pathologic, or functional indications of the disease is detected as an indication of protection. Treated and untreated animals are analyzed for diminished exploratory/locomotor behavior, as well as diminished 2-deoxyglucose uptake/utilization and hypertrophis gliosis in the cortico-limbic structures of the brain.

As demonstrated by the above results, the clinical and pathologic findings in non-human mammals with super endogenous levels of either mutant or native amyloid precursor protein show an unexpected, but striking parallel to these in humans with progressive neurologic disorders such as Alzheimer's disease; the involved regions of the neocortex in affected transgenic mice and humans are similar. In addition, glucose uptake in the sensorimotor area of the cerebral cortex was unaffected by the neurologic disease in transgenic mice. This was the only region of mouse neocortex sampled which represented mainly primary neocortex, rather than a mixture of primary and association neocortex. It is a well-known observation that in brains of patients with Alzheimer's disease, the primary neocortex is relatively free of neuropathologic findings compared to the association cortex.

The CNS phenotype of the transgenic mice closely resembles the CNS phenotype of a subset of aged non-transgenic mice of the same FVB strain. The gliosis in the hippocampus astrocytic gliosis that is characteristically found in the hippocampal formations of aged, memory-deficient rats (Landfield, et al. (1977) *J. Gerontology* 32:2–12) and aged, nude mice (Mandybur, et al., (1989) *Acta Neuropathol (Berl.)* 77:507–513). The regional glucose hypometabolism in both the affected transgenic mice and the aged, impaired non-transgenic mice was markedly diminished in the hippocampus, cerebral cortex, and amygdala, resembling the pattern of glucose hypometabolism occurring in humans with AD (de Leon, et al., (1983) *Am. J. Neuroradiology* 4:568–571), and in restricted areas of the limbic system in aged, impaired Sprague-Dawley rats (Gage, et al., (1984) *J. Neuroscience* 11:2856–2865). The striking similarities in the neurologic disease exhibited by the transgenic animals and the naturally occurring disorder in older mice of the same strain support the use of these transgenic mice as a model for progressive senescent disorders of the brain, including Alzeheimer's disease.

Animals dying of neurologic disease exhibited hypertrophic gliosis in the hippocampus, amygdala, and some areas of the cerebral cortex. Immunohistologic mapping of HuAPP in the transgenic mice indicated widespread expression throughout the brain. However, the behavioral abnormalities corresponded to the circumscribed regions of gliotic pathology and glucose hypo-utilization found in select forebrain regions. The striking similarities in target cell specificities in cortico-limbic areas of the brain (hippocampus, amygdala, and some areas of cerebral cortex) in these transgenic mice and Alzheimer's disease support the use of these transgenic mice as a model for pprogressive neurologic disorders such as Alzheimer's disease.

In summary, these transgenic mice express super-endogenous levels of APP. In the mouse lines which develop neurologic disease, APP transgene product expression with at least 200% of endogenous levels has been attained, or more than double that reported in any prior publications. More importantly, these mice have a definite, progressive neurologic disorder. Even where APP expression has been achieved in other transgenic mice, they have not developed a progressive disease affecting the cortico-limbic areas of the brain. Transgenic mice (FVB/N) overexpressing wild-type and variant human or mouse βAPP695 develop a central nervous system disorder involving cortico-limbic regions of the brain sparing somatosensory-motor areas that resembles an accelerated naturally occurring senescent disorder of FVB/N mice. Parameters that influence the phenotype of transgenic mice expressing βAPP include host strain, βAPP primary structure, and levels of βAPP expression. Transgenic mice overexpressing the 695-amino acid isoform of human K670N-M671L Alzheimer β-amyloid precursor protein (βAPP) have normal learning and memory in spatial reference and alternation tasks at three months of age but show impairment by nine to ten months of age. A five-fold increase in Aβ1–40 and 14-fold increase in Aβ1–42(43) accompanied the appearance of these behavioral deficits. Numerous congophilic Aβ plaques were present in cortical and limbic structures in mice with elevated Aβ levels. The correlative appearance of behavioral, biochemical and pathological abnormalities reminiscent of Alzheimer's disease (AD) affords new opportunities for exploring the pathophysiology and neurobiology of AD in mice.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the are that many changes and modifications can be made thereto without departing from the spirit or scope of the appended claims.

What is claimed is:

1. A transgenic mouse whose genome comprises a transgene, said transgene having a prion gene promoter operably linked to a sequence encoding an amyloid precursor protein (APP), said APP having at least one mutation associated with Alzheimer's disease, wherein said transgenic mouse produces amyloid plaques that are detectable by Congo red staining in the brain of said transgenic mouse.

2. The transgenic mouse of claim 1, wherein said at least one mutation comprises the Swedish mutation.

3. The transgenic mouse of claim 1, wherein said at least one mutation comprises a mutation at amino acid 717.

4. The transgenic mouse of claim 3, wherein a phenylalanine or a glycine residue is substituted for a valine at amino acid 717.

5. The transgenic mouse of claim 1, wherein a non-transgenic ancestor of said mouse is from a strain selected from the group consisting of Swiss Webster and C57B6.

6. Progeny of said transgenic mouse according to claim 1, wherein the genomes of said progeny comprise said transgene, wherein said progeny exhibit amyloid plaques that are detectable by Congo red staining in the brain of said progeny.

* * * * *